(12) United States Patent
Nivorozhkin et al.

(10) Patent No.: US 10,252,982 B2
(45) Date of Patent: Apr. 9, 2019

(54) NEURO-ATTENUATING KETAMINE AND NORKETAMINE COMPOUNDS, DERIVATIVES THEREOF, AND METHODS

(71) Applicant: Amorsa Therapeutics, Inc., Littleton, MA (US)

(72) Inventors: Alex Nivorozhkin, West Roxbury, MA (US); Nelson Landrau, Marlborough, MA (US)

(73) Assignee: Amorsa Therapeutics, Inc., Littleton, MA (US)

( * ) Notice: Subject to any disclaimer, the term of this patent is extended or adjusted under 35 U.S.C. 154(b) by 0 days.

(21) Appl. No.: 15/524,224

(22) PCT Filed: Nov. 4, 2015

(86) PCT No.: PCT/US2015/059113
§ 371 (c)(1),
(2) Date: May 3, 2017

(87) PCT Pub. No.: WO2016/073653
PCT Pub. Date: May 12, 2016

(65) Prior Publication Data
US 2017/0355663 A1 Dec. 14, 2017

Related U.S. Application Data

(60) Provisional application No. 62/074,645, filed on Nov. 4, 2014.

(51) Int. Cl.
| | | |
|---|---|---|
| C07C 225/20 | (2006.01) |
| C07B 59/00 | (2006.01) |
| A61K 45/06 | (2006.01) |
| A61K 9/20 | (2006.01) |
| A61K 31/135 | (2006.01) |

(52) U.S. Cl.
CPC .......... *C07C 225/20* (2013.01); *A61K 9/2013* (2013.01); *A61K 9/2027* (2013.01); *A61K 9/2031* (2013.01); *A61K 9/2054* (2013.01); *A61K 31/135* (2013.01); *A61K 45/06* (2013.01); *C07B 59/001* (2013.01); *C07B 2200/05* (2013.01); *C07C 2601/14* (2017.05)

(58) Field of Classification Search
CPC .................................................. C07C 225/20
See application file for complete search history.

(56) References Cited

U.S. PATENT DOCUMENTS

| | | | |
|---|---|---|---|
| 5,384,331 A | 1/1995 | Kogan et al. |
| 9,913,803 B2 | 3/2018 | Nivorozhkin et al. |
| 2004/0248964 A1 | 12/2004 | Crooks et al. |
| 2008/0020039 A1 | 1/2008 | Parikh et al. |
| 2008/0268071 A1 | 10/2008 | Gant et al. |
| 2018/0153813 A1 | 6/2018 | Nivorozhkin et al. |

FOREIGN PATENT DOCUMENTS

| | | |
|---|---|---|
| WO | 2004045601 A1 | 6/2004 |
| WO | 2009131794 A1 | 10/2009 |

OTHER PUBLICATIONS

Supplementary European Search Report dated Mar. 5, 2018 in corresponding European Application No. EP 15856205.
Sulake et al: "Synthesis of deuterium labeled ketamine metabolite dehydronorketamine-", Bioorganic & Medicinal Chemistry Letters, vol. 21, No. 19, Aug. 3, 2011, pp. 5719-5721.
Database Registry [Online] Chemical Abstracts Service, Columbus, Ohio, US; Jun. 7, 2013, XP002779946, Database accession No. 1435934-57-8, abstract.
Ebert B et al: "Norketamine, the main metabolite of ketamine, is a non-competitive NMDA receptor antagonist in the rat cortex and spinal cord," European Journal of Pharmacology, vol. 333, No. 1, Aug. 20, 1997, pp. 99-104, Elsevier Science, abstract.
Leung et al: "Comparative pharmacology in the rat of ketamine and its two principal metabolites, norketamine and (Z)-6-hydroxynorketamine," Journal of Medicinal Chemistry, vol. 29, No. 11, Jan. 1986, pp. 2396-2399, abstract.
Foster A B: "Deuterium isotope effects in the metabolism of drugs and xenobiotics: implications for drug design," Advances in Drug Research, vol. 14, Jan. 1985 (Jan. 1985), pp. 1-40.

(Continued)

*Primary Examiner* — Paul V Ward
(74) *Attorney, Agent, or Firm* — Mintz Levin Cohn Ferris Glovsky and Popeo, P.C.; Peter F. Corless; Joohee Lee

(57) ABSTRACT

The present invention is directed to novel neuro-attentuating norketamine (NANKET) compounds according to any one of formulas (I-shown below), (I-A) and (I-B)), or any of the compounds described in Tables A-D, or in any of the Examples provided herein, and pharmaceutically acceptable salts thereof, novel pharmaceutical formulations and novel methods of uses thereof. The present invention also features novel oral neuro-attenuating ketamine (NAKET) and neuro-attenuating norketamine (NANKET) modified-release pharmaceutical formulations, and novel methods of administration thereof, which ensure the steady release of a therapeutically effective amount of ketamine, norketamine, or derivatives thereof from the oral modified-release pharmaceutical formulations without neurologically toxic spikes in plasma concentration of the ketamine, norketamine, or derivatives during the release periods.

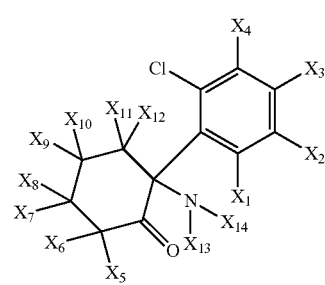

48 Claims, 7 Drawing Sheets

(56) References Cited

OTHER PUBLICATIONS

Dumont et al., "Prospects in the use of deuterated molecules as therapeutic agents," Revue, vol. 6, No. 4, Jan. 1982, pp. 2-10, Institut National Des Radioelements, Belgium.
Yarnell: "Heavy-Hydrogen Drugs Turn Heads, Again," Internet Citation, Jun. 22, 2009, pp. 36-39, Retrieved from the Internet: URL:<http://pubs.acs.org/cen/science/87/8725sci1.html [retrieved on Sep. 16, 2009].
Harun et al., "Validation of an Enzyme-Linked Immunosorbent Assay Screening Method and a Liquid Chromatography-Tandem Mass. Spectrometry Confirmation Method for the Identification and Quantification of Ketamine and Norketamine in Urine Samples from Malaysia," Journal of Analytical Toxicology, vol. 33, No. 6, Jul. 2009, pp. 310-321.
Zhao et al., "Simultaneous population pharmacokinetic modelling of ketamine and three major metabolities in patients with treatment-resistant bipolar depression," British Journal of Clinical Pharmacol, vol. 74, No. 2, Aug. 2012, pp. 304-314.
Lai et al., "Ketamine Metabolism: Identification and Synthesis of a Deaminated Product" Journal of Pharmaceutical Sciences, vol. 74, No. 4, Apr. 1985, pp. 486-488, p. 2, scheme I.
International Search Report and Written Opinion dated Feb. 4, 2016, in corresponding PCT application No. PCT/US15/59113.
Applicant's Response dated Dec. 3, 2018 response to EPO Communication pursuant to Rule 70(2) and 70(a)(2) EPC dated May 23, 2018.
Communication pursuant to Rules 70(2) and 70a(2) EPC dated May 3, 2018 issued in counterpart European Application 15856205.8.

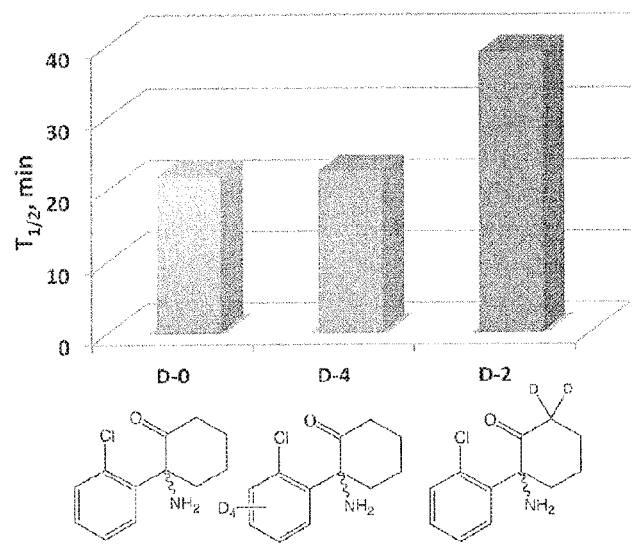
Figure 6. Rat Liver Homogenate Metabolic Assay of (left to right) norketamine, compound 12, and compound 11.

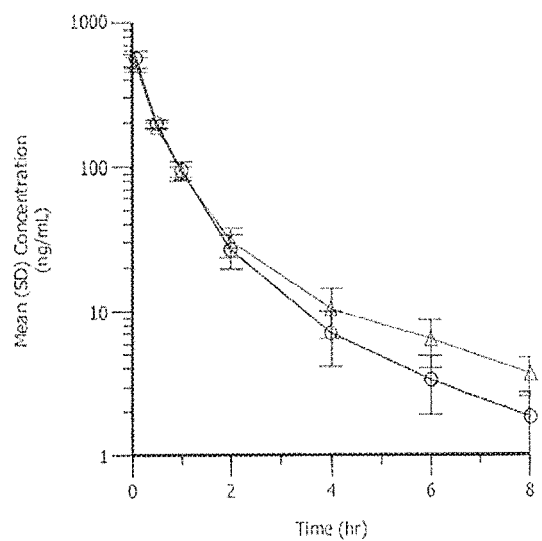
Figure 7. PK Data in Rats (triangles denote bis-deuterated norketamine compound 11, circles relate to the non-deuterated norketamine).

NEURO-ATTENUATING KETAMINE AND NORKETAMINE COMPOUNDS, DERIVATIVES THEREOF, AND METHODS

I. CROSS-REFERENCE TO RELATED APPLICATIONS

This application is a National Phase application filed under 35 USC 371 of PCT International Application No. PCT/US2015/059113 with an International Filing Date Of Nov. 4, 2015, claims benefit of U.S. Provisional Application No. 62/074,645, filed on Nov. 4, 2014, which is incorporated herein by reference in its entirety.

II. BACKGROUND

Ketamine is a non-selective N-methyl-d-aspartate (NMDA) receptor antagonist that has been approved by FDA for induction and maintenance of the general anesthesia. It has also been shown effective in treating other conditions, for example, to alleviate different kinds of pain (Correll, 2003), depression (Zarate, 2012), acute brain injury and stroke (Hertle, 2012), epilepsy (Synowiec, 2013), alcohol dependence, Alzheimer's disease, asthma and other disorders.

The oral efficacy of ketamine for treatment of pain has been confirmed by multiple investigators and recently reviewed (Blonk, 2010). In most cases, ketamine was used as an oral solution prepared from the commercially available injectable formulation (1 or 10% ketamine in water), often times mixed with fruit juice or syrup for taste masking. Solid dose forms of ketamine have also been reported in several examples. In particular, Yanagihara et al. (Yanagihara 1999, 2003) reported preparation of oral tablets of ketamine by dry and wet granulation with pharmacokinetics in humans similar to the orally administered syrup formulation. Furthermore, oral and sublingual formulations of ketamine as gelatin-based lozenges having a total weight of 1 g and ketamine load of 25 mg have also been prepared by Chong (Chong, 2009).

When administered orally, ketamine is a subject to the first-pass liver metabolism via N-demethylation and conversion to the active metabolite Norketamine. The elimination half-life of ketamine has been estimated at 2-3 hours, and 4 hours for norketamine. Consequently, the therapeutic window of orally administered ketamine is relatively short, and prompts an oral administration of multiple daily doses of the drug, e.g., 3-5 times a day, to achieve desirable therapeutic effect.

Moreover, solid dose forms of ketamine have been consistently limited by their inability to provide therapeutically effective doses, even in the short-term, without neurologically toxic spikes in ketamine concentration. In fact, exceeding an optimal efficacy plasma concentration of the drug (10-300 ng/ml) leads to more pronounced side effects, such as sedation, hallucination, dizziness, and/or nausea, which can not only have immediate repercussions, but also effect treatment compliance.

In order to achieve the optimal therapeutic index, the most successful route of administration for maintaining the stable levels of the drug in the system over longer periods of time appears to be by infusion (Correll, 2004). Such administration affords direct titration control of the manner of the administration, and enables eliminating the presence of neurological side effects, e.g., resulting from psychotomimetic toxic plasma concentration spikes of ketamine. However, the process of infusion presents significant challenges in patient management, as well as the cost of the procedure, being difficult to administer outside of the Intensive Care Units (ICU).

As such, there remains a need for efficient, more convenient, and controllable ketamine formulations that mimic the results of ketamine infusion and afford no neurologically toxic (e.g., psychotomimetic toxic) plasma concentrations, and which address the identified gap in ketamine treatment of conditions such as pain, depression, traumatic brain injury, stroke, epilepsy, alcohol dependence, or Alzheimer disease.

III. SUMMARY OF THE INVENTION

The present invention overcomes the above-mentioned disadvantages and drawbacks associated with ketamine therapy and is directed to the discovery of novel, isolated and/or substantially pure, isotopically-enriched, neuro-attenuating norketamine compounds, novel pharmaceutical compositions formulated therewith and methods of use thereof, for the (i) treatment of a subject diagnosed with, suffering from or susceptible to, (ii) prevention and/or (iii) management of a disease, disorder or condition, such as those for which ketamine treatment may be considered, indicated, tried or recommended, including pain, depression, anxiety, traumatic brain injury, stroke, migraines, epilepsy, schizophrenia, asthma, post traumatic disorder, bipolar disorder, alcohol dependence, Alzheimer disease, suicidality, autism, diabetic neuropathy, tinnitus, levodopa-induced dyskinesia, speudobulbar effect, Bulbar function, and the like.

In accordance with the present invention, the novel, isolated and/or substantially pure, isotopically-enriched, neuro-attenuating norketamine compounds may be formulated into pharmaceutical compositions suitable for oral immediate release and modified-release), parenteral, topical, rectal, vaginal, intranasal, inhalation or liquid administration, such as oral dosage forms like pills (e.g., tablets, capsules, caplets, troaches, lozenges, caches, gelcaps, caps, pellets, boluses, pastilles, orally disintegrating tablets, sublingual tablets and buccal tablets), thin films, powders, granules, crystals, liquid solutions, syrups, emulsions and suspensions, topical dosage forms like pastes, creams, ointments, gels, liquids, sprays, skin patches, dermal patches, balms, salves and implants, ophthalmic and otic dosage forms, e.g., drops, suspensions, emulsions, creams and gels, vaginal rings and inserts, suppositories, inhalation dosage forms like aerosols, inhalers, nebulizers and vaporizers, and parenteral dosage forms like intradermal (ID), intramuscular (IM), intraosseous (IO), intraperitoneal (IP), intravenous (IV), caudal, intrathecal (ITH), subcutaneous (SC), and the like.

Also in accordance with the present invention, the novel, isolated and/or substantially pure, isotopically-enriched, neuro-attenuating norketamine compounds and the novel pharmaceutical compositions formulated therewith are suitable to (i) treat a subject for any indication for which ketamine treatment may be considered, tried, indicated or recommended, whether or not the ketamine indication is an FDA-approved indication or an off-label indication, and/or (ii) prevent and/or manage any disease, disorder or condition for which ketamine treatment may be considered, tried, indicated or recommended, including but not limited to the treatment, prevention and/or management of any disease, disorder or condition that concerns, for example, pain, depression, anxiety, traumatic brain injury, stroke, migraines, epilepsy, schizophrenia, asthma, post traumatic disorder, bipolar disorder, alcohol dependence, Alzheimer disease, suicidality, autism, diabetic neuropathy, tinnitus, levodopa-induced dyskinesia, speudobulbar effect, Bulbar function and the like.

The present invention is also directed to the discovery of novel, oral, modified-release neuro-attenuating ketamine (NAKET) and/or neuro-attenuating norketamine (NANKET) pharmaceutical formulations, and methods of use thereof, for oral administrations, such as oral modified-release tablet formulations, for providing improved therapeutic and safety profiles, as compared with existing compositions of oral ketamine. In this regard, the novel oral neuro-attenuating ketamine (NAKET) and/or neuro-attenuating norketamine (NANKET) pharmaceutical formulations are uniquely designed to ensure the steady release of therapeutically effective amounts of a NAKET compound, e,g., ketamine and/or any compound of Formula II, and/or a NANKET compound, e.g., norketamine, any compound of Formula I, (I-A), (I-B) and/or any of the compounds described in Tables A-D, from the novel oral pharmaceutical formulations for the duration of the release periods in a subject following an oral administration event. Quite surprisingly, the novel, oral, modified-release neuro-attenuating ketamine (NAKET) and/or neuro-attenuating norketamine (NANKET) pharmaceutical formulations of the present invention accomplish this therapeutic effect, as contemplated by the present invention, without causing neurologically toxic spikes in ketamine and/or norketamine plasma concentrations that may induce side-effects of, for example, sedation and/or psychotomimeic effects, such as hallucination, dizziness, and nausea.

In addition, the present invention provides novel derivatives for use in the formulations and methods of the present invention. In particular embodiments, the present invention provides oral pharmaceutical formulations of NAKET compounds and/or NANKET compounds. In certain specific embodiments, oral, modified-release pharmaceutical formulations of the present invention, and methods of administration, provide unique steady administration of NAKET compounds and/or NANKET compounds to a subject during release periods of about 12 hours or greater, for example, for about 24 hours or greater, for about 36 hours or greater, or for even about 48 hours or greater, after a single oral administration event, to now provide safe and therapeutically effective oral treatments of subjects with NAKET compounds and/or NANKET compounds, including ketamine and norketamine.

Accordingly, in one aspect of the present invention, it provides a compound of formula I:

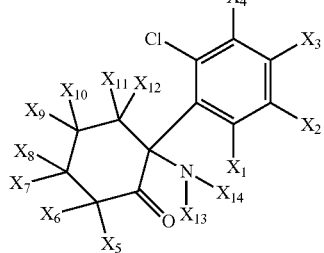

(I)

wherein
$X_1$, $X_2$, $X_3$, $X_4$, $X_5$, $X_6$, $X_7$, $X_8$, $X_9$, $X_{10}$, $X_{11}$, $X_{12}$, $X_{13}$, and $X_{14}$ are each independently selected from the group consisting of hydrogen and deuterium, and wherein at least one of $X_1$, $X_2$, $X_3$, $X_4$, $X_5$, $X_6$, $X_7$, $X_8$, $X_9$, $X_{10}$, $X_{11}$, $X_{12}$, $X_{13}$, and $X_{14}$ is deuterium,
or a salt thereof.

In another aspect, the present invention provides for a novel pharmaceutical formulation comprising a compound of formula I, (I-A), (I-B), and/or any of the compounds described in Tables A-D.

In yet another aspect, the present invention provides an orally administrable, modified-release pharmaceutical composition, e.g., a modified-release, single-layer tablet composition, such as a modified-release, single-layer tablet formulated with a matrix composition, comprising a therapeutically effective amount of a neuro-attenuating norketamine (NANKET) compound, including norketamine, any compound of Formula I, (I-A), (I-B) and/or any of the compounds described in Tables A-D.

In still another aspect of the present invention, it provides for a novel pharmaceutical formulation comprising a neuro-attenuating ketamine (NAKET) compound, including ketamine, represented by formula II:

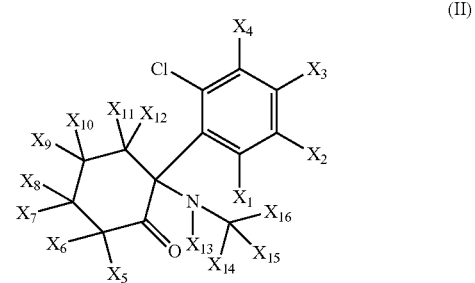

(II)

wherein
$X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, and $X_{16}$ are each independently selected from the group consisting of hydrogen and deuterium, and wherein at least one of $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, and $X_{16}$ is deuterium.

In another aspect of the present invention, it provides for an orally administrable, modified-release pharmaceutical composition, e.g., a modified-release, single-layer tablet composition, such as a modified-release, single-layer tablet formulated with a matrix composition, comprising a therapeutically effective amount of a neuro-attenuating ketamine (NAKET) compound, including ketamine and/or any compound of Formula II.

Like with the novel, isolated and/or substantially pure, isotopically-enriched, neuro-attenuating norketamine compounds, the novel, oral, modified-release pharmaceutical compositions formulated with a neuro-attenuating ketamine (NAKET) compound and/or a neuro-attenuating norketamine (NANKET) compound, including norketamine, any compound of Formula I, (I-A), (I-B) and/or any of the compounds described in Tables A-D, are suitable to (1) treat a subject for any indication for which ketamine treatment may be considered, tried, indicated or recommended, whether or not the ketamine indication is an FDA-approved indication or an off-label indication, and/or (2) prevent and/or manage any disease, disorder or condition such as those for which ketamine treatment may be considered, tried, indicated or recommended. Thus, in another unique aspect, the present invention provides for a method of treating a subject comprising the step of administering to a subject in need thereof an oral, modified-release pharmaceutical composition of the present invention formulated with a therapeutic effective amount of a neuro-attenuating ketamine (NAKET) compound, including ketamine and any compound of Formula II, and/or a neuro-attenuating norketamine (NANKET) compound, including norketamine, any compound of Formula I, (I-A), (I-B) and any of the compounds described in Tables A-D, as described herein, e.g., an oral modified-release, single layer, tablet composition, such that (1) the subject is effectively treated without causing neurologically toxic spikes in ketamine and/or norketamine plasma concentrations in the subject following an oral administration event, and/or (2) a disease, disorder and/or condition, such as those for which ketamine treatment may be considered, tried, indicated or recommended, such as pain, depression, anxiety, traumatic brain injury, stroke, migraines, epilepsy, schizophrenia, asthma, post traumatic disorder, bipolar disorder, alcohol dependence, Alzheimer disease, suicidality, autism, diabetic neuropathy, tinnitus, levodopa-induced dyskinesia, speudobulbar effect, Bulbar function and the like, are effectively treated, prevented and/or managed, without causing neurologically toxic spikes in ketamine and/or norketamine plasma concentrations in the subject following an oral administration event.

In view of the above, it should now be readily apparent to those of skill in the ketamine art that the present invention offers significant advantage over current ketamine treatment affording prescribing practitioners a safe and effective alternative to current ketamine therapy that can mimic ketamine infusion therapy and provide a therapeutic benefit in the treatment, prevention and/or management of a disease, disorder and/or condition for which ketamine treatment may be considered, tried, indicated or recommended, including but not limited to the treatment, prevention and/or management of any disease, disorder or condition that concerns, for example, such as pain, depression, anxiety, traumatic brain injury, stroke, migraines, epilepsy, schizophrenia, asthma, post traumatic disorder, bipolar disorder, alcohol dependence, Alzheimer disease, suicidality, autism, diabetic neuropathy, tinnitus, levodopa-induced dyskinesia, speudobulbar effect, Bulbar function and the like.

Quite surprisingly, the novel oral, modified-release NAKET and/or NANKET pharmaceutical formulations and methods of the present invention accomplish this important and needed therapeutic objective by strategically achieving and maintaining therapeutically effective ketamine and/or norketamine plasma concentrations, e.g., no more than about a 10-300 ng/ml ketamine plasma concentration, throughout the drug release period from the oral, modified-release NAKET and/or NANKET pharmaceutical formulations following the oral administrative events to effectively treat, prevent and/or manage a disease, disorder and/or condition, without causing neurological toxic spikes in ketamine and/or norketamine plasma concentrations.

IV. BRIEF DESCRIPTION OF FIGURES

The foregoing and other objects, advantages and features of the present invention, and the manner in which the same are accomplished, will become more readily apparent upon consideration of the following detailed description of the invention taken in conjunction with the accompanying figures and examples, which illustrate embodiments of the present invention, wherein.

Figure 1:
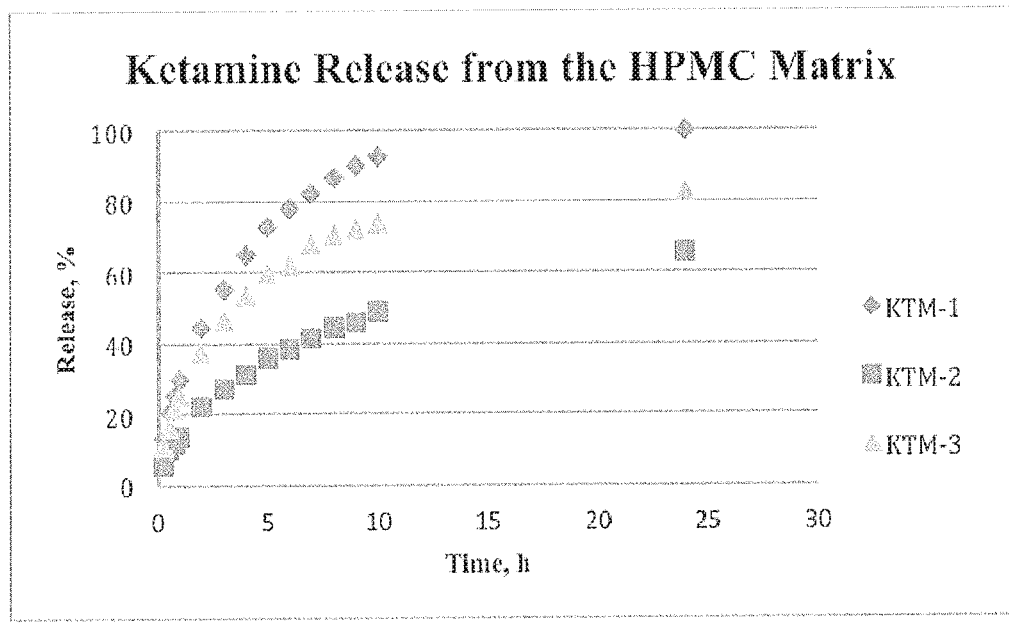
FIG. 1 is a graphical depiction of the release profile of ketamine from an HPMC matrix, with and without polyacrylic acid (compositions KTM-1 through KTM-3)

FIG. 6 relates to a rat liver homogenate metabolic assay comparing the half-life of norketamine and deuterated norketamine compounds 11 and 12; and FIG. 7 relates to pharmacokinetic (PK) data in rats of norketamine and a bis-deuterated norketamine compound 11.

V. DETAILED DESCRIPTION OF THE INVENTION

The market for ketamine for the treatment of conditions such as pain or depression, or use in migraine (e.g. with aura), refractory asthma, alcohol dependence, epilepsy, brain injury and/or stroke, has been largely focused on injections or infusion administration mainly due to the consequences of exceeding certain plasma concentrations, beyond which serious neurological side effects result. Tablet or capsule formulations of ketamine have generally failed commercially due to the relatively short therapeutic window of orally administered ketamine, which requires an oral administration of multiple daily doses of the drug; and the increased likelihood of exceeding psychotomimetic toxic plasma concentrations of ketamine. And although sustained release formulations have been generally considered for essentially all drugs, it is the implementation of this formulation that takes inventive contribution, and has yet to be achieved for ketamine. Such evidence could not be clearer than from the large commercial need that remains in the market.

In this regard, current professionals are eager for alternatives to ketamine intravenous infusion for 24-hour therapeutically effective plasma concentration profile, while seeking to utilize the long-studied and predictable nature of ketamine, as a therapeutic. However, even intricate, stratified tablets of other NMDA receptor antagonists such as dextromethorphan or amantadine that offer delayed release of a core material subsequent to the release of a separately formulated outer layer have not been able to achieve the release of an NMDA receptor antagonist for periods greater than 12 hours.

As confirmation, several common matrixes of the inactive pharmaceutical ingredients known in the art for the efficient controlled release were tested, and were unable to achieve 24 hour release profile. Using a controlled release matrix comprised of the hydroxypropyl methylcellulose and starch, a complete release of ketamine was observed in about 12 hours. Further, in the lipid-based matrices containing as much as 20% of Compritol ATO 888 (Glycerol behenate, Gattesfosse), ketamine could not be retained for more than 4-6 hours.

However, in order to maintain a therapeutically effective drug concentration in a once-a-day application analogous to the ketamine infusion, but which is more convenient for the patient care, ketamine and/or norketamine release should approach 12 to 24 hours, and in a manner that does not afford spikes in ketamine and/or norketamine plasma concentration. As such, the present invention provides oral, modified-release neuro-attenuating ketamine (NAKET) formulations and/or oral, modified-release neuro-attenuating norketamine (NANKET) formulations, methods of treatment, and methods of administration, which ensure the steady release of a therapeutically effective concentration of ketamine and/or norketamine from an oral modified-release pharmaceutical composition, without causing sedative or psychotomimetic toxic spikes in ketamine and/or norketamine plasma concentration.

In particular, the present invention provides an oral, modified-release formulation of a NAKET compound, including ketamine, e.g., a single layer tablet formulation. In certain specific embodiments, the oral, modified-release NAKET formulations, and methods of administration, provide steady administration of NAKET to a subject for 12 hours or greater, for example, 24 hours or greater, for example, up to 36 hours, after a single administration event, e.g., oral administration of a designated amount of the formulation, whether in one pill, or multiple pills.

In another particular aspect, the present invention provides an oral, modified-release formulation of a NANKET compound, including norketamine, e.g., a single layer tablet formulation. In certain specific embodiments, the oral, modified-release NANKET formulations, and methods of administration, provide steady administration of NANKET to a subject for 12 hours or greater, for example, 24 hours or greater, for example, up to 36 hours, after a single administration event, e.g., oral administration of a designated amount of the modified-release formulation, whether in one pill, or multiple pills. In certain embodiments, however, reduction of this therapeutic window may be desirable in order to achieve certain advantages for these NAKET and/or NANKET modified-release formulations, such as tamper resistance.

The present invention, including compounds, methods, and pharmaceutical compositions/formulations will be described with reference to the following definitions which, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

The language "and/or" is used herein as a shorthand notation to represent the expression "and," describing the combination of items, as well as "or," describing the items in the alternative form. For example, "ketamine and/or norketamine" is shorthand notation for the following: (1) ketamine and norketamine (i.e., both), and (2) ketamine or norketamine (i.e., either one).

The term "compound" when referring to a compound of this invention, refers to a collection or population of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will preferably be less than about 49.9% of the compound. In other embodiments, the relative amount of such isotopologues in toto will be less than about 47.5%, less than about 40%, less than about 32.5%, less than about 25%, less than about 17.5%, less than about 10%, less than about 5%, less than about 3%, less than about 1%, or less than about 0.5% of the compound.

As used herein, "isotopically enriched" refers to a compound that has been enriched synthetically with one or more heavy atom isotopes (e.g. deuterium). Because isotopic enrichment is not 100% effective, there can be impurities of the compound that are of lesser states of enrichment and these will have a lower mass. Likewise, because of over-enrichment (undesired enrichment) and because of natural isotopic abundance, there can be impurities of greater mass.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)-isomers, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-isomers maybe prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

The term "about", as used herein, means an acceptable margin of error for a particular value, which depends in part on how the value is measured or determined. In certain embodiments, "about" as used herein will be understood by persons of ordinary skill in the art to mean up to plus or minus 20% of the particular term. In further embodiments, "about" as used herein will be understood by persons of ordinary skill in the art to mean up to plus or minus 10% of the particular term.

The term "isolated" as used herein, means having been removed from or is free of other compounds or biological and/or chemical materials present when the compound is first formed. The term "isolated" embraces compounds isolated from natural sources as well as chemically-synthesized compounds.

As used herein, the term "substantially pure" means sufficiently homogeneous to appear free of readily detectable impurities as determined by standard analytical methods, such as thin layer chromatography (TLC), gel electrophoresis, high performance liquid chromatography (HPLC), nuclear magnetic resonance (NMR), and mass spectrometry (MS); or sufficiently pure such that further purification would not detectably alter the physical and chemical properties, or biological and pharmacological properties, such as enzymatic and biological activities, of the substance. In certain embodiments, "substantially pure" refers to a collection of molecules, wherein at least about 55%, about 60%, about 65%, about 70%, about 75%, about 80%, about 85%, about 90%, about 95%, about 97%, about 98%, about 98.5%, about 99%, about 99.5% or about 99.9% or greater of the molecules are a single compound, including a racemic mixture or a single stereoisomer thereof, as determined by standard analytical methods.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated terms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers,wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g, decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The term "ketamine," as used alone herein, is art-recognized, and is the common name for the molecule: (R,S)-2-(2-chlorophenyl)-2-(methylamino) cyclohexanone, or

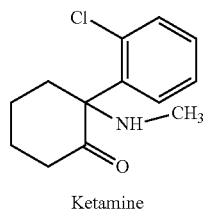 [SMILES: CNC1(c2ccccc2Cl)CCCCC1=O]

Ketamine

Ketamine is a well-known drug that is very water-soluble (e.g., solubility of the ketamine hydrochloride in water is about 200 mg/ml), and therefore has a high propensity to be rapidly released from a polymer matrix. The term "ketamine" is intended to include both racemic and enantiomerically enriched, e.g. enantiomerically pure, forms. In certain embodiments, the ketamine is racemic ketamine. In certain embodiments, the ketamine is enantiomerically enriched in one enantiomer. In particular embodiments, the ketamine is enriched in the S enantiomer. In particular embodiments, the ketamine is enriched in the R enantiomer.

The term "norketamine," as used alone herein, is art-recognized and is the common name for the molecule: (R,S)-2-(2-chlorophenyl)-2-(amino) cyclohexanone, or

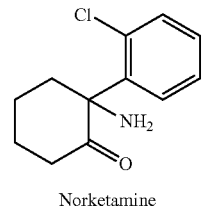 [SMILES: NC1(c2ccccc2Cl)CCCCC1=O]

Norketamine

Norketamine is a metabolic product of the demethylation of ketamine, and is considered by many to be active and show clearance similar, but somewhat slower, to that of ketamine; such activity, however, has been shown to be significantly reduced (roughly one third) as compared with ketamine. The term "norketamine" is intended to include both racemic and enantiomerically enriched, e.g. enantiomerically pure, forms. In certain embodiments, the norketamine is racemic ketamine. In certain embodiments, the norketamine is enantiomerically enriched in one enantiomer. In particular embodiments, the norketamine is enriched in the S enantiomer. In particular embodiments, the norketamine is enriched in the R enantiomer.

As used herein, the language "maximum sustained release" describes the release window for certain formulations of the present invention formulated to increase the release period to a maximum value, which is ultimately limited by the time the gastrointestinal tract naturally excretes all drugs with food.

The language "tamper resistance" is art-recognized to describe aspects of a drug formulation that make it more difficult to use the formulation to abuse the drug moiety of the formulation through extraction for intravenous use, or crushing for freebase use; and therefore reduce the risk for abuse of the drug.

As used herein, the term "steady" describes the stable or steady-state level of a molecule concentration, e.g., ketamine concentration.

As used herein the term "synthetic" or "synthetically" refers to a compound or composition as described herein that is not naturally occurring and that is produced artificially, e.g., via chemical synthesis. A "synthetic" compound or composition as described herein would not include an in vivo-produced compound or metabolite of an administered compound or agent.

As used herein, the term "composition" is equivalent to the term "formulation."

As used herein, the language "administration event" describes the administration of a subject a given dose, in the form of one or more pills within a short window of time, e.g., less than 10 minutes.

As used herein, the language "release period" describes the time window in which the neuro-attenuating ketamine is released from the matrix to afford plasma concentrations of ketamine and norketamine. The start time of the release period is defined from the point of oral administration to a subject, which is considered nearly equivalent to entry into the stomach, and initial dissolution by gastric enzymes and acid.

As used herein, and unless otherwise specified, the terms "treat," "treating" and "treatment" refer to the eradication or amelioration of a disease, disorder, or condition, or of one or more symptoms associated with the disease, disorder or condition. In certain embodiments, the terms refer to minimizing the advancement or worsening of the disease, disorder, or condition resulting from the administration of a formulation of the invention to a patient with such a disease, disorder, or condition. In some embodiments, the terms refer to the administration of a formulation provided herein, after the onset of symptoms of the particular disease, disorder, or condition. The terms "treat," "treating", "treatment", or the like, as used herein covers the treatment of a disease, disorder, or condition in a subject, e.g., a mammal, and includes at least one of: (i) inhibiting the disease, disorder, or condition, i.e., partially or completely halting its progression; (ii) relieving the disease, disorder, or condition, i.e. causing regression of symptoms of the disease, disorder, or condition, or ameliorating a symptom of the disease, disorder, or condition; and (iii) reversal or regression of the disease, disorder, or condition, preferably eliminating or curing of the disease, disorder, or condition. In a particular embodiment the terms "treat," "treating", "treatment", or the like, covers the treatment of a disease, disorder, or condition in a mammal, e.g., a primate, e.g., a human, and includes at least one of (i), (ii), and (iii) above. As is known in the art, adjustments for age, body weight, general health, sex, diet, time of administration drug interaction and the severity of the condition may be necessary, and will be ascertainable with routine experimentation by one of ordinary skill in the art based on the invention described herein.

As used herein, the terms "subject", and "patient" are used interchangeably. The terms "subject" and "patient" refer to an animal (e.g., a bird such as a chicken, quail or turkey) or a mammal including non-primates (e.g., a cow, pig, horse, sheep, rabbit, guinea pig, rat, cat, dog, and mouse) and primates (e.g., a monkey, chimpanzee and a human). In a particular embodiment, the subject is a human.

As used herein, and unless otherwise specified, the terms "prevent," "preventing" and/or "prevention" refer to the prevention of the onset, recurrence or spread of a disease, disorder, or condition, or of one or more symptoms thereof. In certain embodiments, the terms refer to the administration of neuro-attenuating ketamine (NAKET), a neuro-attenuating norketamine (NANKET), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, to a subject, with or without other additional active compounds, prior to the onset of symptoms, particularly to patients at risk of a disease, disorder, or condition provided herein. The terms encompass the inhibition or reduction of a symptom of the particular disease, disorder, or condition. Subjects with familial history of a disease, disorder, or condition, in particular, are candidates for preventive regimens in certain embodiments. In addition, subjects who have a history of recurring symptoms are also potential candidates for the prevention. In this regard, the terms "prevent," "preventing" and/or "prevention" may be interchangeably used with the term "prophylactic treatment." In certain embodiments, the prevention is achieved by administration of a prophylactically effective amount of neuro-attenuating ketamine (NAKET), a neuro-attenuating norketamine (NANKET), or any of the compounds described herein (e.g., ketamine, norketamine, a compound according to any one of formulas (I), (I-A), (I-B), and (II), or any of the compounds described in Tables A-D, or in any of the Examples provided herein), or a pharmaceutically acceptable salt thereof, of the invention.

As used herein, and unless otherwise specified, a "therapeutically effective amount" or an "effective amount" of an active agent, e.g., neuro-attenuating ketamine (NAKET), neuro-attenuating norketamine (NANKET), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, is an amount sufficient to provide a therapeutic benefit in the treatment or management of a disease, disorder, or condition, or to delay or minimize one or more symptoms associated with the disease, disorder, or condition. A therapeutically effective amount of neuro-attenuating ketamine (NAKET) means an amount of neuro-attenuating ketamine (NAKET), alone or in combination with other therapies or compounds (e.g., NANKET), which provides a therapeutic benefit in the treatment or management of the disease, disorder or condition. Likewise, a therapeutically effective amount of any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, means an amount of any of the compounds described herein (e.g., a compound according to any one of formulas (I), (I-A), (I-B), and (II), or any of the compounds described in Tables A-D, or in any of the Examples provided herein) alone or in combination with other therapies or compounds (e.g., NANKET), which provides a therapeutic benefit in the treatment or management of the disease, disorder, or condition. The term "therapeutically effective amount" can encompass an amount that improves overall therapy, reduces or avoids symptoms or causes of disease, disorder, or condition, or enhances the therapeutic efficacy of another therapeutic agent. The therapeutically effective amount for a particular patient in need of such treatment can be determined by considering various factors, such as the condition treated, the overall health of the patient, method of administration, the severity of side-effects, and the like. For any compound described herein, the therapeutically effective amount can be initially determined from cell culture assays. Target concentrations will be those concentrations of active compound(s) that are capable of achieving the methods described herein, as measured using the methods described herein or known in the art. As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

As used herein, and unless otherwise specified, the terms "manage," "managing" and "management", are used interchangeably herein and refer to preventing or slowing the progression, spread or worsening of a disease, disorder, or condition, or of one or more symptoms thereof. Often, the beneficial effects that a subject derives from a prophylactic and/or therapeutic agent do not result in a cure of the disease, disorder, or condition. In this regard, the terms "manage," "managing" and/or "management", encompass treating a subject who had suffered from the particular disease, disorder, or condition in an attempt to prevent or minimize the recurrence of the disease, disorder, or condition.

As used herein, and unless otherwise specified, a "prophylactically effective amount" of an active agent, e.g., neuro-attenuating ketamine (NAKET), is an amount sufficient to prevent a disease, disorder, or condition, or prevent its recurrence. A prophylactically effective amount of neuro-attenuating ketamine (NAKET) means an amount of neuro-attenuating ketamine (NAKET), alone or in combination with other agents (e.g., NANKET), which provides a prophylactic benefit in the prevention of the disease. The term "prophylactically effective amount" can encompass an amount that improves overall prophylaxis or enhances the prophylactic efficacy of another prophylactic agent. Likewise, a prophylactically effective amount of any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, means an amount of any of the compounds described herein (e.g., a compound according to any one of formulas (I), (I-A), (I-B), and (II), or any of the compounds described in Tables A-D, or in any of the Examples provided herein) alone or in combination with other therapies or compounds (e.g., NANKET), which provides a prophylactic benefit in the prevention of the disease.

The language "neurologically toxic spikes" is used herein to describe spikes in plasma concentration of ketamine and/or norketamine following an administration event to a subject that would produce side-effects of sedation and/or psychotomimetic effects, e.g., hallucination, dizziness, and nausea; which can not only have immediate repercussions, but also adversely effect treatment compliance. In particular, ketamine side effects may become more pronounced at blood concentration levels above 300 ng/L.

"Patient" or "subject" or "subject in need thereof" refers to a living organism or animal diagnosed with, suffering from or prone to a disease, disorder or condition that can be treated by administration of an isolated and/or substantially pure, isotopically-enriched, neuro-attenuating norketamine compound, including a pharmaceutical composition formulated therewith, or a novel, oral, modified-release NAKET or NANKET pharmaceutical composition as provided herein. Non-limiting examples include humans, other mammals, bovines, rats, mice, dogs, monkeys, goat, sheep, cows, deer, and other non-mammalian animals. In some embodiments, a patient is human.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

II. Compounds Of The Invention

Given the well-known use of ketamine, and the discovery described herein that ketamine may be orally formulated to provide oral, modified-release, neuro-attenuating ketamine (NAKET) pharmaceutical formulations, e.g., with reduced neurological adverse effects as compared to existing oral formulations, methods and the NAKET formulations of the present invention may comprise ketamine, or certain derivatives thereof. Further based on this collective understanding, relating to ketamine, ketamine derivatives, and formulations thereof described herein to provide NAKET, the present invention also provides for the use of norketamine for administration alone or in combination with other agents (e.g., including NAKET) as neuro-attenuating norketamine (NANKET), and considers certain norketamine derivatives advantageous for administration in these NANKET formulations.

Accordingly, the present invention provides methods and formulations of the present invention that may comprise ketamine and/or norketamine, or derivatives thereof, and of any of the compounds described herein (e.g., a compound according to any one of formulas (I), (I-A), (I-B), and (II), or any of the compounds described in Tables A-D, or in any of the Examples provided herein), or a pharmaceutically acceptable salt thereof. In certain embodiments, the ketamine or norketamine, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, may be derivatized in any manner that does not significantly effect formulation as described herein, or the ability of the ketamine/norketamine to achieve the desired therapeutic effects described herein, i.e., with similar steady release of a therapeutically effective concentration (e.g., based on indication) of the ketamine/norketamine derivative from an oral, modified-release pharmaceutical formulation without causing sedative or-psychotomimetic toxic spikes in the ketamine or norketamine derivative plasma concentration.

In certain embodiments of the present invention, the ketamine, norketamine, or derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, is enantiomerically enriched, e.g. enantiomerically pure, in one enantiomer. In specific embodiments, the ketamine and/or norketamine, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, is enriched in the S enantiomer (e.g., the carbon marked by "*" in any of formulas (I), (I-A), and (I-B) has the S-configuration e.g., S-norketamine.

A. Deuterated Derivatives

In a particular embodiment of the invention the derivative may be a deuterated derivative. For example, the ketamine or norketamine may be deuterated with one deuterium atom. In certain embodiments, the ketamine or norketamine may be deuterated with two deuterium atoms. In certain embodiments, the ketamine or norketamine may be deuterated with three deuterium atoms. In certain embodiments, the ketamine or norketamine may be deuterated with more than three deuterium atoms.

In the compounds of the present invention any atom not specifically designated as a particular isotope, e.g., deuterium, is meant to represent any stable isotope of that atom unless otherwise stated. Unless otherwise stated, when a position is designated specifically as "H" or "hydrogen", the position is understood to have hydrogen at its natural abundance isotopic composition. It will be recognized that some variation of natural isotopic abundance occurs in a synthesized compound depending upon the origin of chemical materials used in the synthesis. Thus, a preparation of a particular compound will inherently contain small amounts of deuterated and/or $^{13}$C-containing isotopologues. The concentration of such naturally abundant stable hydrogen and carbon isotopes, notwithstanding this variation, is small and immaterial as compared to the degree of stable isotopic substitution of compounds of this invention. See, for instance, Wada E et al, Seikagaku 1994, 66:15; Ganes L Z et al., Comp Biochem Physiol Mol lntegr Physiol 1998, 119:725. In a compound of this invention, when a particular position is designated as having deuterium, it is understood that the abundance of deuterium at that position is substantially greater than the natural abundance of deuterium, which is about 0.015%. Positions designated as having deuterium typically have a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope. In certain embodiments, a compound of this invention has an isotopic enrichment factor for each designated deuterium atom of at least about 3500 (52.5% deuterium incorporation at each designated deuterium atom), at least about 4000 (60% deuterium incorporation), at least 4500 (67.5% deuterium incorporation), at least about 5000 (75% deuterium incorporation), at least 5500 (82.5% deuterium incorporation), at least about 6000 (90% deuterium incorporation), at least about 6333.3 (95% deuterium incorporation), at least about 6466.7 (97% deuterium incorporation), at least about 6600 (99% deuterium incorporation), or at least about 6633.3 (99.5% deuterium incorporation).

In certain embodiments, each atom not specified as deuterium in any of the compounds of the instant invention is present at its natural isotopic abundance.

i. Deuterated Norketamine and Related Compounds

Given the present disclosure and insight, deuterated norketamine is particularly attractive for clinical applications due to the kinetic deuterium isotope effect, which would lead to decreased metabolic oxidation rates of these species. Such in vivo metabolic transformations of norketamine are mediated by the CYP enzymes and take place in significant part on the cyclohexanone part of the molecule by dehydrogenation, hydroxylation and glucuronidation of the hydroxylated derivatives. However, some metabolites originate from hydrogenation of the aryl ring. In general, the deuterium isotope effect, along with the formulations of the present invention offer very advantageous therapies for uses in the methods described herein.

In one aspect, the invention features a neuro-attenuating norketamine (NANKET) compound, or a pharmaceutically acceptable salt thereof.

In one aspect, the invention features a purified neuro-attenuating norketamine (NANKET) compound, or a pharmaceutically acceptable salt thereof.

In another aspect, the invention features an isotopically-enriched neuro-attenuating norketamine (NANKET) compound, or a pharmaceutically acceptable salt thereof, as described herein.

In one aspect, the invention features a purified, isotopically-enriched neuro-attenuating norketamine (NANKET) compound, or a pharmaceutically acceptable salt thereof, as described herein.

In still another aspect, the invention features a formulation comprising neuro-attenuating norketamine (NANKET) compound, or a pharmaceutically acceptable salt thereof, as described herein.

In another aspect, the invention features a composition comprising a neuro-attenuating norketamine (NANKET) compound, or a pharmaceutically acceptable salt thereof, as described herein.

In another aspect, the invention features a pharmaceutically acceptable salt of a neuro-attenuating norketamine (NANKET) compound, or a pharmaceutically acceptable salt thereof, as described herein.

In another aspect, the invention features an isolated neuro-attenuating norketamine (NANKET) compound, or a pharmaceutically acceptable salt thereof.

In another aspect, the invention features an istopically-enriched (e.g., a deuterium-enriched) neuro-attenuating norketamine (NANKET) compound, or a pharmaceutically acceptable salt thereof.

In another aspect, the invention features a synthetic composition of matter comprising a neuro-attenuating norketamine (NANKET) compound, or a pharmaceutically acceptable salt thereof.

In another aspect, the invention features a synthetic composition of matter comprising an istopically-enriched (e.g., a deuterium-enriched) neuro-attenuating norketamine (NANKET) compound, or a pharmaceutically acceptable salt thereof.

In another aspect, the invention features a pharmaceutical composition for treating a subject diagnosed with, suffering from, or susceptible to a disease, disorder, or condition (e.g., such as those for which ketamine treatment may be indicated), wherein the subject is in need of the treatment, said pharmaceutical composition comprising:
  (a) a neuro-attenuating norketamine (NANKET) compound, or a pharmaceutically acceptable salt thereof, as described herein; and
  (b) a pharmaceutically acceptable excipient.

In still another aspect, the invention features a pharmaceutical composition comprising
  (a) a neuro-attenuating norketamine (NANKET) compound, or a pharmaceutically acceptable salt thereof, as described herein; and
  (b) a pharmaceutically acceptable excipient.

In another aspect, the invention features a method of treating a subject diagnosed with, suffering from, or susceptible to a disease, disorder, or condition (e.g., those for which ketamine treatment may be indicated), the method comprising administering to the subject neuro-attenuating norketamine (NANKET) compound as described herein, or a pharmaceutically acceptable salt thereof, in an effective amount for treating, preventing, and/or managing the disease, disorder, or condition.

In one aspect, the invention features a compound of formula (I), or a pharmaceutically acceptable salt thereof.

In one aspect, the invention features a purified compound of formula (I), or a pharmaceutically acceptable salt thereof.

In another aspect, the invention features an isotopically-enriched compound of formula (I), or a pharmaceutically acceptable salt thereof, as described herein.

In one aspect, the invention features a purified, isotopically-enriched compound of formula (I), or a pharmaceutically acceptable salt thereof, as described herein.

In still another aspect, the invention features a formulation comprising a compound of formula (I), or a pharmaceutically acceptable salt thereof, as described herein.

In another aspect, the invention features a composition comprising a compound of formula (I), or a pharmaceutically acceptable salt thereof, as described herein.

In another aspect, the invention features a pharmaceutically acceptable salt of a compound of formula (I), or a pharmaceutically acceptable salt thereof, as described herein.

In another aspect, the invention features an isolated compound of formula (I), or a pharmaceutically acceptable salt thereof.

In another aspect, the invention features an istopically-enriched (e.g., a deuterium-enriched) compound of formula (I), or a pharmaceutically acceptable salt thereof.

In another aspect, the invention features a synthetic composition of matter comprising a compound of formula (I), or a pharmaceutically acceptable salt thereof.

In another aspect, the invention features a synthetic composition of matter comprising an istopically-enriched (e.g., a deuterium-enriched) compound of formula (I), or a pharmaceutically acceptable salt thereof.

In another aspect, the invention features a pharmaceutical composition for treating subject diagnosed with, suffering from, or susceptible to a disease, disorder, or condition (e.g., such as those for which ketamine treatment may be indicated), wherein the subject is in need of the treatment, said pharmaceutical composition comprising:
(c) a compound of formula (I), or a pharmaceutically acceptable salt thereof, as described herein; and
(d) a pharmaceutically acceptable excipient.

In still another aspect, the invention features a pharmaceutical composition comprising
(c) a compound of formula (I), or a pharmaceutically acceptable salt thereof, as described herein; and
(d) a pharmaceutically acceptable excipient.

In another aspect, the invention features a method of treating a subject diagnosed with, suffering from, or suspectible to a disease, disorder, or condition (e.g., those for which ketamine treatment may be indicated), the method comprising administering to the subject a compound of formula (I) as described herein, or a pharmaceutically acceptable salt thereof, in an effective amount for treating, preventing, and/or managing the disease, disorder, or condition.

In certain embodiments of the invention, the compound of formula (I) has the following structure,

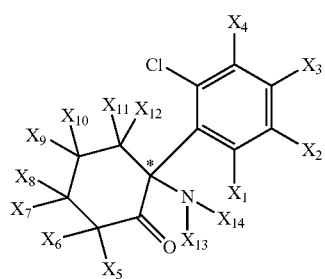

or a pharmaceutically acceptable salt thereof,
wherein
$X_1, X_2, X_3, X_4, X_5, X_6, X_7, X_8, X_9, X_{10}, X_{11}, X_{12}, X_{13}$ and $X_{14}$ are each independently selected from the group consisting of hydrogen and deuterium, and wherein at least one of $X_1, X_2, X_3, X_4, X_5, X_6, X_7, X_8, X_9, X_{10}, X_{11}, X_{12}, X_{13}$, and $X_{14}$ is deuterium.

In certain embodiments of formula (I), when each of $X_1$, $X_2$, $X_3$, and $X_4$ is deuterium, then at least one of $X_5$, $X_6$, $X_7$, $X_8$, $X_9$, $X_{10}$, $X_{11}$, $X_{12}$, $X_{13}$, and $X_{14}$ is deuterium.

In certain embodiments of formula (I), at least one of $X_5$, $X_6$, $X_7$, $X_8$, $X_9$, $X_{10}$, $X_{11}$, and $X_{12}$ is deuterium.

In certain embodiments of formula (I), $X_5, X_6, X_7, X_8, X_9$, $X_{10}, X_{11}$, and $X_{12}$ are deuterium. In further embodiments, $X_{13}$, and $X_{14}$ are deuterium.

In certain embodiments of formula (I), $X_5$ and $X_6$ are deuterium, $X_7$ and $X_8$ are deuterium, $X_9$ and $X_{10}$ are deuterium, and/or $X_{11}$ and $X_{12}$ are deuterium.

In certain embodiments of formula (I), $X_5$ and $X_6$ are deuterium. In certain embodiments of formula (I), $X_7$ and $X_8$ are hydrogen, $X_9$ and $X_{10}$ are hydrogen, and/or $X_{11}$ and $X_{12}$ are hydrogen. In further embodiments, each of $X_7, X_8, X_9$, $X_{10}, X_{11}, X_{12}, X_{13}$, and $X_{14}$ is hydrogen.

In certain embodiments of formula (I), $X_1, X_2, X_3, X_4$, are deuterium.

In certain embodiments of formula (I), $X_1, X_2, X_3, X_4$, are hydrogen

In certain embodiments of formula (I), $X_5, X_6, X_7, X_8$ are deuterium.

In certain embodiments of formula (I), $X_5, X_6, X_7$, and $X_8$ are hydrogen.

In certain embodiments of formula (I), $X_{13}$ and $X_{14}$ are deuterium.

In certain embodiments of formula (I), $X_{13}$ and $X_{14}$ are hydrogen.

In certain embodiments, the compound of formula (I) may be isolated.

In certain embodiments, the compound of formula (I) may be purified.

Accordingly, the present invention provides a composition enriched in the deuterated derivative over the non-deuterated analog.

In certain embodiments, the compound of formula (I) is isolated or purified, e.g., the compound of formula (I) is present at a purity of at least 50% by weight (e.g., at least about 55%, about 60%, about 65%, about 70%, about 75%, about 80%, about 85%, about 90%, about 95%, about 97%, about 98%, about 98.5%, about 99%, about 99.5% or about 99.9% or greater) of the total amount of isotopologues of formula (I) present. Thus, in particular embodiments, a composition comprising a compound of formula (I) includes a distribution of isotopologues of the compound, provided at least about 50% of the isotopologues by weight are the recited compound. In further embodiments, at least about 90%, about 95%, about 97%, about 98%, about 98.5%, about 99%, about 99.5% or about 99.9% or greater of the isotopologues by weight are the recited compound.

In certain embodiments, any position in the compound of formula (I) designated as being deuterium has a minimum deuterium incorporation of at least about 45% (e.g., at least about 52.5%, at least about 60%, at least about 67.5%, at least about 75%, at least about 82.5%, at least about 90%, at least about 95%, at least about 97%, at least about 99%, or at least about 99.5%) at the designated position(s) of the compound of formula (I), Thus, in particular embodiments, a composition comprising a compound of formula (I) includes a distribution of isotopologues of the compound, provided at least about 45% of the isotopologues include a D at the designated position(s). In further embodiments, at least about 90%, about 95%, about 97%, about 98%, about 98.5%, about 99%, about 99.5% or about 99.9% or greater of the isotopologues include a D at the designated position(s).

In certain embodiments, a compound of formula (I) is "substantially free of" other isotopologues of the compound. For example, less than about 50%, less than about 25%, less than about 10%, less than about 5%, less than about 2%, less than about 1%, or less than about 0.5% of other isotopologues are present.

The term "isotopologue" refers to a species that has the same chemical structure and formula as a specific compound of this invention, with the exception of the isotopic composition at one or more positions, e.g., H vs. D. Thus an isotopologue differs from a specific compound of this invention in the isotopic composition thereof.

In one aspect, the invention features a compound of formula (I-A) or (I-B), or a pharmaceutically acceptable salt thereof.

In one aspect, the invention features a purified compound of formula (I-A) or (I-B), or a pharmaceutically acceptable salt thereof.

In another aspect, the invention features an isotopically-enriched compound of formula (I-A) or (I-B), or a pharmaceutically acceptable salt thereof, as described herein.

In one aspect, the invention features a purified, isotopically-enriched compound of formula (I-A) or (I-B), or a pharmaceutically acceptable salt thereof, as described herein.

In still another aspect, the invention features a formulation comprising, compound of formula (I-A) or (I-B), or a pharmaceutically acceptable salt thereof, as described herein.

In another aspect, the invention features a composition comprising a compound of formula (I-A) or (I-B), or a pharmaceutically acceptable salt thereof, as described herein.

In another aspect, the invention a pharmaceutically acceptable salt of a compound of formula (I-A) or (I-B), or a pharmaceutically acceptable salt thereof, as described herein.

In still another aspect, the invention features a pharmaceutical composition comprising
(a) a compound of formula (I-A) or (I-B), or a pharmaceutically acceptable salt thereof, as described herein; and
(b) a pharmaceutically acceptable excipient.

In certain embodiments of the invention, the compound of formula (I-A) has the following structure, (I-A)

or a pharmaceutically acceptable salt thereof,
wherein
$X_1$, $X_2$, $X_3$, $X_4$, $X_6$, $X_7$, $X_8$, $X_9$, $X_{10}$, $X_{11}$, $X_{12}$, $X_{13}$, and $X_{14}$ are each independently selected from the group consisting of hydrogen and deuterium, and wherein at least one of $X_1$, $X_2$, $X_3$, $X_4$, $X_6$, $X_7$, $X_8$, $X_9$, $X_{10}$, $X_{11}$, $X_{12}$, $X_{13}$, and $X_{14}$ is deuterium.

In certain embodiments of formula (I-A), when each of $X_1$, $X_2$, $X_3$, and $X_4$ is deuterium, then at least one of $X_6$, $X_7$, $X_8$, $X_9$, $X_{10}$, $X_{11}$, $X_{12}$, $X_{13}$, and $X_{14}$ is deuterium.

In certain embodiments of formula (I-A), at least one of $X_6$, $X_7$, $X_8$, $X_9$, $X_{10}$, $X_{11}$, and $X_{12}$ is deuterium.

In certain embodiments of formula (I-A), $X_6$, $X_7$, $X_8$, $X_9$, $X_{10}$, $X_{11}$, and $X_{12}$ are deuterium. In further embodiments, $X_{13}$, and $X_{14}$ are deuterium.

In certain embodiments of formula (I-A), $X_6$ is deuterium, $X_7$ and $X_8$ are deuterium, $X_9$ and $X_{10}$ are deuterium, and/or $X_{11}$ and $X_{12}$ are deuterium.

In certain embodiments of formula (I-A), $X_6$ is deuterium. In certain embodiments of formula (I), $X_7$ and $X_8$ are hydrogen, $X_9$ and $X_{10}$ are hydrogen, and/or $X_{11}$ and $X_{12}$ are hydrogen. In further embodiments, each of $X_7$, $X_8$, $X_9$, $X_{10}$, $X_{11}$, $X_{12}$, $X_{13}$, and $X_{14}$ is hydrogen.

In certain embodiments of formula (I-A), $X_6$, $X_7$, and $X_8$ are deuterium.

In certain embodiments of formula (I-A), $X_6$, $X_7$, and $X_8$ are hydrogen.

In certain embodiments of the invention, the compound of formula (I-B) has the following structure, (I-B)

or a pharmaceutically acceptable salt thereof,
wherein
$X_1$, $X_2$, $X_3$, $X_4$, $X_6$, $X_8$, $X_9$, $X_{10}$, $X_{11}$, $X_{12}$, $X_{13}$, and $X_{14}$ are each independently selected from the group consisting of hydrogen and deuterium, and wherein at least one of $X_1$, $X_2$, $X_3$, $X_4$, $X_6$, $X_8$, $X_9$, $X_{10}$, $X_{11}$, $X_{12}$, $X_{13}$, and $X_{14}$ is deuterium.

In certain embodiments of formula (I-B), when each of $X_1$, $X_2$, $X_3$, and $X_4$ is deuterium, then at least one of $X_6$, $X_8$, $X_9$, $X_{10}$, $X_{11}$, $X_{12}$, $X_{13}$, and $X_{14}$ is deuterium.

In certain embodiments of formula (I-B), at least one of $X_6$, $X_8$, $X_9$, $X_{10}$, $X_{11}$, and $X_{12}$ is deuterium.

In certain embodiments of formula (I-B), $X_6$, $X_8$, $X_9$, $X_{10}$, $X_{11}$, and $X_{12}$ are deuterium. In further embodiments, $X_{13}$, and $X_{14}$ are deuterium.

In certain embodiments of formula (I-B), $X_6$ is deuterium, $X_8$ is deuterium, $X_9$ and $X_{10}$ are deuterium, and/or $X_{11}$ and $X_{12}$ are deuterium.

In certain embodiments of formula (I-B), $X_6$ is deuterium. In certain embodiments of formula (I), $X_8$ is hydrogen, $X_9$ and $X_{10}$ are hydrogen, and/or $X_{11}$ and $X_{12}$ are hydrogen. In further embodiments, each of $X_8$, $X_9$, $X_{10}$, $X_{11}$, $X_{12}$, $X_{13}$, and $X_{14}$ is hydrogen.

In certain embodiments of formula (I-B), $X_6$ and $X_8$ are deuterium.

In certain embodiments of formula (I-B), $X_6$ and $X_8$ are hydrogen.

In certain embodiments of formula (I-A) and/or (I-B), $X_1$, $X_2$, $X_3$, $X_4$, are deuterium.

In certain embodiments of formula (I-A) and/or (I-B), $X_1$, $X_2$, $X_3$, $X_4$, are hydrogen In certain embodiments of formula (I-A) and/or (I-B), $X_{13}$ and $X_{14}$ are deuterium.

In certain embodiments of formula (I-A) and/or (I-B), $X_{13}$ and $X_{14}$ are hydrogen.

In certain embodiments, the compound of formula (I-A) and/or (I-B) may be isolated.

In certain embodiments, the compound of formula (I-A) and/or (I-B) may be purified. Accordingly, the present invention provides a composition enriched in the deuterated derivative over the non-deuterated analog.

In certain embodiments, the compound of formula (I-A) and/or (I-B) is isolated or purified. For example, the compound of formula (I-A) is present at a purity of at least about 50% by weight (e.g., at least about 55%, about 60%, about 65%, about 70%, about about 75%, about 80%, about 85%, about 90%, about 95%, about 97%, about 98%, about 98.5%, about 99%, about 99.5% or about 99.9% or greater) of the total amount of isotopologues of formula (I-A) present, or the compound of formula (I-B) is present at a purity of at least about 50% by weight (e.g., at least about 55%, about 60%, about 65%, about 70%, about about 75%, about 80%, about 85%, about 90%, about 95%, about 97%, about 98%, about about 98.5%, about 99%, about 99.5% or about 99.9% or greater) of the total amount of isotopologues of formula (I-B) present. Thus, in particular embodiments, a composition comprising a compound of formula (I-A) and/or (I-B) includes a distribution of isotopologues of the compound, provided at least 50% of the isotopologues by weight are the recited compound. In some embodiments, at least about 90%, about 95%, about 97%, about 98%, about 98.5%, about 99%, about 99.5% or about 99.9% or greater of the isotopologues by weight are the recited compound of formula (I-A). In other embodiments, at least about 90%, about 95%, about 97%, about 98%, about 98.5%, about 99%, about 99.5% or about 99.9% or greater of the isotopologues by weight are the recited compound of formula (I-B).

In certain embodiments, any position in the compound of formula (I-A) designated as being deuterium has a minimum deuterium incorporation of at least about 45% (e.g., at least about 52.5%, at least about 60%, at least about 67.5%, at least about 75%, at least about 82.5%, at least about 90%, at least about 95%, at least about 97%, at least about 99%, or at least about 99.5% or greater) at the designated position(s) of the compound of formula (I-A). Thus, in particular embodiments, a composition comprising a compound of formula (I-A) includes a distribution of isotopologues of the compound, provided at least about 45% of the isotopologues include a D at the designated position(s). In further embodiments, at least about 90%, about 95%, about 97%, about 98%, about 98.5%, about about 99%, about 99.5% or about 99.9% or greater of the isotopologues include a D at the designated position(s).

In certain embodiments, any position in the compound of formula (I-B) designated as being deuterium has a minimum deuterium incorporation of at least about 45% (e.g., at least about 52.5%, at least about 60%, at least about 67.5%, at least about 75%, at least about about 82.5%, at least about 90%, at least about 95%, at least about 97%, at least about 99%, or at least about 99.5% or greater) at the designated position(s) of the compound of formula (I-B). Thus, in particular embodiments, a composition comprising a compound of formula (I-B) includes a distribution of isotopologues of the compound, provided at least about 45% of the isotopologues include a D at the designated position(s). In further embodiments, at least about 90%, about 95%, about 97%, about 98%, about 98.5%, about about 99%, about 99.5% or about 99.9% or greater of the isotopologues include a D at the designated position(s).

In certain embodiments, a compound of formula (I-A) and/or (I-B) is "substantially free of" other isotopologues of the compound. For example, less than about 50%, less than about 25%, less than about 10%, less than about 5%, less than about 2%, less than about 1%, or less than about 0.5% of other isotopologues are present.

Exemplary compounds according to formula (I), (I-A), and (I-B) are provided in Tables A-D below.

TABLE A

Exemplary Compounds of Formula (I)

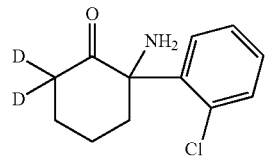 [SMILES: [2H]C1([2H])CCCC(N)(c2ccccc2Cl)C1=O]
11

TABLE A-continued

Exemplary Compounds of Formula (I)

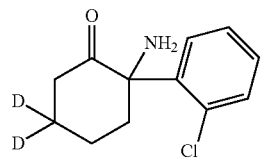 [SMILES: [2H]C1([2H])CCC(N)(c2ccccc2Cl)C(=O)C1]
13

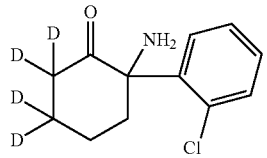
14

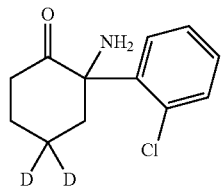 [SMILES: [2H]C1([2H])CCC(=O)C(N)(c2ccccc2Cl)C1]
15

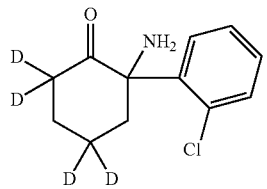 [SMILES: [2H]C1([2H])CC([2H])([2H])C(=O)C(N)(c2ccccc2Cl)C1]
16

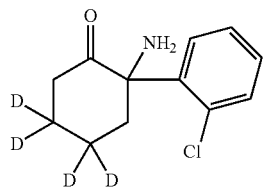 [SMILES: [2H]C1([2H])CC(=O)C(N)(c2ccccc2Cl)CC1([2H])[2H]]
17

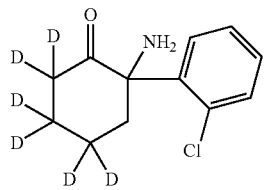 [SMILES: [2H]C1([2H])CC(N)(c2ccccc2Cl)C(=O)C([2H])([2H])C1([2H])[2H]]
18

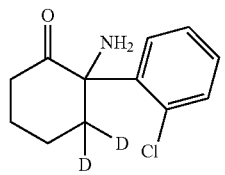 [SMILES: [2H]C1([2H])CCCC(=O)C1(N)c1ccccc1Cl]
19

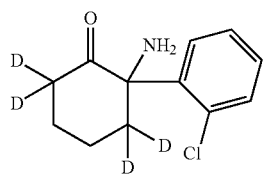 [SMILES: [2H]C1([2H])CCC([2H])([2H])C(N)(c2ccccc2Cl)C1=O]
20

TABLE A-continued
Exemplary Compounds of Formula (I)
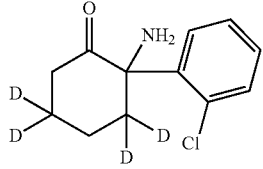 [SMILES: [2H]C1([2H])CC(=O)C(N)(c2ccccc2Cl)C([2H])([2H])C1]
21
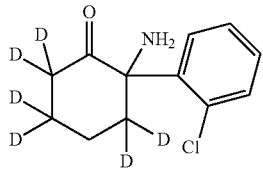 [SMILES: [2H]C1([2H])CC([2H])([2H])C(N)(c2ccccc2Cl)C(=O)C1([2H])[2H]]
22
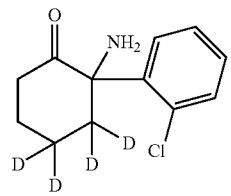
23
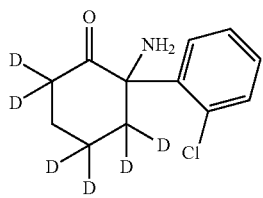 [SMILES: [2H]C1([2H])CC([2H])([2H])C([2H])([2H])C(N)(c2ccccc2Cl)C1=O]
24
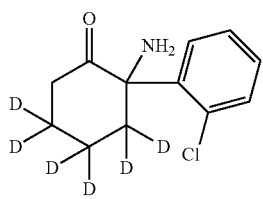 [SMILES: [2H]C1([2H])CC(=O)C(N)(c2ccccc2Cl)C([2H])([2H])C1([2H])[2H]]
25
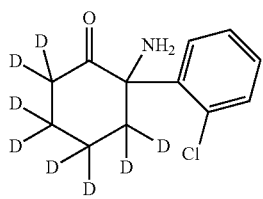 [SMILES: [2H]C1([2H])C(=O)C(N)(c2ccccc2Cl)C([2H])([2H])C([2H])([2H])C1([2H])[2H]]
26
TABLE B
Exemplary Compounds of Formula (I)
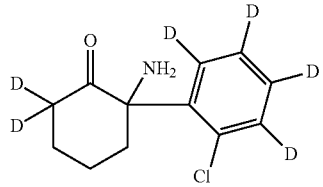 [SMILES: [2H]c1c([2H])c([2H])c(C2(N)CCCC([2H])([2H])C2=O)c(Cl)c1[2H]]
27
TABLE B-continued
Exemplary Compounds of Formula (I)
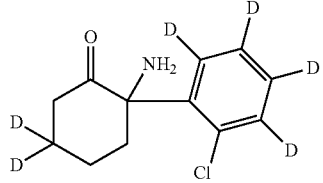 [SMILES: [2H]c1c([2H])c([2H])c(C2(N)CCC([2H])([2H])CC2=O)c(Cl)c1[2H]]
28
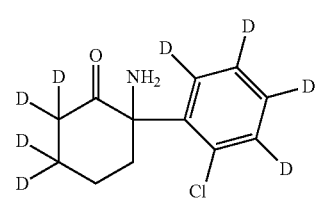 [SMILES: [2H]c1c([2H])c([2H])c(C2(N)CCC([2H])([2H])C([2H])([2H])C2=O)c(Cl)c1[2H]]
29
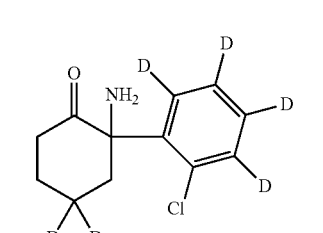
30
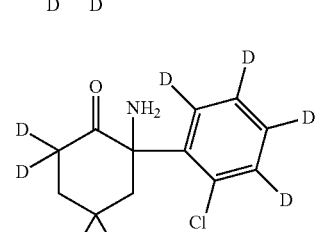
31
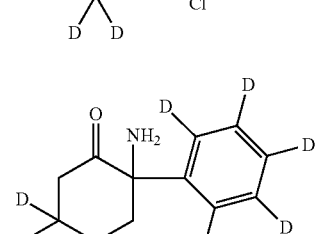
32
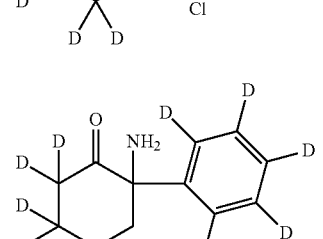
33
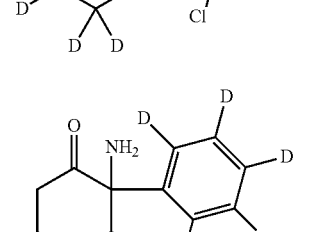
34

TABLE B-continued
Exemplary Compounds of Formula (I)
35
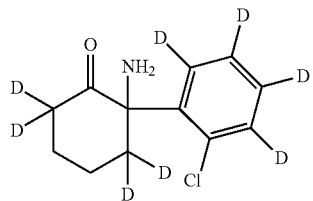 [SMILES: [2H]c1c([2H])c([2H])c(C2(N)C(=O)C([2H])([2H])CCC2([2H])[2H])c(Cl)c1[2H]]
36
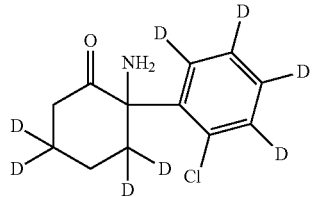 [SMILES: [2H]c1c([2H])c([2H])c(C2(N)C(=O)CC([2H])([2H])CC2([2H])[2H])c(Cl)c1[2H]]
37
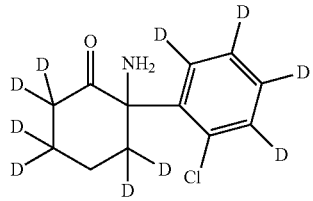 [SMILES: [2H]c1c([2H])c([2H])c(C2(N)C(=O)C([2H])([2H])C([2H])([2H])CC2([2H])[2H])c(Cl)c1[2H]]
38
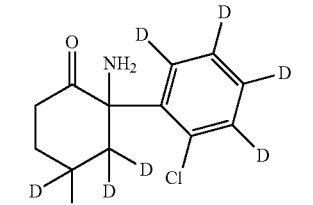
39
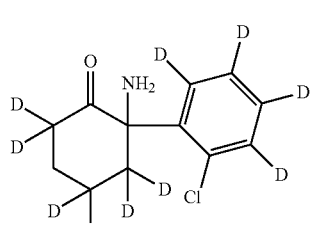
40
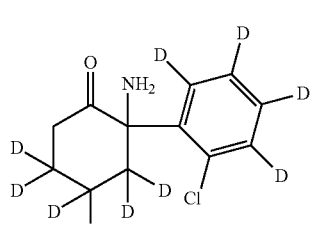
41
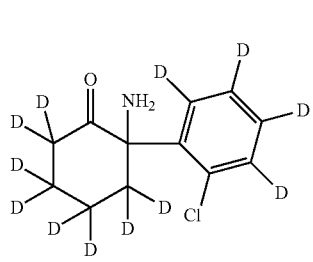 [SMILES: [2H]c1c([2H])c([2H])c(C2(N)C(=O)C([2H])([2H])C([2H])([2H])C([2H])([2H])C2([2H])[2H])c(Cl)c1[2H]]
TABLE C
Exemplary Compounds of Formula (I-A)
42
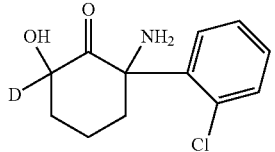 [SMILES: [2H]C1(O)CCCC(N)(c2ccccc2Cl)C1=O]
43
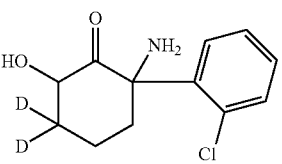 [SMILES: [2H]C1([2H])CCC(N)(c2ccccc2Cl)C(=O)C1O]
44
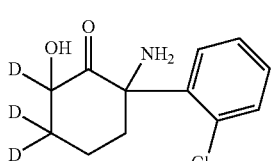
45
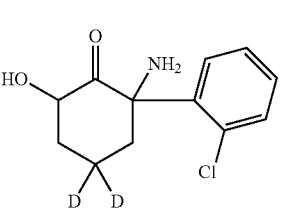 [SMILES: [2H]C1([2H])CC(O)C(=O)C(N)(c2ccccc2Cl)C1]
46
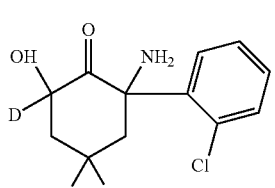
47
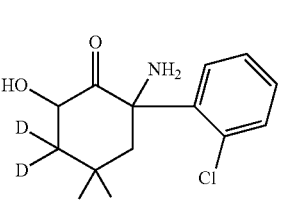
48
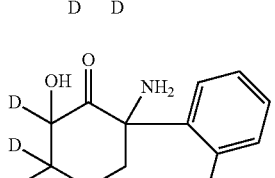
49
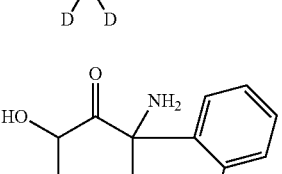
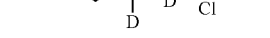

TABLE C-continued
Exemplary Compounds of Formula (I-A)
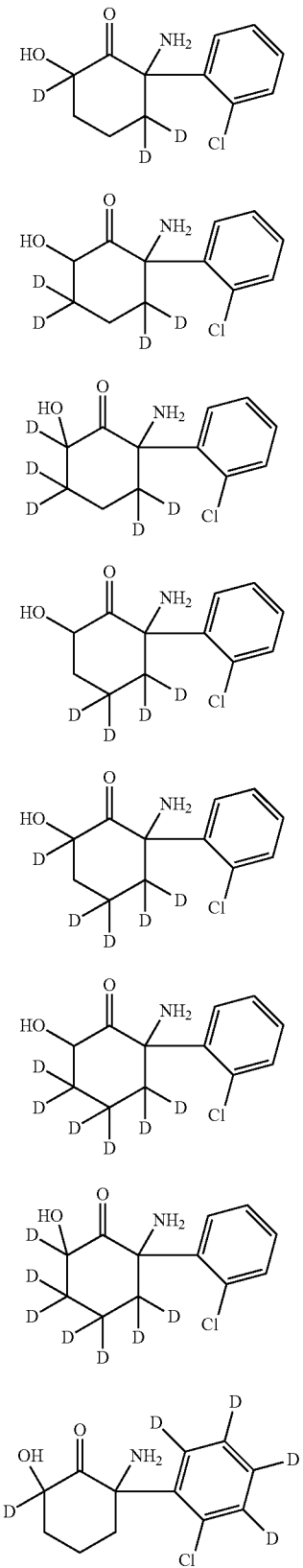
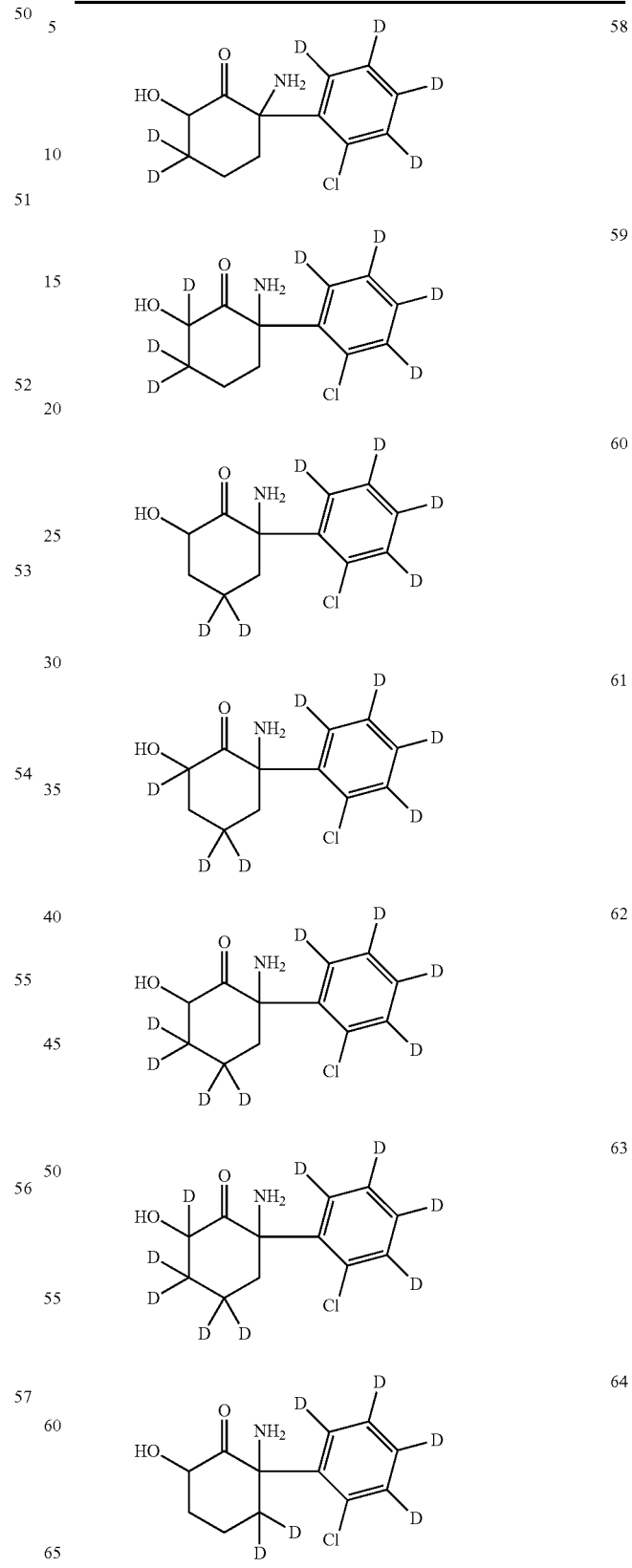

TABLE C-continued

Exemplary Compounds of Formula (I-A)

TABLE D

Exemplary Compounds of Formula (I-B)

TABLE D-continued
Exemplary Compounds of Formula (I-B)
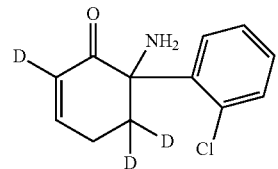 [SMILES: [2H]C1=CCC([2H])([2H])C(N)(c2ccccc2Cl)C1=O]
80
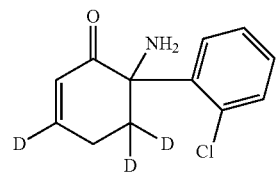 [SMILES: [2H]C1=CC(=O)C(N)(c2ccccc2Cl)C([2H])([2H])C1]
81
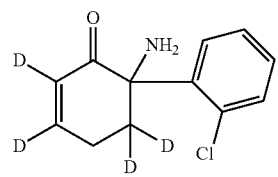 [SMILES: [2H]C1=C([2H])C(=O)C(N)(c2ccccc2Cl)C([2H])([2H])C1]
82
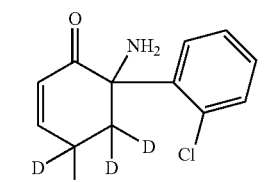
83
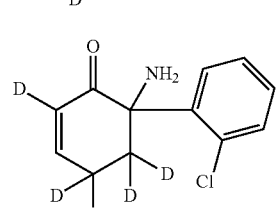
84
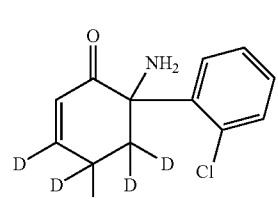
85
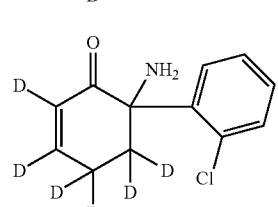
86
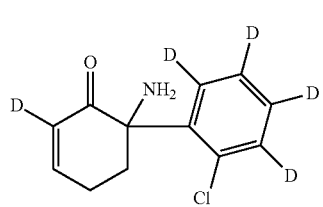 [SMILES: [2H]C1=CCCC(N)(c2c([2H])c([2H])c([2H])c([2H])c2Cl)C1=O]
87
TABLE D-continued
Exemplary Compounds of Formula (I-B)
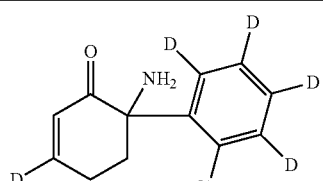
88
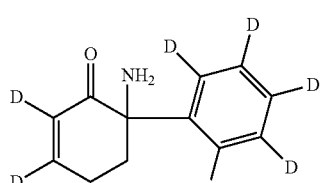
89
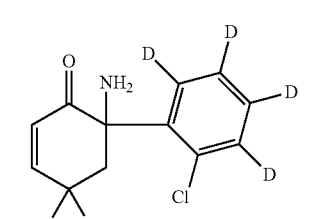
90
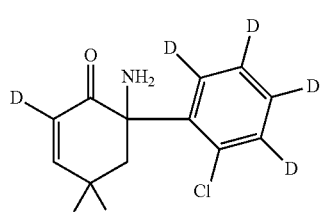
91
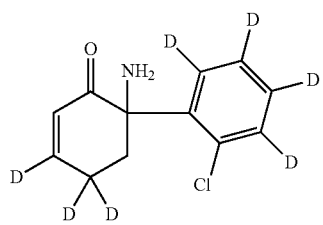 [SMILES: [2H]C1=CC(=O)C(N)(c2c([2H])c([2H])c([2H])c([2H])c2Cl)CC1([2H])[2H]]
92
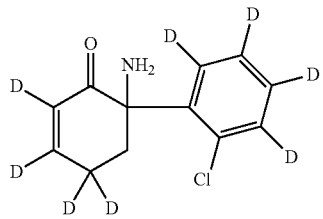 [SMILES: [2H]C1=C([2H])C([2H])([2H])CC(N)(c2c([2H])c([2H])c([2H])c([2H])c2Cl)C1=O]
93
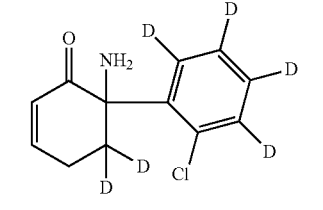 [SMILES: [2H]c1c([2H])c([2H])c(C2(N)C(=O)C=CCC2([2H])[2H])c(Cl)c1[2H]]
94

TABLE D-continued

Exemplary Compounds of Formula (I-B)

95
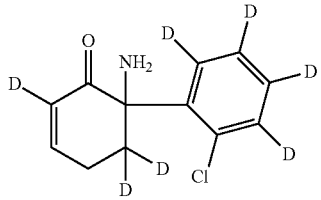 [SMILES: [2H]C1=CCC([2H])([2H])C(N)(c2c([2H])c([2H])c([2H])c([2H])c2Cl)C1=O]

96
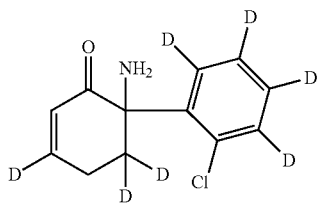 [SMILES: [2H]C1=CC(=O)C(N)(c2c([2H])c([2H])c([2H])c([2H])c2Cl)C([2H])([2H])C1]

97
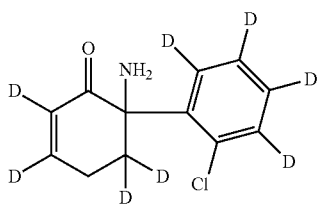 [SMILES: [2H]C1=C([2H])C(=O)C(N)(c2c([2H])c([2H])c([2H])c([2H])c2Cl)C([2H])([2H])C1]

98
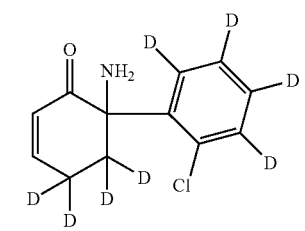 [SMILES: [2H]c1c([2H])c([2H])c(C2(N)C(=O)C=CC([2H])([2H])C2([2H])[2H])c(Cl)c1[2H]]

99
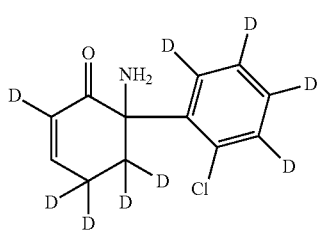 [SMILES: [2H]C1=CC([2H])([2H])C([2H])([2H])C(N)(c2c([2H])c([2H])c([2H])c([2H])c2Cl)C1=O]

100
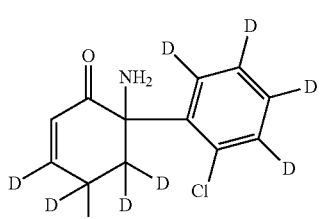

101
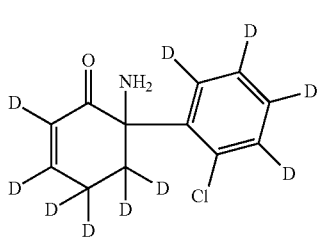 [SMILES: [2H]C1=C([2H])C([2H])([2H])C([2H])([2H])C(N)(c2c([2H])c([2H])c([2H])c([2H])c2Cl)C1=O]

ii. Deuterated Ketamine

In one aspect, the invention features a neuro-attenuating ketamine (NAKET) compound, or a pharmaceutically acceptable salt thereof.

In one aspect, the invention features a purified neuro-attenuating ketamine (NAKET) compound, or a pharmaceutically acceptable salt thereof.

In another aspect, the invention features an isotopically-enriched neuro-attenuating ketamine (NAKET) compound, or a pharmaceutically acceptable salt thereof, as described herein.

In one aspect, the invention features a purified, isotopically-enriched neuro-attenuating ketamine (NAKET) compound, or a pharmaceutically acceptable salt thereof, as described herein.

In still another aspect, the invention features a formulation comprising neuro-attenuating ketamine (NAKET) compound, or a pharmaceutically acceptable salt thereof, as described herein.

In another aspect, the invention features a composition comprising a neuro-attenuating ketamine (NAKET) compound, or a pharmaceutically acceptable salt thereof, as described herein.

In another aspect, the invention features a pharmaceutically acceptable salt of a neuro-attenuating ketamine (NAKET) compound, or a pharmaceutically acceptable salt thereof, as described herein.

In another aspect, the invention features an isolated neuro-attenuating ketamine (NAKET) compound, or a pharmaceutically acceptable salt thereof.

In another aspect, the invention features an istopically-enriched (e.g., deuterium-enriched) neuro-attenuating ketamine (NAKET) compound, or a pharmaceutically acceptable salt thereof.

In another aspect, the invention features a synthetic composition of matter comprising a neuro-attenuating ketamine (NAKET) compound, or a pharmaceutically acceptable salt thereof.

In another aspect, the invention features a synthetic composition of matter comprising an istopically-enriched (e.g., a deuterium-enriched) neuro-attenuating ketamine (NAKET) compound, or a pharmaceutically acceptable salt thereof.

In another aspect, the invention features a pharmaceutical composition for treating a subject diagnosed with, suffering from, or suspectible to a disease, disorder, or condition (e.g., such as those for which ketamine treatment may be indicated), wherein the subject is in need of the treatment, said pharmaceutical composition comprising:

(a) a neuro-attenuating ketamine (NAKET) compound, or a pharmaceutically acceptable salt thereof, as described herein; and (b) a pharmaceutically acceptable excipient.

In still another aspect, the invention features a pharmaceutical composition comprising (a) a neuro-attenuating ketamine (NAKET) compound, or a pharmaceutically acceptable salt thereof, as described herein; and (b) a pharmaceutically acceptable excipient.

In another aspect, the invention features a method of treating a subject diagnosed with, suffering from, or suspectible to a disease, disorder, or condition (e.g., those for which ketamine treatment may be indicated), the method comprising administering to the subject neuro-attenuating ketamine (NAKET) compound as described herein, or a pharmaceutically acceptable salt thereof, in an effective amount for treating, preventing, and/or managing the disease, disorder, or condition.

In one aspect, the invention features a compound of formula (II), or a pharmaceutically acceptable salt thereof.

In one aspect, the invention features a purified compound of formula (II), or a pharmaceutically acceptable salt thereof.

In another aspect, the invention features an isotopically-enriched compound of formula (II), or a pharmaceutically acceptable salt thereof, as described herein.

In one aspect, the invention features a purified, isotopically-enriched compound of formula (II), or a pharmaceutically acceptable salt thereof, as described herein.

In still another aspect, the invention features a formulation comprising a compound of formula (II), or a pharmaceutically acceptable salt thereof, as described herein.

In another aspect, the invention features a composition comprising a compound of formula (II), or a pharmaceutically acceptable salt thereof, as described herein.

In another aspect, the invention a pharmaceutically acceptable salt of a compound of formula (II), or a pharmaceutically acceptable salt thereof, as described herein.

In still another aspect, the invention features a pharmaceutical composition comprising
(a) a compound of formula formula (II), or a pharmaceutically acceptable salt thereof, as described herein; and
(b) a pharmaceutically acceptable excipient.

In certain embodiments of the invention, the compound of formula (II) has the following structure:

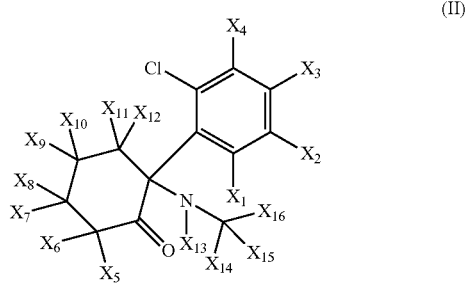

wherein
$X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, and $X_{16}$ are each independently selected from the group consisting of hydrogen and deuterium, and wherein at least one of $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, and $X_{16}$ is deuterium.

In certain embodiments of formula (II), $X_5$, $X_6$, $X_7$, $X_8$, $X_9$, $X_{10}$, $X_{11}$, and $X_{12}$ are deuterium.

In certain embodiments of formula (II), $X_{14}$, $X_{15}$, and $X_{16}$ are deuterium. In certain embodiments of formula (II), $X_{14}$, $X_{15}$, and $X_{16}$ are hydrogen.

In certain embodiments of formula (II), $X_{13}$ is hydrogen. In certain embodiments of formula (II), $X_{13}$ is deuterium.

In certain embodiments of formula (II), $X_5$, $X_6$, $X_7$, $X_8$, $X_9$, $X_{10}$, $X_{11}$, and $X_{12}$ are deuterium; and $X_{14}$, $X_{15}$, and $X_{16}$ are deuterium.

In certain embodiments of formula (II), $X_5$, $X_6$, $X_7$, $X_8$, $X_9$, $X_{10}$, $X_{11}$, and $X_{12}$ are deuterium; $X_{13}$ is deuterium; and $X_{14}$, $X_{15}$, and $X_{16}$ are deuterium.

In certain embodiments of formula (II), $X_5$ and $X_6$ are deuterium, $X_7$ and $X_8$ are deuterium, $X_9$ and $X_{10}$ are deuterium, and/or $X_{11}$ and $X_{12}$ are deuterium.

In certain embodiments of formula (II), $X_5$ and $X_6$ are deuterium. In certain embodiments of formula (II), $X_7$ and $X_8$ are hydrogen, $X_9$ and $X_{10}$ are hydrogen, and/or $X_{11}$ and $X_{12}$ are hydrogen. In further embodiments, each of $X_7$, $X_8$, $X_9$, $X_{10}$, $X_{11}$, $X_{12}$, $X_{13}$, and $X_{14}$ is hydrogen.

In certain embodiments of formula (II), $X_1$, $X_2$, $X_3$, $X_4$, are deuterium.

In certain embodiments of formula (II), $X_1$, $X_2$, $X_3$, $X_4$, are hydrogen In certain embodiments of formula (II), $X_5$, $X_6$, $X_7$, $X_8$ are deuterium.

In certain embodiments of formula (II), $X_5$, $X_6$, $X_7$, and $X_8$ are hydrogen.

In certain embodiments of formula (II), $X_{13}$ and $X_{14}$ are deuterium.

In certain embodiments of formula (II), $X_{13}$ and $X_{14}$ are hydrogen.

In certain embodiments, the compound of formula (II) may be isolated.

In certain embodiments, the compound of formula (II) may be purified.

Accordingly, the present invention provides a composition enriched in the deuterated derivative over the non-deuterated analog.

In certain embodiments, the compound of formula (II) is isolated or purified, e.g., the compound of formula (II) is present at a purity of at least about 50% by weight (e.g., at least about 55%, about 60%, about 65%, about 70%, about 75%, about 80%, about 85%, about 90%, about 95%, about 97%, about 98%, about 98.5%, about 99%, about 99.5% or about 99.9% or greater) of the total amount of isotopologues of formula (II) present. Thus, in particular embodiments, a composition comprising a compound of formula (II) includes a distribution of isotopologues of the compound, provided at least about 50% of the isotopologues by weight are the recited compound. In further embodiments, at least about 90%, about 95%, about 97%, about 98%, about 98.5%, about 99%, about 99.5% or about 99.9% or greater of the isotopologues by weight are the recited compound.

In certain embodiments, any position in the compound of formula (II) designated as having D has a minimum deuterium incorporation of at least about 45% (e.g., at least about 52.5%, at least about 60%, at least about 67.5%, at least about 75%, at least about 82.5%, at least about 90%, at least about 95%, at least about 97%, at least about 99%, or at least about 99.5% or greater) at the designated position(s) of the compound of formula (II). Thus, in particular embodiments, a composition comprising a compound of formula (II) includes a distribution of isotopologues of the compound, provided at least about 45% of the isotopologues include a D at the designated position(s). In further embodiments, at least about 90%, about 95%, about 97%, about 98%, about 98.5%, about 99%, about 99.5% or about 99.9% or greater of the isotopologues include a D at the designated position(s).

In certain embodiments, a compound of formula (II) is "substantially free or" other isotopologues of the compound, e.g., less than about 50%, less than about 25%, less than about 10%, less than about 5%, less than about 2%, less than about 1%, or less than about 0.5%, of other isotopologues are present.

III. Formulations Of The Invention

In certain embodiments, the invention provides a pharmaceutical composition, e.g., a pharmaceutical composition formulated for oral administration, such as pills (e.g., tablets, capsules, caplets, troaches, lozenges, caches, gelcaps, caps, pellets, boluses, pastilles, orally disintegrating tablets, sublingual tablets and buccal tablets), formulated for oral administration, e.g., single-layer tablet composition, comprising neuro-attenuating ketamine (NAKET), e.g., with reduced neurological adverse effects compared to existing oral formulations or any of the compounds described herein (e.g., ketamine, norketamine, a compound according to any one of formulas (I), (I-A), (I-B), and (II), or any of the compounds described in Tables A-D, or in any of the Examples provided herein), or a pharmaceutically acceptable salt thereof. For clarity, the "neuro-attenuating ketamine (NAKET)" utilized in the present invention is ketamine, or a ketamine derivative that is engineered to act in a similar fashion, formulated to ensure the steady release of a therapeutically effective concentration of ketamine and/or the ketamine derivative from an oral pharmaceutical composition without sedative or psychotomimetic toxic spikes in ketamine and/or ketamine derivative plasma concentration. Such spikes in ketamine plasma concentration have been well-documented to have serious psychotomimetic directed side effects including, but not limited to hallucination, dizziness, and nausea; which can not only have immediate repercussions, but also adversely effect treatment compliance. In this regard, the present invention provides novel and inventive formulations for oral administration comprising, e.g., optimal matrices discovered for the long-term steady release of a neuro-attenuating ketamine (NAKET) compound, including ketamine, with reduced sedative and psychotomimetic side effects.

In certain embodiments, the invention provides a pharmaceutical composition, e.g., a pharmaceutical composition formulated for oral administration, such as pills (e.g., tablets, capsules, caplets, troaches, lozenges, caches, gelcaps, caps, pellets, boluses, pastilles, orally disintegrating tablets, sublingual tablets and buccal tablets) for oral administration, e.g., single-layer tablet composition, comprising a neuro-attenuating norketamine (NANKET), e.g., with reduced neurological adverse effects compared to existing oral formulations, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof. For clarity, the "neuro-attenuating norketamine (NANKET)" utilized in the present invention is norketamine, or a norketamine derivative that is engineered to act in a similar fashion, formulated to ensure the steady release of a therapeutically effective concentration of norketamine and/or the norketamine derivative from an oral pharmaceutical composition without sedative or psychotomimetic toxic spikes in norketamine and/or norketamine derivative plasma concentration.

In certain embodiments, the neuro-attenuating ketamine is psychotomimetic-attenuating ketamine (PAKET), wherein the neurologically toxic spikes are psychotomimetic toxic spikes, including but are not limited to hallucination, dizziness, and nausea.

In certain embodiments, the neuro-attenuating ketamine is psychotomimetic-attenuating norketamine (PANKET), wherein the neurologically toxic spikes are psychotomimetic toxic spikes, including but are not limited to hallucination, dizziness, and nausea.

In certain embodiments, the pharmaceutical composition (e.g. a tablet composition formulated for oral administration such as a single-layer tablet composition), comprises any of the compounds described herein (e.g., ketamine, norketamine, a compound according to any one of formulas (I), (I-A), (I-B), and (II), or any of the compounds described in Tables A-D, or in any of the Examples provided herein), or a pharmaceutically acceptable salt thereof.

In certain embodiments of the present invention, the tablet composition is a modified-release tablet adapted for sustained release and preferably maximum sustained release.

In certain embodiments of the present invention, the tablet composition is adapted for tamper resistance. In particular embodiments, the tablet composition comprises polyethylene oxide (PEO), e.g., MW about 2,000 to about 7,000 KDa, in combination with HPMC. In particular embodiments, the tablet composition may further comprise polyethylene glycol (PEG), e.g., PEG 8K. In particular embodiments, the tablet composition may further comprise polymer carrying one or more negatively charged groups, e.g., polyacrylic acid. In specific embodiments, the tablet composition comprising PEO is further subjected to heating/annealing, e.g., extrusion conditions.

In certain embodiments of the present invention, the NAKET comprises a combination of (i) a water-insoluble neutrally charged non-ionic matrix; (ii) a polymer carrying one or more negatively charged groups; and (iii) ketamine or a ketamine derivative.

In certain embodiments of the present invention, the NANKET comprises a combination of (i) a water-insoluble neutrally charged non-ionic matrix; (ii) a polymer carrying one or more negatively charged groups; and (iii) norketamine or a norketamine derivative.

In certain embodiments of the preset invention, the pharmaceutical composition comprises a combination of (i) a water-insoluble neutrally charged non-ionic matrix; (ii) a polymer carrying one or more negatively charged groups; and (iii) any of the compounds described herein (e.g., ketamine, norketamine, a compound according to any one of formulas (I), (I-A), (I-B), and (II), or any of the compounds described in Tables A-D, or in any of the Examples provided herein), or a pharmaceutically acceptable salt thereof.

In certain embodiments of the present invention, the polymer carrying one or more negatively charged groups is selected from the group consisting of polyacrylic acid, polylactic acid, polyglycolic acid, polymethacrylate carboxylates, cation-exchange resins, clays, zeolites, hyaluronic acid, anionic gums, salts thereof, and mixtures thereof. In particular embodiments, the anionic gum is selected from the group consisting of naturally occurring materials and semi-synthetic materials. In a specific embodiment, the naturally occurring material is selected from the group consisting of alginic acid, pectin, xanthan gum, carrageenan, locust bean gum, gum arabic, gum karaya, guar gum, and gum tragacanth. In another specific embodiment, the semi-synthetic material is selected from the group consisting of carboxymethyl-chitin and cellulose gum.

Moreover, without wishing to be bound by theory, in certain embodiments, the role of the polymer carrying one or more negatively charged groups, e.g., moieties of acidic nature as in those of the acidic polymers described herein, surprisingly offers significant retention of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the matrix. In particular embodiments, this negative charge may be created in situ, for example, based on release of a proton due to pKa and under certain pH conditions or through electrostatic interaction/creation of negative charge. Further noting that acidic polymers may be the salts of the corresponding weak acids that will be the related protonated acids in the stomach; which, and without wishing to be bound by theory, will neutralize the charge and may reduce the interactions of the ketamine, norketamine, or derivatives thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, with the matrix. In addition, the release matrix may be further complemented by other inactive pharmaceutical ingredients to aid in preparation of the appropriate solid dose form such as fillers, disintegrants, flow improving agents, lubricants, colorants, taste maskers.

In certain embodiments of the present invention, the tablet composition is adapted for tamper resistance. In particular embodiments, the tablet composition comprises polyethylene oxide (PEO), e.g., MW about 2,000 to about 7,000 KDa. In specific embodiments, the tablet composition comprising PEO is further subjected to heating/annealing, e.g., extrusion.

In certain embodiments of the present invention, the non-ionic matrix is selected from cellulose-based polymers such as HPMC, alone or enhanced by mixing with components selected from the group consisting of starches; waxes; neutral gums; polymethacrylates; PVA; PVA/PVP blends; and mixtures thereof.

In certain embodiments of the present invention, the cellulose-based polymer is hydroxypropyl methylcellulose (HPMC). In a specific embodiment, the tablet composition comprises about 20-60% hydroxypropyl methylcellulose by weight, about 10-30% starch by weight, or any combination thereof.

In certain embodiments, the pharmaceutical composition is formulated for rectal or vaginal administration.

In certain embodiments, the pharmaceutical composition is formulated for intranasal or inhalation, like aerosols, inhalers, nebulizers and vaporizers, administration.

In certain embodiments, the pharmaceutical composition is formulated for intraoral administration.

In certain embodiments, the pharmaceutical composition is formulated for parenteral administration, such as intravenous, intramuscular, intradermal, subcutaneous, intraosseous, caudal, intrathecal or intraperitoneal administration.

In certain embodiments, the pharmaceutical composition is formulated for administration by infusion.

In certain embodiments, the pharmaceutical composition is formulated for sublingual, orally disintegrating or buccal administration.

In certain embodiments, the pharmaceutical composition is formulated for ophthalmic or otic administration.

In certain embodiments, the pharmaceutical composition is formulated for topical administration like pastes, creams, ointments, gels, liquids, sprays, skin patches, dermal patches, balms, salves and implants.

In certain embodiments of the present invention, the pharmaceutical composition (e.g., a pharmaceutical composition formulated for, for example, oral (e.g., intraoral administration or a tablet, caplet, gelcap, cap or capsule composition), rectal, vaginal, intransal, inhalation, otic, ophthalmic, topical, sublingual, orally disintegration, buccal, parenteral, intravenous, subcutaneous or intramuscular administration, or formulated for administration by infusion, comprises an amount of ketamine, norketamine, or a derivative thereof, any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for the treatment of pain. In particular embodiments of the invention, the pain treated is cancer pain, e.g., refractory cancer pain. In particular embodiments of the invention, the pain treated is post-surgical pain. In particular embodiments of the invention, the pain treated is orthopedic pain. In particular embodiments of the invention, the pain treated is back pain. In particular embodiments of the invention, the pain treated is neuropathic pain. In particular embodiments of the invention, the pain treated is dental pain. In particular embodiments of the invention, the pain treated is chronic pain in opioid-tolerant patients.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for the treatment of depression.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for the treatment of brain injury.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for the treatment of stroke.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in migraine, e.g., with aura.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in refractory asthma.

In certain embodiments of the present invention, the pharmaceutical composition (e.g., a pharmaceutical composition formulated for oral (e.g., intraoral administration or a tablet composition), rectal, intransal, intravenous, sublinutal, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating alcohol dependence.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating post traumatic stress disorder (PTSD).

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating depression (e.g., treatment resistant depression (TRD) or bipolar depression).

In certain embodiments of the present invention, the pharmaceutical composition (e.g., a pharmaceutical composition formulated for oral (e.g., Intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating major depressive disorder (MDD).

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating anxiety (e.g., generalized anxiety disorder).

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating schizophrenia.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises all amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating bipolar disorder.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating suicidality or suicidal ideation.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating autism.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating diabetic neuropathy.

In certain embodiments of the present invention, the pharmaceutical compostion (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating neuropathic pain.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating acute pain (e.g., acute trauma pain).

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating chronic pain.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating levodopa-induced dyskinesia.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating or modulating a speudobulbar effect or Bulbar function.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating Alzheimer's disease or conditions associated with Alzheimer's disease (e.g., Alzheimer's dementia or Alzheimer's agitation).

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, therapeutically effective for use in treating tinnitus.

In certain embodiments of the present invention, the pharmaceutical composition (e.g., a pharmaceutical composition formulated for oral (e.g., intraoral administration or a tablet composition), rectal, intransal, intravenous, sublingual, or intramuscular administration, or formulated for administration by infusion) comprises an amount of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, released from the matrix with a rate of about 0.05-2 mg/kg/h over a period of about 12-24 hours, e.g., about 24 hours.

In certain embodiments of the present invention, the neuro-attenuating ketamine achieves a combined concentration of ketamine (or a ketamine derivative) and its metabolite norketamine (or corresponding metabolic norketamine derivative), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in plasma in the range of about 10-500 ng/ml, and maintains this concentration for duration of the release period. In particular embodiments, the neuro-attenuating ketamine achieves a combined concentration of ketamine (or a ketamine derivative) and its metabolite norketamine (or corresponding metabolic norketamine derivative), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in plasma in the range of about 10-300 ng/ml, and maintains this concentration for duration of the release period. In particular embodiments, the neuro-attenuating ketamine achieves a combined concentration of ketamine (or a ketamine derivative) and its metabolite norketamine (or corresponding metabolic norketamine derivative) in plasma in the range of about 10-100 ng/ml, or about 50-100 ng/ml, and maintains this concentration for duration of the release period. In particular embodiments, the neuro-attenuating ketamine achieves a combined concentration of ketamine (or a ketamine derivative) and its metabolite norketamine (or corresponding metabolic norketamine derivative) in plasma in the range of about 10-20 ng/ml, and maintains this concentration for duration of the release period.

In certain embodiments of the present invention, the neuro-attenuating norketamine (or a norketamine derivative), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, achieves a concentration in plasma in the range of about 10-500 ng/ml, and maintains this concentration for duration of the release period. In particular embodiments, the neuro-attenuating norketamine (or a norketamine derivative), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, achieves a concentration in plasma in the range of about 10-300 ng/ml, and maintains this concentration for duration of the release period. In particular embodiments, the neuro-attenuating norketamine (or a norketamine derivative), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, achieves a concentration in plasma in the range of about 10-100 ng/ml, and maintains this concentration for duration of the release period. In particular embodiments, the neuro-attenuating norketamine (or a norketamine derivative), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, achieves a concentration in plasma in the range of about 10-20 ng/ml, and maintains this concentration for duration of the release period.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is greater than 4 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is greater than about 8 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is greater than about 12 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is greater than about 16 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is greater than about 20 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is greater than (or equal to) about 24 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is greater than (or equal to) about 28 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is greater than (or equal to) about 32 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is greater than (or equal to) about 36 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is less than about 48 hours.

In certain embodiments of the present invention, the release period of the NAKET or NANKET, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in the formulations of the invention is less than about 36 hours.

In certain embodiments of the present invention, the tablet compositions of the present invention are utilized as a 2-times a day (BID), 3-times a day (TID) or 4-times a day (QID) application.

In certain embodiments of the present invention, the tablet compositions of the present invention are utilized as a once a day (QD) application.

In certain embodiments of the present invention, the tablet compositions of the present invention are utilized as a nightly (QHS) application.

In certain embodiments of the present invention, the tablet compositions of the present invention are utilized as an as needed (PRN) application.

In certain embodiments of the present invention, the oral pharmaceutical compositions are enhanced. In particular embodiments, due to the efficiency of administration, the formulation is able to utilize less ketamine, norketamine, or derivative thereof for treatment to achieve the same effect as comparative oral tablets not described by the present invention.

In certain embodiments of the present invention, the oral administration event, which provides the appropriate single unit dose, may comprise one single pill or multiple pills.

In addition, to protect the tablet from the acidic environment in the stomach and maintain a long-term release, various types of enteric coating may be used in certain embodiments.

In certain embodiments of the present invention, a single-layer tablet or caplet is coated with protective layers of inactive pharmaceutical ingredients to form a modified-release formulation, e.g., to ensure steady release of the drug from the matrix and avoid concentration bursts at the early release time points.

Another embodiment of the present invention provides formulation of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof as a modified-release formulation, that ensures the steady release of a therapeutically effective concentration of the ketamine, norketamine, or the derivative thereof, or any of the compounds described herein (e.g., a compound according to any one of formulas (I), (I-A), (I-B), and (II), or any of the compounds described in Tables A-D, of the Examples provided herein), or a pharmaceutically acceptable salt thereof, from such oral modified-release formulation, without sedative or psychotomimetic toxic spikes in plasma concentration of the ketamine, norketamine, or derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof. This formulation comprises the ketamine, norketamine, or derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, formulated in an osmotic controlled release pharmaceutical composition, such as a tablet, caplet or granules. In these formulations a single core layer containing the ketamine, norketamine, or derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, (e.g., as defined by other tablet formulations described herein) is surrounded by semi-permeable membrane with or without drug delivery orifice. Without wishing to be bound by theory, because these systems use water osmotic pressure for the controlled delivery of the active material, delivery rates are expected to be independent of gastrointestinal conditions. In combination with the novel and inventive aspects of the present invention, osmotic asymmetric-membrane technology or AMT (e.g., technology directed to a single-layer tablet, caplet or granules coated with an insoluble, asymmetric microporous membrane produced by controlled phase separation) may be used to produce formulations useful in the methods of treatment and kits described herein.

In certain embodiments of the invention, the ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, may be formulated as a pharmaceutically acceptable salt thereof, e.g., ketamine hydrochloride, ketamine aspartate, ketamine succinate, etc, such that the ketamine/norketamine counterion does not significantly effect formulation as described herein for ketamine, norketamine, or the derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, or the ability of the ketamine, norketamine, or the derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, to achieve the desired therapeutic effects described herein, i.e., with similar steady release of a therapeutically effective concentration (e.g., based on indication) from an oral pharmaceutical composition, such as a tablet, a caplet, a capsule, a gelcap, a cap or granules, without sedative or psychotomimetic toxic spikes in the concentration of ketamine, norketamine, or derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof. Exemplary salts, within this scope, may include but are not limited to: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid, citric acid, succinic acid, tartaric acid; and other mineral and carboxylic acids well known to those skilled in the art. Additional examples may include salts with inorganic cations such as sodium, potassium, calcium, magnesium, lithium, aluminum, zinc, etc; and salts formed with pharmaceutically acceptable amines such as ammonia, alkylamines, hydroxyalkylamines, lysine, arginine, N-methylglucamine, procaine and the like. In specific embodiments, the pharmaceutically acceptable salt hydrochloride salt.

Another embodiment of the present invention provides a kit for the treatment of a subject with ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, comprising pharmaceutical composition, such as an orally administered pharmaceutical composition like a pill, of any one of the formulations described herein comprising neuro-attenuating ketamine (NAKET) and/or neuro-attenuating norketamine (NANKET), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, and instructions for use in the treatment, prevention or management of a disease, disorder or condition, such as pain, e.g., as described herein.

In particular embodiments of the invention, the pain treated is cancer pain, e.g., refractory cancer pain.

In particular embodiments of the invention, the pain treated is post-surgical pain.

In particular embodiments of the invention, the pain treated is orthopedic pain.

In particular embodiments of the invention, the pain treated is back pain.

In particular embodiments of the invention, the pain treated is neuropathic pain.

In particular embodiments of the invention, the pain treated is dental pain.

In particular embodiments of the invention, the pain treated is chronic pain in opioid-tolerant patients.

Another embodiment of the present invention provides a kit for the treatment of a subject with ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, comprising a pharmaceutical composition, such as an orally administered tablet pharmaceutical composition like a pill, of any one of the formulations of the present invention. comprising neuro-attenuating ketamine (NAKET), neuro-attenuating norketamine (NANKET), and/or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, and instructions for use in the treatment of brain injury.

Another embodiment of the present invention provides a kit for the treatment of a subject with ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, comprising a pharmaceutical composition, such as an orally administered tablet pharmaceutical composition like a pill, of any one of the formulations of the present invention comprising neuro-attenuating ketamine (NAKET), neuro-attenuating norketamine (NANKET), and/or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, and instructions for use in the treatment of depression.

Another embodiment of the present invention provides a kit for the treatment of a subject with ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, comprising a pharmaceutical composition, such as an orally administered tablet pharmaceutical composition like a pill, of the formulations of the present invention comprising neuro-attenuating ketamine (NAKET), neuro-attenuating norketamine (NANKET), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, and instructions for use in the treatment of migraine, e.g., with aura.

Another embodiment of the present invention provides a kit for the treatment of a subject with ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, comprising a pharmaceutical composition, such as an orally administered tablet pharmaceutical composition like a pill, of the present invention comprising neuro-attenuating, ketamine (NAKET), neuro-attenuating norketamine (NANKET), and/or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, and instructions for use in the treatment of refractory asthma.

Another embodiment of the present invention provides a kit for the treatment of a subject with ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, comprising a pharmaceutical composition, such as an orally administered tablet pharmaceutical composition like a pill, of any one of the formulations of the present invention comprising neuro-attenuating ketamine (NAKET), neuro-attenuating norketamine (NANKET), or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, and instructions for use in the treatment of stroke.

Another embodiment of the present invention provides a kit for the treatment of a subject with ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, comprising a pharmaceutical composition, such as an orally administered tablet pharmaceutical composition like a pill, of any one of the formulations of the present invention comprising neuro-attenuating ketamine (NAKET), neuro-attenuating norketamine (NANKET), and/or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, and instructions for use in the treatment of alcohol dependence.

In embodiments, the invention features an oral, modified-release pharmaceutical composition for oral administration to a subject for treating the subject diagnosed with, suffering from or susceptible to a disease, disorder or condition, such as those for which ketamine treatment may be indicated, considered or recommended, wherein the subject is in need of treatment with said oral, modified-release pharmaceutical composition, said oral, modified-release pharmaceutical composition comprising:

(a) a drug selected from a group consisting of ketamine, a deuterium-enriched neuro-attenuating ketamine (NAKET) compound, norketamine, and/or a deuterium-enriched neuro-attenuating norketamine (NANKET) compound or a pharmaceutically acceptable salt thereof in an effective amount for treating, preventing and/or managing the disease, disorder, or condition in the subject; and (b) a pharmaceutically acceptable excipient;

whereby, upon oral administration of the modified-release pharmaceutical composition to the subject, a steady release of said drug from the modified-release pharmaceutical composition is maintained so that no neurologically toxic spike in the subject's plasma occurs during the release period of said drug from said pharmaceutical composition.

In certain embodiments of the kit, the instructions for use form an integrated component of the packaging for the pharmaceutical composition.

A. General Tablet Formulations of the Invention

The formulations of the invention comprise orally administered pharmaceutical compositions, such as tablet, capsule, caplets, gelcap and cap compositions, which may include uncoated tablets or coated tablets, caplets and caps (including film-coated, sugar-coated tablets, and gastro-resistant/enteric-coated tablets). The oral pharmaceutical caompositions for oral use may include the active ingredients, e.g., ketamine and/or norketamine, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, mixed with pharmaceutically acceptable inactive excipients such as diluents, disintegrating agents, binding agents, lubricating agents, powder flow improving agent, wetting agents, sweetening agents, flavoring agents, coloring agents and preservatives. Moreover, oral pharmaceutical caompositions of the present invention are solid dosage forms intended for oral administration, e.g., obtained by dry granulation with single or multiple compressions of powders or granules. In certain embodiments, the oral pharmaceutical caompositions may be obtained by using wet granulation techniques. In certain embodiments, the oral pharmaceutical caompositions may be obtained by molding, heating/annealing, or extrusion techniques.

In certain embodiments, the oral tablets are right circular solid cylinders, the end surfaces of which are flat or convex, and the edges of which may be beveled. In particular embodiments, the surfaces are convex. In addition, they may have lines or break-marks (scoring), symbols or other markings.

In certain embodiments, the break-mark(s) is/are intended to permit accurate subdivision of the tablet in order to provide doses of less than one tablet. In certain embodiments of the invention, the tablet compositions comprise one or more excipients such as diluents, binders, disintegrating agents, glidants, lubricants, substances capable of modifying the behavior of the dosage forms and the active ingredient(s) in the gastrointestinal tract, coloring matter authorized by the appropriate national or regional authority and flavoring substances. When such excipients are used it is necessary to ensure that they do not adversely affect the stability, dissolution rate, bioavailability, safety or efficacy of the active ingredient(s); there must be no incompatibility between any of the components of the dosage form.

Coated tablets are tablets covered with one or more layers of mixtures of substances such as natural or synthetic resins, polymers, gums, fillers, sugars, plasticizers, polyols, waxes, coloring matters authorized by the appropriate national or regional authority, and flavoring substances. Such coating materials do not contain any active ingredient, e.g., ketamine, norketamine, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof. The tablets may be coated for a variety of reasons such as protection of the active ingredients from burst release from the matrix, air, moisture or light, masking of unpleasant tastes and odors or improvement of appearance. The substance used for coating may be applied as a solution or suspension.

In certain embodiments, the manufacturing processes for the oral pharmaceutical caompositions, tablets, meet the requirements of good manufacturing practices (GMP). In certain embodiments, one or more measures are taken in the manufacture of oral pharmaceutical caompositions selected from the following: ensure that mixing with excipients is carried out in a manner that ensures homogeneity; ensure that the oral pharmaceutical caompositions possess a suitable mechanical strength to avoid crumbling or breaking on subsequent processing, e.g., coating, storage and distribution; minimize the degradation of the active ingredient; minimize the risk of microbial contamination; minimize the risk of cross-contamination. In addition, in the manufacture of scored tablets (tablets bearing a break-mark or marks) for which subdivision is intended in order to provide doses of less than one tablet measures are taken to: ensure the effectiveness of break-marks with respect to the uniformity of mass or content, as appropriate, of the subdivided parts so that the patient receives the intended dose.

In general a suitable dose will be in the range of about 0.01 to about 10 mg per kilogram body weight of the recipient per day, preferably in the range of about 0.1 to about 5 mg per kilogram body weight per day. Additional details on techniques for formulation and administration are well described in the scientific and patent literature, see, e.g., the latest edition of Remington's Pharmaceutical Sciences, Maack Publishing Co, Easton Pa. ("Remington's"). After a pharmaceutical composition has been formulated in an acceptable carrier, it can be placed in an appropriate container and labeled for treatment of an indicated condition). For administration of the NAKET or NANKET formulations, or formulations comprising any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, such labeling would include, e.g., instructions concerning the amount, frequency, method of administration, treatment regimen and indications.

B. Compliance with Monographs

In certain embodiments, the formulations of the present invention conform to certain industry accepted monographs to afford compliance with the Federal Food Drug and Cosmetic Act. In particular, the formulations of the present invention conform and are considered acceptable under visual inspection, uniformity of mass analysis, uniformity of content analysis, and/or dissolution/disintegration analysis all of which are established by a relevant monograph.

In certain embodiments, throughout manufacturing certain procedures are validated and monitored by carrying out appropriate in-process controls. These are designed to guarantee the effectiveness of each stage of production. In-process controls during tablet production may include the moisture content of the final lubricated blend, the size of granules, the flow of the final mixture and, where relevant, the uniformity of mass of tablet cores before coating. In-process controls during tablet production may also include the dimensions (thickness, diameter), uniformity of mass, hardness and/or crushing force, friability, disintegration or dissolution rate (for example, for modified-release tablets) of the finished dosage form. Suitable test methods that may be used to demonstrate certain of these attributes are known in the art.

In certain embodiments, packaging maybe or is required to be adequate to protect the pharmaceutical compositions, including tablets, from light, moisture and damage during transportation.

In additional embodiments, the commercially available formulation (e.g., kit) complies with the labeling requirements established under Good Manufacturing Practices (GMP). Such label includes:
(1) the name of the pharmaceutical product;
(2) the name(s) of the active ingredient(s); International Nonproprietary Names (INN) should be used wherever possible;
(3) the amount of the active ingredient(s) in each tablet and the number of tablets in the container;
(4) batch (lot) number assigned by the manufacturer;
(5) the expiry date and, when required, the date of manufacture;
(6) any special storage conditions or handling precautions that may be necessary;
(7) directions for use, warnings, and precautions that may be necessary;
(8) the name and address of the manufacturer or the person responsible for placing the product on the market;
(9) for scored tablets where the directions for use include subdivision to provide doses of less than one tablet, the label should also include: the storage conditions for and the period of use of those subdivided part(s) not immediately taken or administered.

In certain embodiments, the pharmaceutical compositions, e.g., tablets, are able to withstand handling, including packaging and transportation, without losing their integrity.

IV. Methods Of The Invention

The formulations of the invention may be used in the methods of the invention, e.g., methods of treatment of the invention. As such, the invention relates to the method of use of formulations or compositions (e.g., pharmaceutical compositions) of the invention, which contain neuro-attenuating ketamine (NAKET), neuro-attenuating norketamine (NANKET), and/or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, e.g., for the treatment of pain. As such, in certain embodiments, the invention provides for the management of different kinds of pain, including but not limited to refractory cancer pain, neurologic pain, postoperative pain, complex regional pain syndrome (CRPS), migraine, e.g., with aura, and other conditions including depression, alcohol dependence, refractory asthma, epilepsy, acute brain injury and stroke, Alzheimer's disease and other disorders comprising an oral administration of the formulations of the present invention, described herein. In certain embodiments, the use of formulations of the present invention may be used as a standalone therapy. In certain embodiments, the use of formulations of the present invention may be used as an adjuvant/combination therapy.

In certain embodiments, the invention provides for the management of different kinds of pain, including but not limited to cancer pain, e.g., refractory cancer pain; neuropathic pain; opioid-induced hyperalgesia and opioid-related tolerance; neurologic pain; postoperative/post-surgical pain; complex regional pain syndrome (CRPS); shock; limb amputation; severe chemical or thermal burn injury; sprains, ligament tears, fractures, wounds and other tissue injuries; dental surgery, procedures and maladies; labor and delivery; during physical therapy; radiation poisoning; acquired immunodeficiency syndrome (AIDS); epidural (or peridural) fibrosis; orthopedic pain; back pain; failed back surgery and failed laminectomy; sciatica; painful sickle cell crisis; arthritis; autoimmune disease; intractable bladder pain; pain associated with certain viruses, e.g., shingles pain or herpes pain; acute nausea, e.g., pain that may be causing the nausea or the abdominal pain that frequently accompanies sever nausea; migraine, e.g., with aura; and other conditions including depression (e.g., acute depression or chronic depression), depression along with pain, alcohol dependence, acute agitation, refractory asthma, acute asthma (e.g., unrelated pain conditions can induce asthma), epilepsy, acute brain injury and stroke, Alzheimer's disease and other disorders. In addition, the present invention includes the treatment/management of any combination of these types of pain or conditions.

In certain embodiments, the pain treated/managed is acute breakthrough pain or pain related to wind-up that can occur in a chronic pain condition.

In particular embodiments of the invention, the pain treated/managed is cancer pain, e.g., refractory cancer pain.

In particular embodiments of the invention, the pain treated/managed is post-surgical pain.

In particular embodiments of the invention, the pain treated/managed is orthopedic pain.

In particular embodiments of the invention, the pain treated/managed is back pain.

In particular embodiments of the invention, the pain treated/managed is neuropathic pain.

In particular embodiments of the invention, the pain treated/managed is dental pain.

In particular embodiments of the invention, the condition treated/managed is depression.

In particular embodiments of the invention, the pain treated/managed is chronic pain in opioid-tolerant patients.

In embodiments, the invention relates to a method of treating a disease or condition by modulating NMDA activity, where the method comprises administering an effective amount of any of the compounds described herein (e.g., a compound according to formula (I), or a pharmaceutically acceptable salt thereof, or any of the compounds described in Tables A-D, or comprising NAKET or NANKET) to a subject in need thereof. In embodiments, the disease or condition is selected from: levodopa-induced dyskinesia; dementia (e.g., Alzheimer's dementia), tinnitus, treatment resistant depression (TRD), major despressive disorder, neuropathic pain, agitation resulting from or associated with Alzheimer's disease, pseudobulbar effect, autism, Bulbar function, generalized anxiety disorder, Alzheimer's disease, schizophrenia, diabetic neuropathy, acute pain, depression, bipolar depression, suicidality, neuropathic pain, or post-traumatic stress disorder (PTSD). In embodiments, the disease or condition is a psychiatric or mental disorder (e.g., schizophrenia, mood disorder, substance induced psychosis, major depressive disorder (MDD), bipolar disorder, bipolar depression (BDep), post-traumatic stress disorder (PTSD), suicidal ideation, anxiety, obsessive compulsive disorder (OCD), and treatment-resistant depression (TRD)). In other embodiments, the disease or condition is a neurological disorder (e.g., Huntington's disease (HD), Alzheimer's disease (AD), or systemic lupus erythematosus (SLE)).

For example, in one embodiment, the invention provides a method of treating a subject with ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, comprising the step of administering to a subject an orally administered tablet composition, e.g., matrix composition, of the present invention comprising neuro-attenuating ketamine (NA-KET), neuro-attenuating norketamine (NANKET), and/or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, such that the subject is treated.

The administering physician can provide a method of treatment that is prophylactic or therapeutic by adjusting the amount and timing of NAKET, NANKET, and/or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, administration on the basis of observations of one or more symptoms of the disorder or condition being treated.

In another embodiment, the invention provides a method of continuous oral administration of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, comprising the steps of formulating ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, into a tablet, e.g., single-layer tablet, that provides a steady release of a therapeutically effective concentration of the ketamine, norketamine, or derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, from an oral tablet over a complete release period without neurologically toxic spikes, e.g., no sedative or psychotomimetic toxic spikes in plasma ketamine concentration, to produce a neuro-attenuating ketamine (NAKET), neuro-attenuating norketamine (NANKET), and/or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, tablet composition, e.g., single-layer tablet composition; and orally administering the tablet composition to a subject, such that the NAKET, NANKET, and/or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, provides a continuous therapeutically effective concentration of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, to the subject.

In certain embodiments of the invention, the subject is a mammal.

In certain embodiments of the invention, the mammal is a human.

In another embodiment, the present invention provides a method of formulating ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, to ensure the steady release of a therapeutically effective concentration of the ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, from an oral tablet without neurologically toxic spikes, e.g., sedative or psychotomimetic toxic spikes, in plasma ketamine concentration. In a particular embodiment, the method comprises the step of combining (i) a water-insoluble neutrally charged non-ionic matrix; (ii) a polymer carrying one or more negatively charged groups; and (iii) ketamine or a derivative thereof, to produce a neuro-attenuating ketamine orally administered tablet composition, e.g., single-layer. In a particular embodiment, the method comprises the step of combining (i) a water-insoluble neutrally charged non-ionic matrix; (ii) a polymer carrying one or more negatively charged groups; and (iii) norketamine or a derivative thereof, to produce a neuro-attenuating norketamine orally administered tablet composition, e.g., single-layer. In a particular embodiment, the method comprises the step of combining (i) a water-insoluble neutrally charged non-ionic matrix; (ii) a polymer carrying one or more negatively charged groups; and (iii) any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, to produce a neuro-attenuating orally administered tablet composition, e.g., a single-layer tablet. In another particular embodiment, the method comprises the step of combining (i) polyethylene oxide (PEO), e.g., MW about 2,000 to about 7,000 KDa, with HPMC, and (ii) ketamine or a derivative thereof, to produce a neuro-attenuating ketamine orally administered tablet composition, e.g., single-layer. In another particular embodiment, the method comprises the step of combining (i) polyethylene oxide (PEO), e.g., MW about 2,000 to about 7,000 KDa, with HPMC, and (ii) norketamine or a derivative thereof, to produce a neuro-attenuating norketamine orally administered tablet composition, e.g., single-layer. In specific embodiments, wherein the method comprises the step of combining polyethylene oxide (PEO) with HPMC, and ketamine, the tablet composition may further comprise polyethylene glycol (PEG), e.g., PEG 8K, a polymer carrying one or more negatively charged groups, e.g., polyacrylic acid and/or may be further subjected to heating/annealing, e.g., extrusion conditions. In another particular embodiment, the method comprises the step of combining (i) polyethylene oxide (PEO), e.g., MW about 2,000 to about 7,000 KDa, with HPMC, and (ii) any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, to produce a neuro-attenuating orally administered tablet composition, e.g., single-layer. In certain embodiments, the formulations of the invention may be administered in combination with other active therapeutic agents, e.g., opioids to reduce pain. In particular embodiments, the formulations of the present invention serve to reduce the amount of opioids necessary to treat a patient.

In certain embodiments, the formulations of the invention are not administered in combination with other active therapeutic agents.

In certain embodiments, the formulations of the invention may be administered in combination with another formulation of ketamine, e.g., a fast release formulation of ketamine.

In another embodiment, the present invention provides a method of formulating ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, to ensure the steady release of a therapeutically effective concentration of the ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, from an oral tablet without sedative or psychotomimetic toxic spikes in plasma concentration of the ketamine, norketamine, or derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof. The method comprises formulation of ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, in an osmotic controlled release tablet. In these formulations the single core layer containing ketamine, norketamine, or a derivative thereof, or any of the compounds described herein (e.g., a compound according to any one of formulas (I), (I-A), (I-B), and (II), or any of the compounds described in Tables A-D, or in any of the Examples provided herein), or a pharmaceutically acceptable salt thereof, is surrounded by semi-permeable membrane with or without drug delivery orifice. In certain embodiments, combination with the novel and inventive pharmaceutical compositions (e.g., the NAKET or NAN-KET tablet formulations or the pharmaceutical compositions comprising any of the compounds described herein (e.g., a compound according to any one of formulas (I), (I-A), (I-B), and (II), or any of the compounds described in Tables A-D, or in any of the Examples provided herein), or a pharmaceutically acceptable salt thereof) of the present invention and osmotic asymmetric-membrane technology or AMT (e.g., technology directed to a single-layer tablet coated with an insoluble, asymmetric microporous membrane produced by controlled phase separation) may be used to produce formulations useful in the methods and kits described herein.

VI. Exemplification

The present invention is illustrated by the following examples, which are not intended to be limiting in any way.

Example 1

Formulation of the Controlled Release Ketamine Tablet using a Matrix Based on HPMC and Starch 1, by dry granulation using a controlled release matrix based on a combination of hydroxypropyl methyl cellulose (HPMC) Methocel KM100 CR and pre-gelatinized starch Starch 1500. Methocel, Starch 1500, ketamine and Cab-o-Sil (colloidal silicon dioxide) were coarsely mixed and passed through a 40-mesh screen to break-up agglomerates. Microcrystalline cellulose was then added and the mixture blended in a 100 ml tube blender for 15 minutes at 200 rev/min. The full composition of ketamine tablet KTM-1 is presented in Table 1.

After blending, magnesium stearate was added and blended for additional 3 minutes. The 200 mg convex-shaped tablets containing 20 mg of ketamine were compressed using a TDP tablet press and 9 mm dye. By applying a compression force of 8 kN, the tablets of the hardness in the range 13-15 kP were generated. The tablet dissolution was carried out in a Type II dissolution apparatus (paddle) (Distek Premiere 5100 Dissolution System, Distek Inc., North Brunswick, USA) at 100 rpm, 37° C., using 1× PBS buffer, pH=6.8 as an immersion media. Three tablets per batch were tested.

At predetermined time intervals, 1 ml samples were withdrawn (not replaced), filtered and assayed. The amount of ketamine released was measured by HPLC using an Agilent 1100 setup and UV detection at 210 nm. A 20 microliter sample volume was injected onto a Zorbax SB-Phenyl column, 4.6×150 mm, 5 microns, using as the mobile phase a mixture of 70% ammonium acetate (10 mM) and 30% acetonitrile; flow rate 1.5 ml/min; column temperature 40° C. Solutions of known concentrations of ketamine were used to calculate the amount of drug released.

The method was linear in the range of concentration 0.001 to 0.5 mg/ml. Drug release was independent of the pH of the immersion media. A release at pH 1 and 6.8 displayed similar profiles. At 10 h time point, about 92.5% of ketamine has been released.

(FIG. 1). TABLE 1

Ketamine Tablet Compositions Based on the HPMC Matrix.

| Ingredient | Manufacturer's Brand | KTM-1 | KTM-2 | KTM-3 |
|---|---|---|---|---|
| HPMC | Methocel KM100 CR | 50.0% | 41.7% | 45.5% |
| Pre-gelatinized Starch | Starch 1500 | 19.0% | 15.8% | 17.3% |
| Microcrystalline Cellulose | Avicel PH-200 | 20.0% | 16.7% | 18.2% |
| Silica | Cabosil M-5P | 0.5% | 0.4% | 0.5% |
| Ketamine | Ketamine Hydrochloride | 10.0% | 8.3% | 9.1% |
| Polyacrylic Acid | Carbopol 974 NF | 0.0% | 16.7% | 9.1% |
| Mg Stearate | Spectrum | 0.5% | 0.4% | 0.5% |
| Total | | 100% | 100% | 100% |

Example 2

Formulation of the Neuro-Attenuating Ketamine Tablet using HPMC and Polyacrylate Ketamine was formulated into a tablet form by dry granulation following the general procedure as described in the Example 1. The control formulation KTM-1 presented in Table 1 was supplemented by adding polyacrylic acid, Carbopol 974 NF (Noveon), for a total content of 16.7% and 9.1% to make compositions KTM-2 and KTM-3, respectively (See Table 1).

Consequently, this addition led to a surprisingly dramatic slowing down of the release (FIG. 1). Compared to the KTM-1, at the 10 hour time point KTM-2 showed only 49% of the drug was released; and at 24 hours 62% of the ketamine was released.

Moreover, reducing the level of Carbopol (i.e., polyacrylic acid) to about 9% in KTM-3 generated a release profile that matched closely to a window of 24-h, for once-a-day ketamine applications. The amount of the drug released at 24 h was about 82%. Composition KTM-3 was considered for development given typical acceleration of the release rate in vivo.

Example 3

Formulation of Sample 36 Hour Neuro-Attenuating Ketamine Tablet with Kollidon SR Based on the potential for additional in situ electrostatic interactions of ketamine with the polymer matrix to retain the drug, a polyvinylacetate/povidone based polymer (Kollidon® SR) was elected. It consists of 80% Polyvinylacetate and 19% Povidone in a physical mixture, stabilized with 0.8% sodium lauryl sulfate and 0.2% colloidal silica. Kollidon SR possesses good compressibility and typically displays drug release profile independent of the dissolution medium (pH and salt/ion content).

Figure 2:
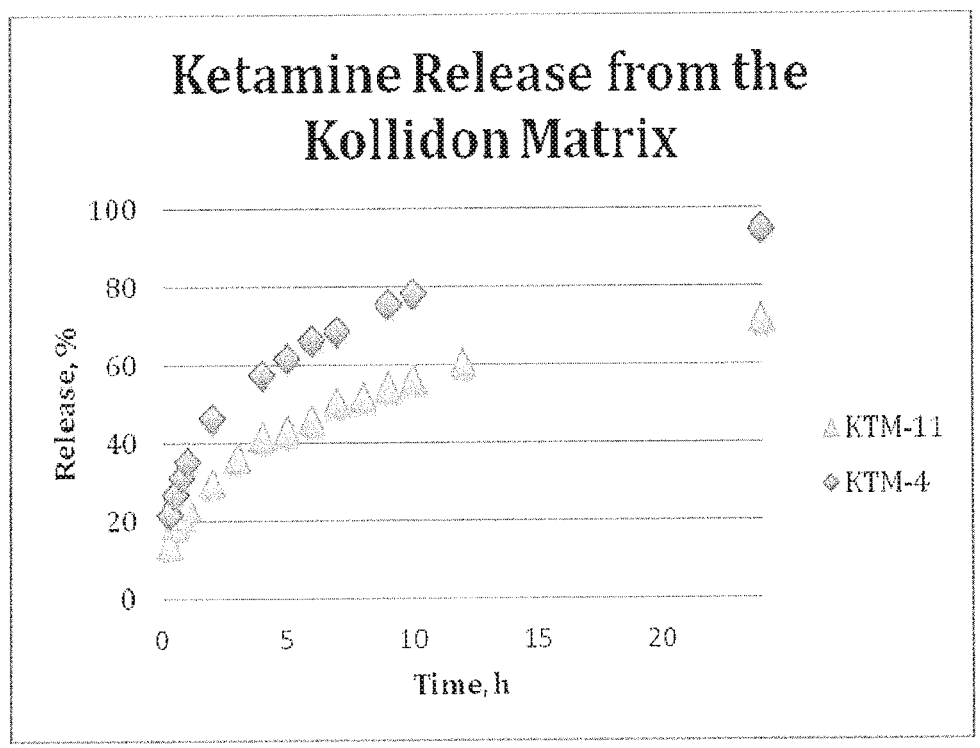
FIG. 2 is a graphical depiction of the release profile of ketamine from the Kollidon matrix, with and without lactose (compositions KTM-4 and KTM-11)
Figure 3:
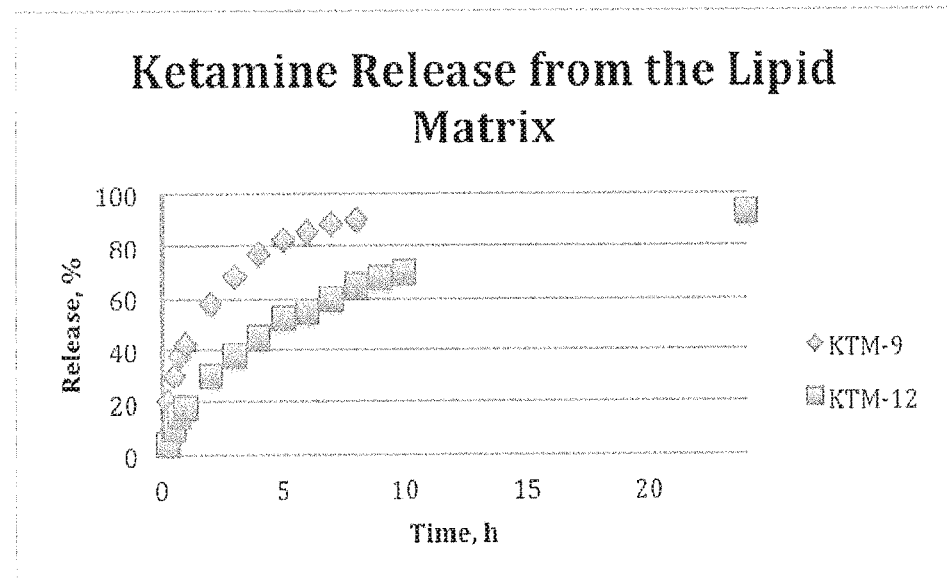
FIG. 3 is a graphical depiction of the release profile of ketamine from a lipid matrix, with and without polyacrylic acid (compositions KTM-9 and KTM-12)
Figure 4:
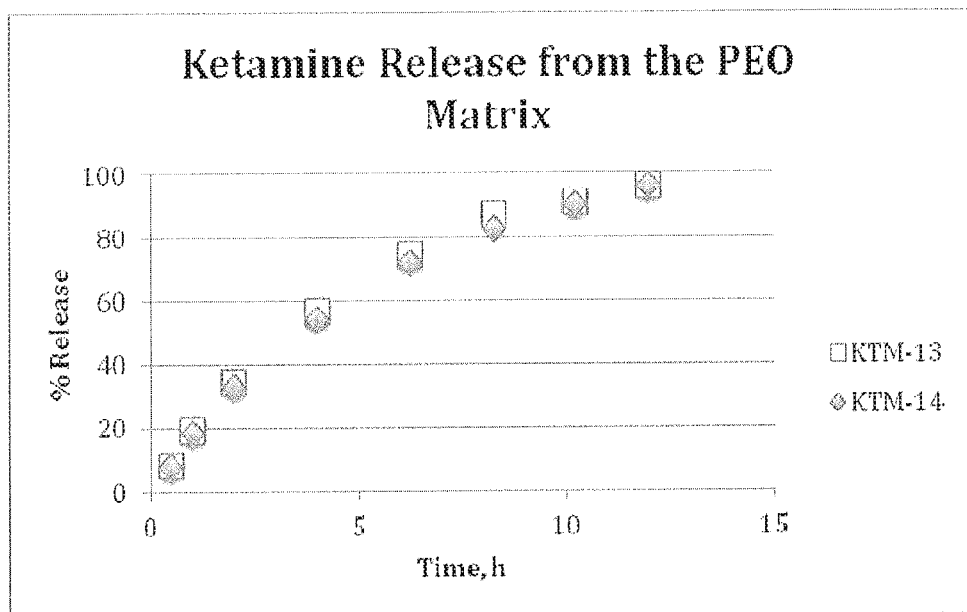
FIG. 4 is a graphical depiction of the release profile of ketamine from a PEO matrix of two different molecular weights.

A 200 mg tablets containing 20 mg of ketamine was produced using protocol similar to Example 2, with a mixture of Kollidon SR and microcrystalline cellulose to produce formulation KTM-11. The tablet composition is presented in the Table 2. The tablets displayed a good hardness, in the range of 15-20 kP, and released 56% of the drug at 10 hours and 78% at 24 hours, with full release expected to be between 36 and 48 hour time points (FIG. 2).

Addition of about 10% of lactose (formulation KTM-4) led to faster release, about 72% of the drug in 10 hours, and about 95% in 24 hours.

TABLE 2

Ketamine Tablet Compositions Based on the Kollidon Matrix.

| Ingredient | Manufacturer's Brand | KTM-11 | KTM-4 |
|---|---|---|---|
| Kollidon | Kollidon SR | 66.8% | 60.0% |
| Microcrystalline Cellulose | Avicel PH-200 | 27.3% | 19.0% |
| Ketamine | Ketamine Hydrochloride | 9.9% | 10.0% |
| Lactose | Lactopress 250 | 0% | 10.0% |
| Mg Stearate | Spectrum | 0.5% | 1.0% |
| Total | | 100% | 100% |

Example 4

Lipophilic Matrix Tablet Formulation of the Neuro-Attenuating Ketamine using Glyceryl Behenate Glyceryl behenate (Compritol®, 888 ATO, Gattefosse) is a hydrophobic fatty acid ester of glycerol, which may be used as a lipophilic matrix-forming agent in the manufacture of sustained-release tablets. When compressed, it forms an insoluble network structure, allowing dissolution fluid to gradually penetrate and subsequent diffusion-controlled drug release to occur through matrix channels and pores. Unlike hydrophilic matrix systems, which utilize swellable polymers such as HPMC and rely on diffusion and erosion mechanisms, drug release from insoluble matrix systems is dependent on the rate and extent of water permeation and the aqueous solubility of the drug embedded in the matrix.

The 200 mg tablets containing 20 mg of ketamine were produced using a mixture of Compritol (20%), dibasic calcium phosphate and lactose (formulation KTM-9). The tablets display a relatively low hardness, in the range of 6-7 kP, and release about 92% of the drug in 8 hour. Addition of about 10% of polyacrylic acid (formulation KTM-12) leads to slowed release, about 65% at 10 hour and about 92% at 24 hour time points.

Example 5

Formulation of the Controlled Release Ketamine Tablet using a Matrix Based on PEO Polyethylene oxide (PEO) is a known ingredient for the extended release solid dose forms. It has been shown to display similar formulation functional properties to HPMC. PEO-based formulations may be produced by dry granulation as well by melt extrusion, producing solid dispersions of the active pharmaceutical ingredients. As a thermoplastic polymer, PEO has glass transition temperatures in the range of 80-100° C. (depending on the molecular weight; the grade used for extended release formulation are typically within 900-7,000 KDa M average molecular weight) and could be melted during the extrusion process, solubilizing the drugs.

The 220 mg tablets containing 20 mg of ketamine were produced by dry granulation using a mixture of two different grades of PEO (MW about 2,000 and about 7,000 KDa), in combination with HPMC (formulations KTM-13, 14, respectively). The release properties were explored upon changing the following additional variables in the composition and processing: i) Molecular weight of PEO; (ii) Addition of polyacrylic acid as a prototypical acidic ingredient, described herein as a potential to slow down the release (formulation KTM-15); (iii) Addition of the high molecular weight PEG 8K (formulation KTM-16); (iv) annealing of the tablets for 20 min in the oven at 120° C. to mimic the mechanical properties achieved by extrusion (formulation KTM-15a).

The full compositions of tablets KTM-13-16 is presented in Table 3.

The tablets displayed a relatively high hardness, in the range of 15-20 kP that increases upon annealing to 30-35 kP, indicative of acquiring tamper-resistance properties enabled by improved crush resistance. We observed little differentiation in the release properties upon changing any of the above variables, with about 90-100% release achieved in about 12 h of time.

TABLE 3

Ketamine Tablet Compositions Based on the PEO Matrix

| Ingredient | Manufact. Brand | KTM-13 | KTM-14 | KTM-15 | KTM-16 |
|---|---|---|---|---|---|
| PEO, MW = 2M | Colorcon N60K | 67.9% | 0.0% | 60.3% | 52.7% |
| PEO, MW = 7M | Colorcon, WSR-303 LEO | 0.0% | 67.9% | 0.0% | 0.0% |
| HPMC | Methocel KM100 CR | 22.6% | 22.6% | 22.6% | 22.6% |

TABLE 3-continued

Ketamine Tablet Compositions Based on the PEO Matrix

| Ingredient | Manufact. Brand | KTM-13 | KTM-14 | KTM-15 | KTM-16 |
|---|---|---|---|---|---|
| PEG, 8K | Spectrum | 0.0% | 0.0% | 0.0% | 15.2% |
| Ketamine | Ketamine Hydrochloride | 9.1% | 8.3% | 9.1% | 9.1% |
| Polyacrylic Acid | Carbopol 974 NF | 0.0% | 0.0% | 7.6% | 0.0% |
| Mg Stearate | Spectrum | 0.4% | 0.4% | 0.4% | 0.4% |
| Total | | 100.0% | 100.0% | 100.0% | 100.0% |

Example 6

In Vivo Performance of the Neuro-Attenuating Ketamine Tablet Formulations of the Present Invention Pharmacokinetics of the KTM-2 formulation described herein was tested in beagle dogs. In particular, one tablet of the formulation KTM-2 was administered orally with 10 ml of water to one male and one female dog that had been fasted for 12 h before administration.

The blood samples were drawn at time points 0, 0.5, 1, 2, 4, 8, and 24 h. Ketamine and norketamine were quantified in plasma using LC/MS/MS method (Agilent 1200/AB SCIEX 4000 QTRAP instrumental setup) following the general procedure as described by Nettoa et al. (Biomed. Chromatogr., 2011); using the related analytical standards of ketamine and norketamine purchased from Sigma-Aldrich.

Figure 5:
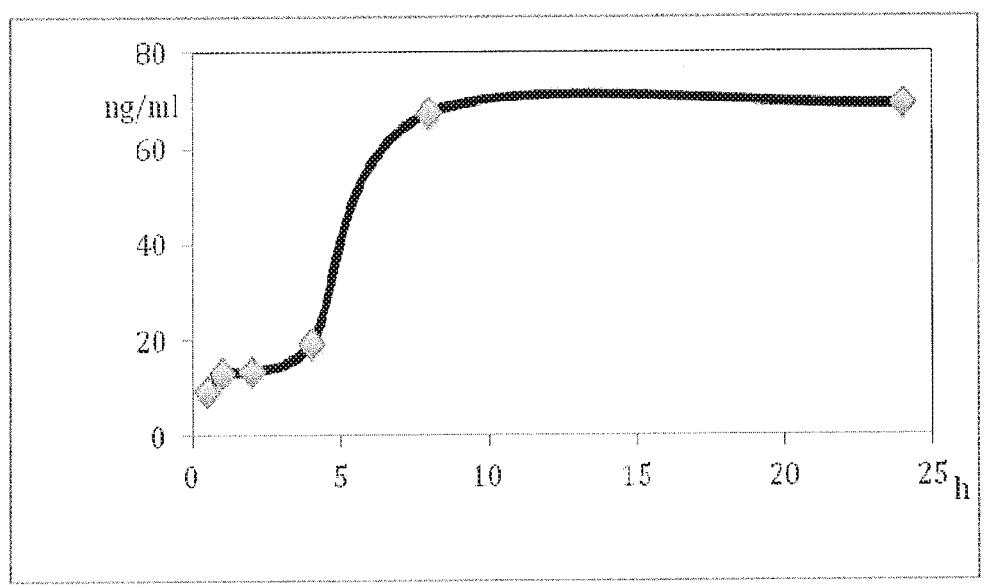
FIG. 5 is a graphical depiction of the ketamine concentration vs. time in the blood of beagle dogs after administration of tablet KTM-2.

The dogs tolerated the drug well with no observed physiological or behavioral side effects. The study showed a steady release of the drug from the matrix that is maintained for a 24 h period, with a total ketamine/norketamine concentration being within therapeutically relevant levels and no detected concentration spikes. A graph of the combined ketamine/norketamine plasma concentrations (in two dogs) vs. time is shown in FIG. 5.

This experiment confirms good in vitro-vivo correlations and validates the general pathways outlined herein related to the development and preparation of formulations of the present invention, e.g., suitable for human clinical trials.

Example 7

Enantioselective Synthesis of Deuterated Norketamine

Scheme 1

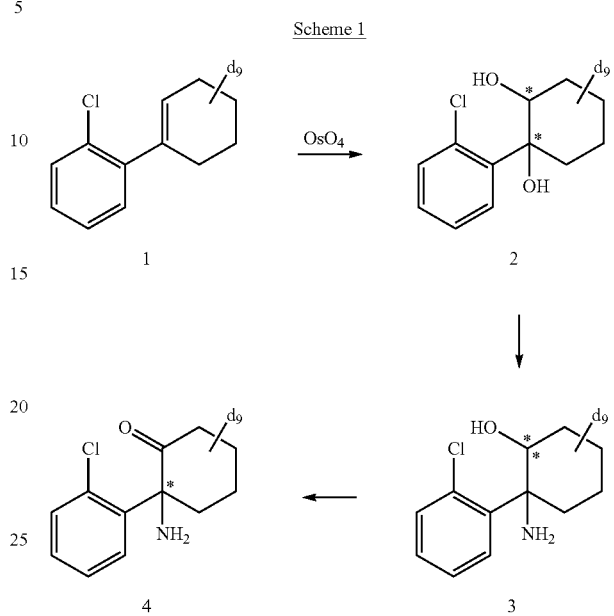

The synthesis is conducted following a reaction sequence as described by Bierman et al., 2011 for non-deuterated material (Scheme 1). The starting 2-chlorophenyl-1-cyclohexene-$d_{10}$ 1 is prepared from cycloxene-$d_{12}$ that is obtained by dehydration of a commercially available cyclohexanol-$d_{10}$ (CDN Isotopes). In the first step, 2-chlorophenyl-1-cyclohexene is dihydroxylated by osmium tetraoxide modified with hydroquinine 1,4-phthalazinediyl diether using Sharpless asymmetric synthesis (Kolb, 1994) to yield (−)-(1S, 2S)-1-(2-chlorophenyl)cyclohexane-1,2-diol 2 in 90% yield and with 85% ee after crystallization from n-hexane. In the second step, compound 2 is converted to (−)-(1S, 2S)-1-amino-1-(2-chlorophenyl)cyclohexane-2-ol 3, with 95% ee and 79% yield by the Ritter transformation (Senanayake et al., 1996). In the third step, a modified Jones oxidation (Yang et al., 1985) of 3 leads to (S)-2-amino-2-(2-chlorophenyl)cyclohexanone ((+)-S-norketamine) 4 (Parcell, 1981). The chiral purity is ee 99% determined by chiral HPLC. The specific rotation of the free S-norketamine base is measured to be $[a]D+3.2°$ (c=2, EtOH). NMR and MS-spectroscopy confirms the identity of the products.

Example 8

Nonstereoselective Synthesis of Deuterated Norketamine

Scheme 2

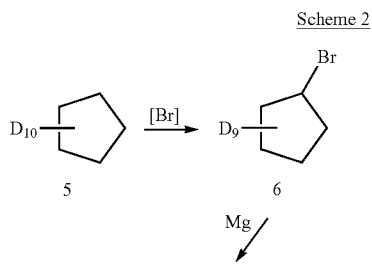

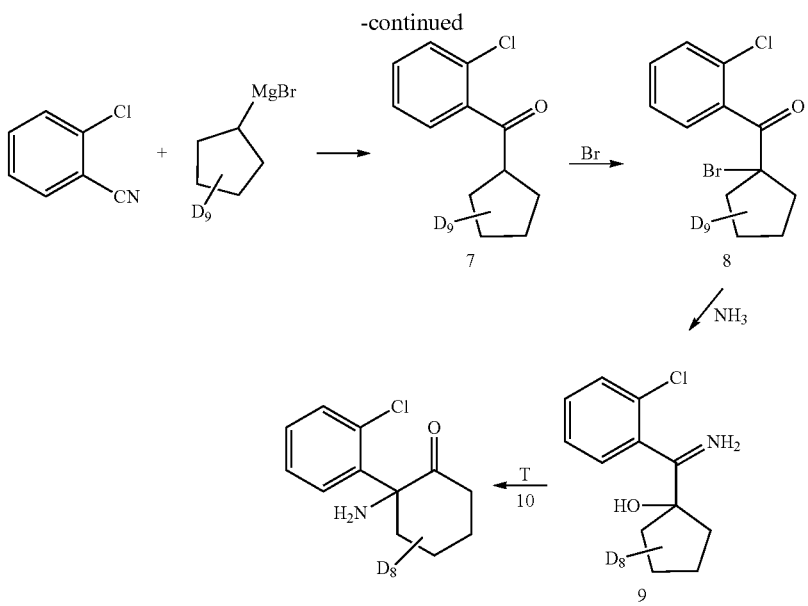

The synthesis was conducted following a general reaction sequence as described by Parcell, 1981 (Scheme 2). In the first step, o-chlorobenzonitrile is reacted with cyclopentyl magnesium bromide (obtained by bromination of the commercially available cyclopentane-$d_{10}$ to give cyclopentane bromide-$d_9$ 6 and then by Grignard reaction) to give deuterated 1-chlorophenyl-cyclopentyl ketone 7, followed by alpha-bromination of the ketone to give 8, and then reaction with ammonia to form an alpha-hydroxy imine 1-hydroxy-cyclopentyl-(1-chlorophenyl)-ketone-N-methylimine 9. Thermal rearrangement with ring expansion of 9 leads to racemic norketamine 10 with overall yield of 70%. NMR and MS-spectroscopy confirmed the identity of the products.

Example 9

Synthesis of Deuterated Norketamine by Deuterium Exchange

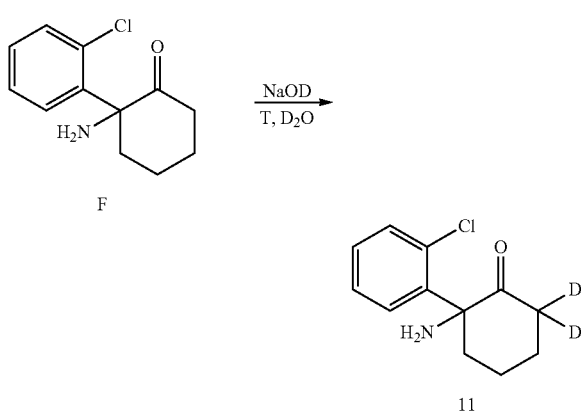

The hydrogen atoms or the methylene group adjacent to the carbonyl group are known to undergo a facile proton exchange. Consequently, deuterium exchange in norketamine may be investigated by heating in a heavy water solution (0.01 M) at 80° C. in presence of NaOD (0.1 M) and following the reaction by proton NMR. The progress of the reaction is followed by alterations in the multiplet signal at ca. 2.3 ppm that corresponds to the carbonyl methylene group. In 30 minutes, a simplification of the fine structure is observed along with a decrease of the signal integral intensity consistent with the lost of two proton. After heating at 80-90° C. for 24 h, an extent of the deuteration is 70-80%. Prolonged reaction time past 24 h didn't result in the increased yields and accumulated degradation impurities. In optimized conditions, the deuterium exchange is conducted in the mixtures of deuterated methanol or ethanol with deuterated water, with alcohol fraction constituting 40-90% of the mixture. In these conditions, even at room temperature the hydrogen-deuterium exchange is found to be very rapid and complete—the proton NMR spectra recorded immediately after addition of the base shows a complete disappearance of the target protons and conservation of the rest of the spectrum. A deuterated norketamine 11 is obtained by chloroform extraction of the basic reaction mixture in a quantitative yield after evaporation of the solvent (Scheme 3). Deuterated norketamine is stable towards hydrogen exchange at neutral and acidic pH. We observed no changes in the NMR spectra of 11 in deuterated chloroform upon treating the solution in situ with small amounts of water, hydrochloric or acetic acid.

In an alternative procedure, norketamine hydrochloride (20 mg) was placed in a 5 ml screw-cap vial and dissolved in 1 ml of $CD_3OD$ with magnetic stirring. To this solution, $D_2O$ (0.2 ml) was added followed by 40% NaOD in deuterated water (0.1 ml). The reaction mixture was stirred at ambient temperature for 10 min and evaporated to dryness at reduced pressure. The residue was treated with $D_2O$ (1 ml) and extracted with 3×2 ml of ethyl acetate. After drying the ethyl acetate extract with $Na_2SO_4$, the solvent was evaporated to yield 18 mg (90%) of the deuterated norketamine 11 as a white solid. $^1H$ NMR ($CDCl_3$) d 7.7 (dd, J=7.8, 1.7 Hz, 1H), 7.4-7.3 (m, 2H), 7.3-7.2 (m, 1H), 2.8-2.7 (m, 1H), 2.1-2.0 (m, 1H), 1.9-1.7 (m, 3H), 1.7-1.6 (m, 1H). LC/MS, m/z 224 ($M^+$+1).

Example 10

Nonstereoselective Synthesis of Norketamine 10 using Cyclohexanone-d$_8$

Alternative synthesis of the deuterated norketamine compound 11 is conducted using a scheme reported by Sulake et al. (2011) that starts with bromochlorobenzene which is converted into the Grignard reagent in THF and reacted with commercially available cyclohexanone-d$_8$ (CDN isotopes) to give 1-(2-chlorophenyl)cyclohexanol. Dehydration of cyclohexanol with p-TSA in benzene provides 1-(2-chlorophenyl)cyclohexene in quantitative yield followed by its epoxidation with m-chloroperoxy benzoic acid (m-CPBA) that leads to 1-(2-chlorophenyl)-7-oxabicyclo[4.1.0]heptane. Regioselective ring opening of epoxide with HBr provides bromohydroxy intermediate that is followed by oxidation with pyridinium chlorochromate (PCC) in DCM leading to the related keto-compound. Nucleophilic exchange of the bromide with and azide group and reduction of azide using Staudinger condition gives norketamine compound 11 in overall 60% yield.

Example 11

Metabolic Activity of the Deuterated Nor-Ketamines In Vitro Deuterated Norketamines 11 and 12 have the below Structures.

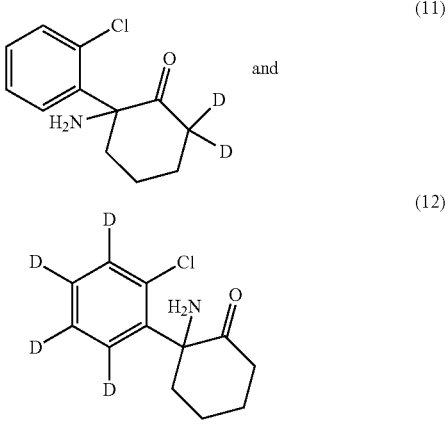

Deuterated norketamine 11 (10 microl of 2 micro M solution) was incubated in 200 microliter of the medium that consists of 100 mg rat liver microsomes, NADPH regenerating system (1 mM NADP, 1 unit/ml of isocitrate dehydrogenase, 5 mM isocitric acid, 5 mM magnesium chloride), and 25 mM of phosphate buffer (pH 7.4). The reaction is terminated at different time points (0 to 60 min) by the addition of 300 microl of acetonitrile. For the analyses of metabolites, the precipitated salts and proteins are spun out on a centrifuge, the residual solution diluted with 300 microl of water and injected into the LC/MS (Agilent 1200 system interfaced with an ABS Sciex 4000 QTRAP LC/MS/MS Mass Spectrometer).

Metabolic transformation of norketamine yields multiple products related to hydroxylation at different position of the cyclohexyl and aryl group, as well as dehydrogenation to dehydro-norketamine, some of which are eliminated in vivo as glucuronides. The metabolic stability of norketamine may be estimated by evaluating the rate of disappearance of the main peak.

We observed an about 80% increase in the half-life for compound 11 compared to the non-deuterated norketamine. The half-life of the tetra-deuterated norketamine with deuterium substitutions at the phenyl ring, compound 12, was found to be similar to the non-deuterated norketamine. The data are shown in the FIG. 6. The collective kinetic deuterium isotope effect (the reaction rate decrease for deuterated vs. non-deuterated analogue) is expected to be more substantial, at >100%, for the fully deuterated cyclohexanone material.

Example 12

Pharmacokinetics of the Deuterated Nor-Ketamines In Vivo

Pharmacokinetics of the deuterated norketamines is studied in rats. A groups of 3 Wistar female rats (200-250 g) with surgically inserted jugular vein catheter (Charles River, Andover, Mass.) are fasted for 12 h and then given a mixture of 0.8 mg/kg each of norketamine and deuterated norketamine compound 11 solution by an injection into the tail vein. The blood is drawn at time points 0, 15, 30, 60 min, and 2, 4, 6, 8, and 24 h and resulting plasma analyzed concurrently for norketamine and deuterated norketamine compound 11 using LC/MS spectroscopy (limit of quantitation ca. 1 mg/ml for each analyte). The experimental data are shown in the FIG. 7. The terminal half-lives are calculated by fitting the data points using a WinNonLin software package. The terminal half-life $T_{1/2}$ for norketamine is found to be at 2.07 h and for the bis-deuterated compound 11 at 2.83 h, ca., 40% increase indicative of a significantly slower metabolic transformation rendered by deuterium substitution on compound 11.

We expect further prolongation of the terminal half-life for the fully deuterated compound 10 to over 3 h consistent with slower elimination of norketamine due to the kinetic deuterium isotope effects related metabolic oxidation to hydroxylated products.

Example 13

NMDA Receptor Activity of the Deuterated Norketamine

We measured electrophysiological functional response to the deuterated compound 10 by the patch clamp method in cultural hippocampal rat neurons to confirm that NMDA receptor activity is not altered by deuterium substitution. We use racemic ketamine as a reference standard that displays a receptor inhibition with $IC_{50}$ of 2.2 µM that is within the range of the literature data. Norketamine is a weaker inhibitor with $IC_{50}$ of 14.7 µM, again in agreement with the previously reported data. Bis-deuterated norketamine compound 11 has $IC_{50}$ of 25.9 µM in this assay, very close to the non-deuterated norketamine.

We expect that fully deuterated compound 10 will have a full functional activity in the concentration range similar to the bis-deuterated norketamine compound 10 and non-deuterated norketamine.

REFERENCES

1. Correll E. G., Jahangir Maleki, J., Gracely E. J., Muir J. J., Harbut R. E. Sub-anesthetic Ketamine Infusion Therapy: A Retrospective Analysis of a Novel Therapeutic Approach to Complex Regional Pain Syndrome, *Pain Medicine,* 5(2004)263-275.

2. Zarate Jr. C. A., Brutsche N. E., Ibrahim L., Franco-Chaves J., Diazgranados N., Cravchik A., Selter J., Marquardt C. A., Liberty V., Luckenbaugh D. A. Replication of Ketamine's Antidepressant Efficacy in Bipolar Depression: A Randomized Controlled Add-On Trial, *Biol. Psych.,* 71(2012)939-946.

3. Hertle D. N, Dreier J. P., Woitzik J., Hartings J. A., Bullock R., Okonkwo D. O., Shutter L. A., Vidgeon S., Strong A. J., Kowoll C., Dohmen C., Diedler J., Veltkamp R., Bruckner T., Unterberg A. W., Sakowitz O. W. Effect of Analgesics and Sedatives on the Occurrence of Spreading Depolarizations Accompanying Acute Brain Injury, *Brain,* 135(2012)2390-8.

4. Synowiec A. S., Singh D. S., Yenugadhati V., Valeriano J. P., Schramke C. J., Kelly K. M. Ketamine Use in the Treatment of Refractory Status Epilepticus, *Epilepsy Res.* 105(2013)183-8.

5. Blonk M. I., Koder B. G. van den Bemt P. M. L. A., Huygen F. J. P. M. Use of Oral Ketamine in Chronic Pain Management: A Review, *Eur. J Pain,* 14(2010)466-472.

6. Chong C., Schug S. A., Page-Sharp M., Jenkins B., Ilett K. F. Development of a Sublingual/Oral Formulation of Ketamine for Use in Neuropathic Pain. Preliminary Findings from a Three-Way Randomized, Crossover Study, *Clin. Drug Invest.* 2009, 29(5)317.

7. Yanagihara Y., Ohtani M., Matsumoto M., Kariya S., Uchino K., Hiraishi T., Ashizawa N., Aoyama T., Yamamura Y., Iga T. Preparation of Ketamine Tablets for Treatment of Patients with Neuropathic Pain, *Yakugaku Zasshi,* 1999, 119(12)980-7.

8. Yanagihara Y, Ohtani M, Kariya S, et al. Plasma Concentration Profiles of Ketamine and Norketamine After Administration of Various Ketamine Preparations to Healthy Japanese Volunteers. *Biopharm. Drug Dispos.* 2003, 24: 37-43.

9. Analgesic Immediate and Controlled Release Pharmaceutical Compositions, U.S. Pat. No. 6,194,000 B1.

10. J. D. Nettoa, G. C. Muske, G. L. Makerb, and Robert D. Trengove, Liquid chromatography tandem mass spectrometry for the simultaneous quantitative analysis of ketamine and medetomidine in ovine plasma, *Biomed. Chromatog.,* 2011, 25, 1374-1380.

11. M. Biermann, K. I. Hardcastle, N. V. Moskalev, P. A. Crooks, (2011), *Acta Cryst.,* E67, p. 936, 12. Kolb, H. C., VanNieuwenhze, M. S. and Sharpless, B. K., (1994). *Chem. Rev.,* 94, p. 2483-2547.

13. Parcell, R. F. and Sanchez, P. J. (1981), *J. Org. Chem.* 46, p. 5055-5060.

14. Senanayake, C. H., Larsen, R. D., DiMichele, L. M., Liu, J., Toma, P. H., Ball, R. G., Verhoeven, T. R. and Reider, P. J. (1996), *Tetrahedron Asymmetry,* 7, p. 1501-1506.

15. Sulake, R. S., Chen, C., Lin, H.-R. and Lua, A-C., (2011), *Bioorg. Med. Chem. Let.,* p. 5719.

Incorporation by Reference

The entire contents of all patents, published patent applications and other disclosures cited herein are hereby expressly incorporated herein in their entireties by reference.

Equivalents

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments (e.g., such as particular pain indications); as such, each member of the list should be considered a separate embodiment.

What is claimed is:

1. A substantially pure, isotopically-enriched compound of formula (I):

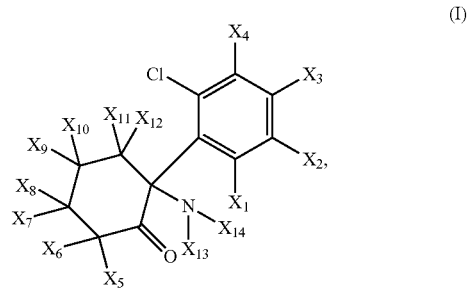

or a pharmaceutically acceptable salt thereof, wherein $X_1$, $X_2$, $X_3$, $X_4$, $X_5$, $X_6$, $X_7$, $X_8$, $X_9$, $X_{10}$, $X_{11}$, $X_{12}$, $X_{13}$, and $X_{14}$ are each independently selected from the group consisting of hydrogen and deuterium, and wherein at least one of $X_1$, $X_2$, $X_3$, $X_4$, $X_5$, $X_6$, $X_7$, $X_8$, $X_9$, $X_{10}$, $X_{11}$, $X_{12}$, $X_{13}$, and $X_{14}$ is deuterium, and when each of $X_1$, $X_2$, $X_3$, and $X_4$ is deuterium, then at least one of $X_5$, $X_6$, $X_7$, $X_8$, $X_9$, $X_{10}$, $X_{11}$, $X_{12}$, $X_{13}$, and $X_{14}$ is deuterium.

2. The compound of claim 1, wherein each of $X_1$, $X_2$, $X_3$, and $X_4$ is hydrogen, or a pharmaceutically acceptable salt thereof.

3. The compound of claim 1, wherein $X_5$, $X_6$, $X_7$, $X_8$, $X_9$, $X_{10}$, $X_{11}$, and $X_{12}$ are deuterium, or a pharmaceutically acceptable salt thereof.

4. The compound of claim 1, having a structure that is

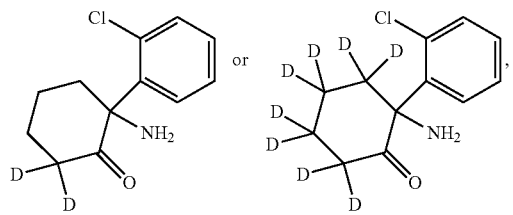 [SMILES: [2H]C1([2H])CCCC(N)(c2ccccc2Cl)C1=O ; [2H]C1([2H])C(=O)C(N)(c2ccccc2Cl)C([2H])([2H])C([2H])([2H])C1([2H])[2H]]

or a pharmaceutically acceptable salt thereof.

5. A pharmaceutically acceptable salt of an isotopically-enriched compound according to formula (I):

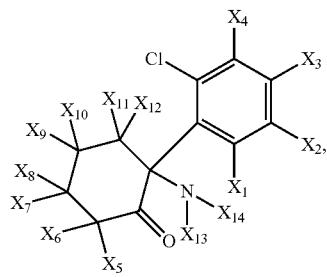

(I)

wherein
X$_1$, X$_2$, X$_3$, X$_4$, X$_5$, X$_6$, X$_7$, X$_8$, X$_9$, X$_{10}$, X$_{11}$, X$_{12}$, X$_{13}$, and X$_{14}$ are each independently selected from the group consisting of hydrogen and deuterium,
and wherein
at least one of X$_1$, X$_2$, X$_3$, X$_4$, X$_5$, X$_6$, X$_7$, X$_8$, X$_9$, X$_{10}$, X$_{11}$, X$_{12}$, X$_{13}$, and X$_{14}$ is deuterium.

6. The pharmaceutically acceptable salt of claim 5, wherein the compound of formula (I) is at a purity of at least 50% by weight of the total amount of isotopologues of formula (I) present.

7. A pharmaceutical composition comprising
(a) a compound of formula (I) according to claim 1, or a pharmaceutically acceptable salt thereof, or a pharmaceutically acceptable salt of a compound of formula (I) according to claims 5; and
(b) a pharmaceutically acceptable excipient.

8. A method of inhibiting N-methyl-d-aspartate (NMDA) receptor activity, said method comprising: contacting the NMDA receptor of a subject with an effective amount of the compound of formula (I) according to claim 1.

9. A method of treating a disease or condition in a subject comprising the step of administering said subject an effective amount of a compound of formula (I) according to claim 1,
wherein the disease or condition is levodopa-induced dyskinesia; dementia, tinnitus, depression, pain, agitation resulting from or associated with Alzheimer's disease, pseudobulbar effect, autism, Bulbar function, anxiety, Alzheimer's disease, schizophrenia, diabetic neuropathy, suicidality, post-traumatic stress disorder, treatment resistant depression, major despressive disorder, generalized anxiety disorder, neuropathic pain, acute pain, chronic pain, schizophrenia, a mood disorder, substance induced psychosis, major depressive disorder, bipolar disorder, bipolar depression, anxiety, or obsessive compulsive disorder.

10. An isolated, deuterium-enriched neuro-attenuating norketamine (NANKET) compound or a pharmaceutically acceptable salt thereof.

11. The isolated, deuterium-enriched neuro-attenuating norketamine (NANKET) compound of claim 10, wherein the compound has the following structure:

or a pharmaceutically acceptable salt thereof, or

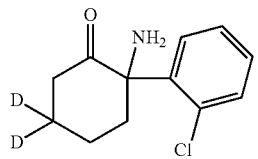

or a pharmaceutically acceptable salt thereof, or

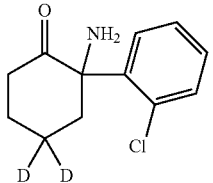 [SMILES: [2H]C1([2H])CCC(=O)C(N)(c2ccccc2Cl)C1]

or a pharmaceutically acceptable salt thereof, or

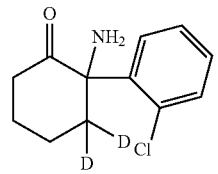 [SMILES: [2H]C1([2H])CCCC(=O)C1(N)c1ccccc1Cl]

or a pharmaceutically acceptable salt thereof, or

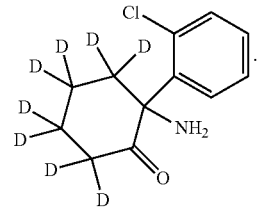 [SMILES: [2H]C1([2H])C(=O)C(N)(c2ccccc2Cl)C([2H])([2H])C([2H])([2H])C1([2H])[2H]]

or a pharmaceutically acceptable salt thereof, or
a compound is selected from a group of compounds having a Formula I-A structure:

(I-A)

or a pharmaceutically acceptable salt thereof,
wherein
X$_1$, X$_2$, X$_3$, X$_4$, X$_6$, X$_7$, X$_8$, X$_9$, X$_{10}$, X$_{11}$, X$_{12}$, X$_{13}$, and X$_{14}$ are each independently selected from the group consisting of hydrogen and deuterium, and wherein at least one of $X_1$, $X_2$, $X_3$, $X_4$, $X_6$, $X_7$, $X_8$, $X_9$, $X_{10}$, $X_{11}$, $X_{12}$, $X_{13}$, and $X_{14}$ is deuterium, or a compound or any salt thereof is selected from a group of compounds having a Formula I-B structure:

(I-B)

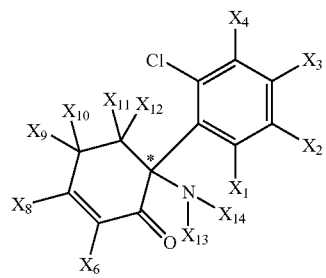

or a pharmaceutically acceptable salt thereof, wherein $X_1$, $X_2$, $X_3$, $X_4$, $X_6$, $X_8$, $X_9$, $X_{10}$, $X_{11}$, $X_{12}$, $X_{13}$, and $X_{14}$ are each independently selected from the group consisting of hydrogen and deuterium, and wherein at least one of $X_1$, $X_2$, $X_3$, $X_4$, $X_6$, $X_8$, $X_9$, $X_{10}$, $X_{11}$, $X_{12}$, $X_{13}$, and $X_{14}$ is deuterium.

12. The isolated, deuterium-enriched neuro-attenuating norketamine (NANKET) compound of claim 10, wherein the compound is selected from a group compounds consisting of those of the following structures 11 through 101 or any pharmaceutically acceptable salt thereof:

11

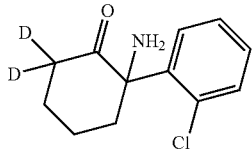

13

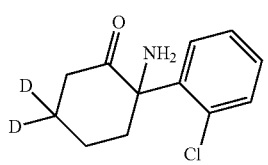

14

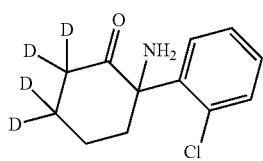

15

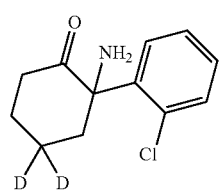

16

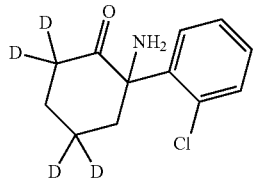

17

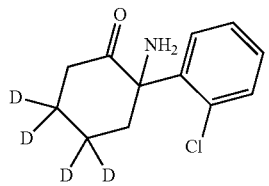

18

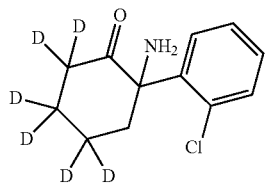

19

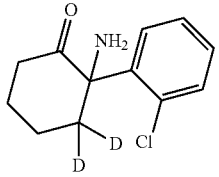

20

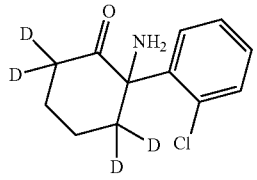

21

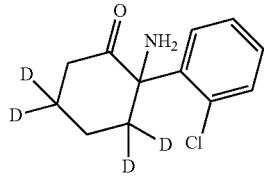

22

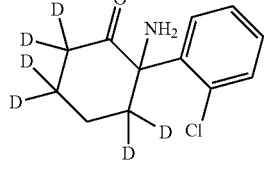

23

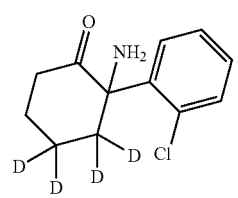

-continued

39
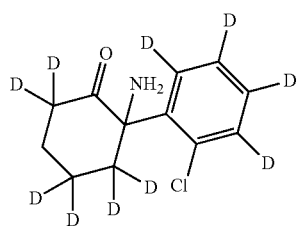
40
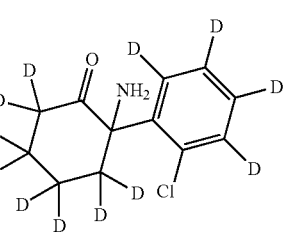
41
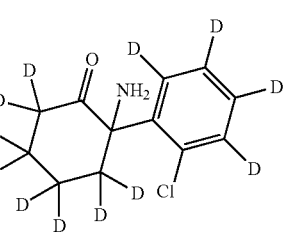
42
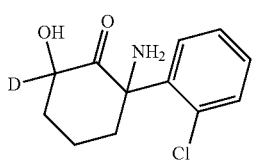
43
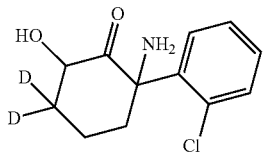
44
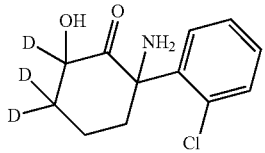
45
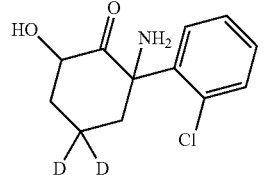
46
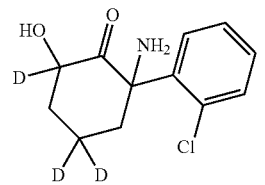
47
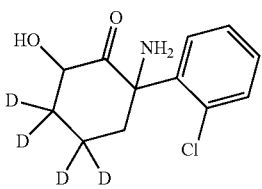
48
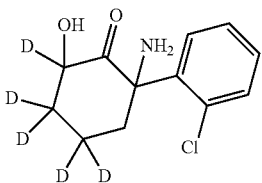
49
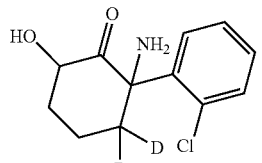
50
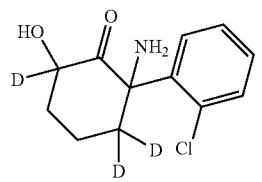
51
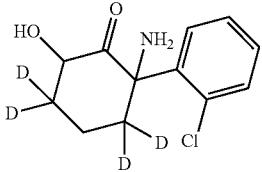
52
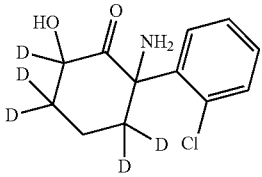
53
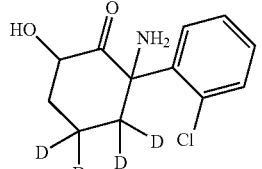
54
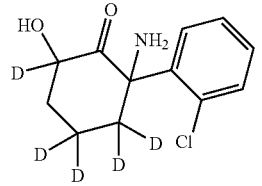

55
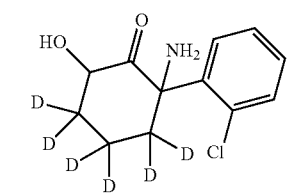
56
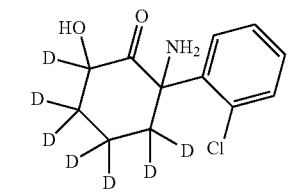
57
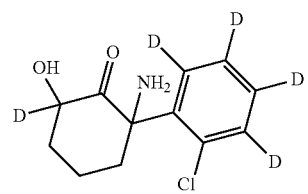
58
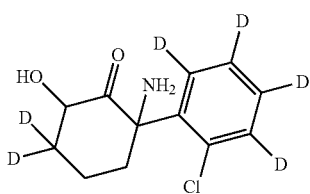
59
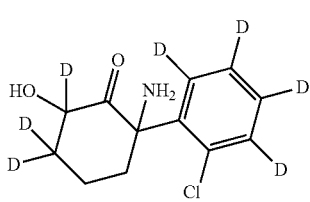
60
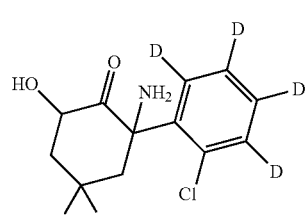
61
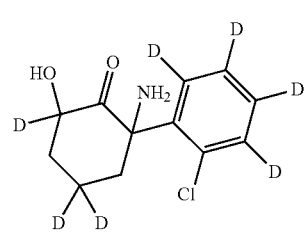
62
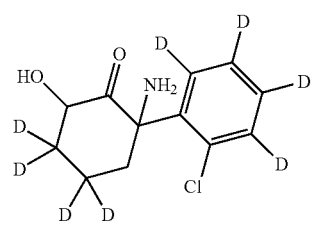
63
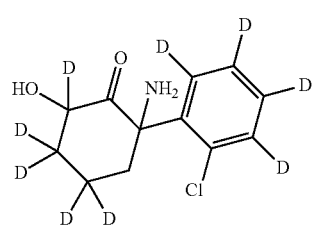
64
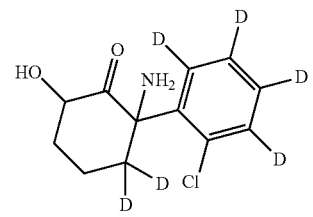
65
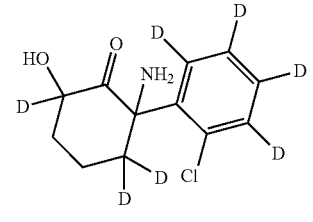
66
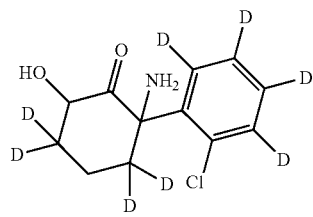
67
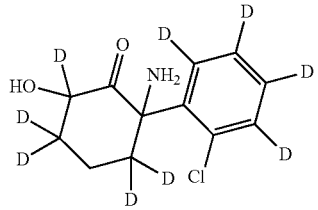
68
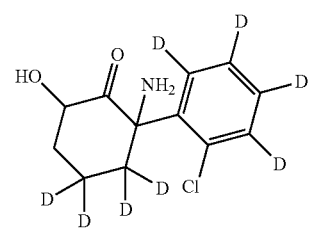

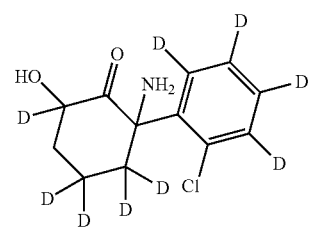 69
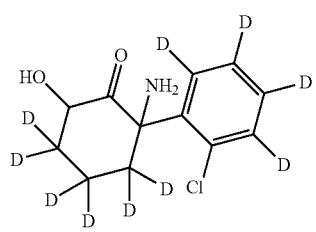 70
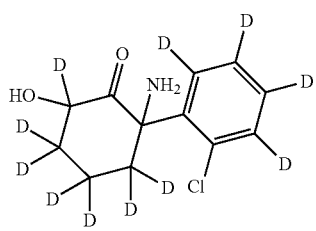 71
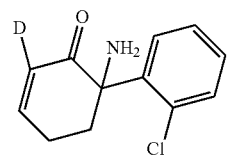 72
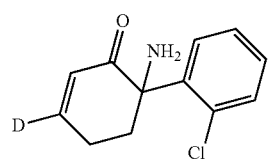 73
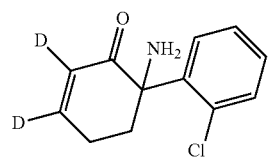 74
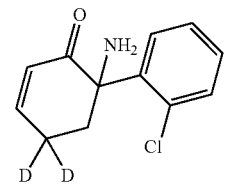 75
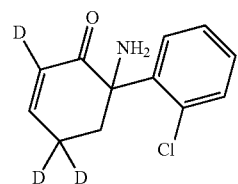 76
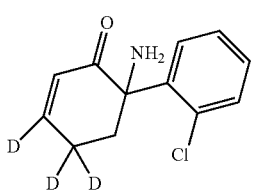 77
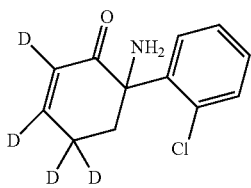 78
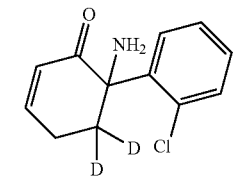 79
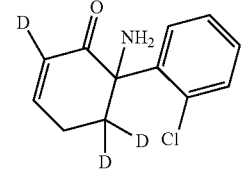 80
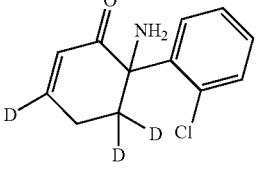 81
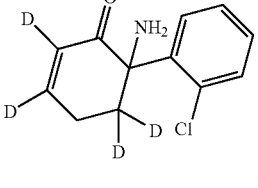 82
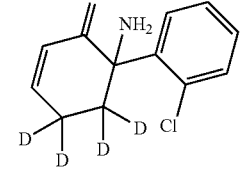 83
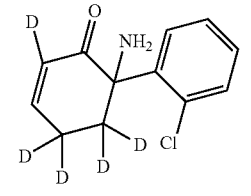 84

85 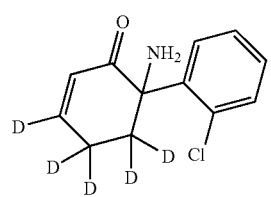
86 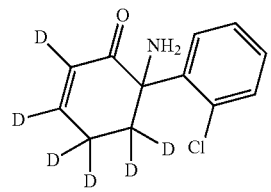
87 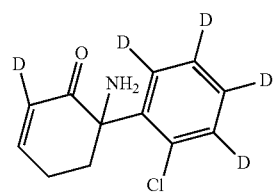
88 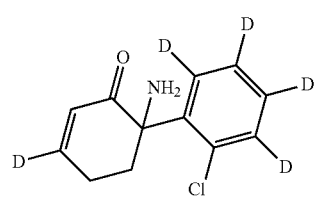
89 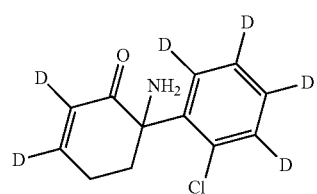
90 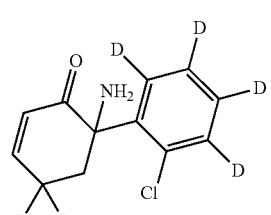
91 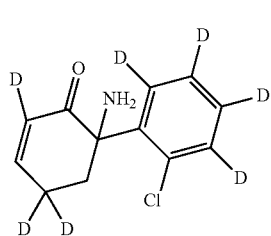
92 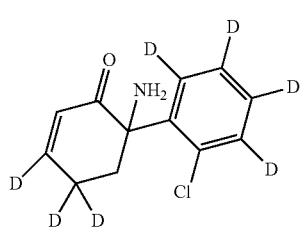
93 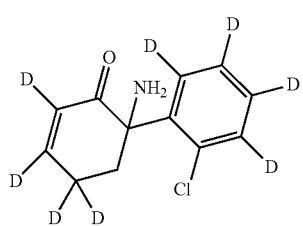
94 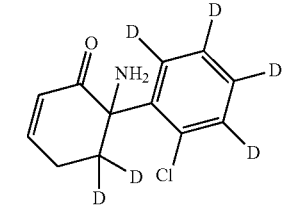
95 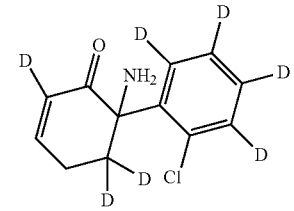
96 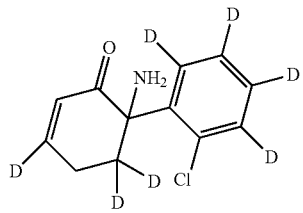
97 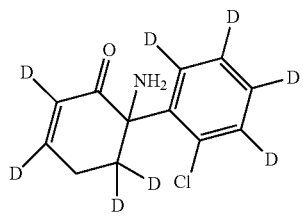
98 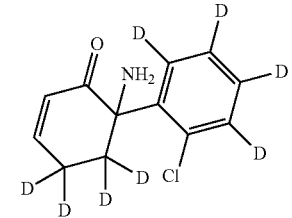

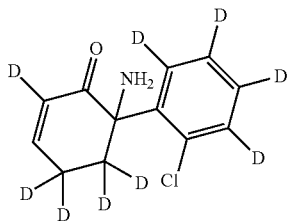

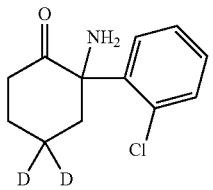 [SMILES: [2H]C1([2H])CCC(=O)C(N)(c2ccccc2Cl)C1]

or a pharmaceutically acceptable salt thereof, or

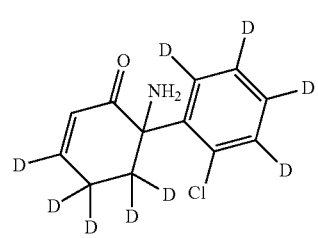

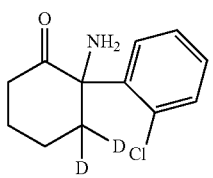 [SMILES: [2H]C1([2H])CCCC(=O)C1(N)c1ccccc1Cl]

or a pharmaceutically acceptable salt thereof, or

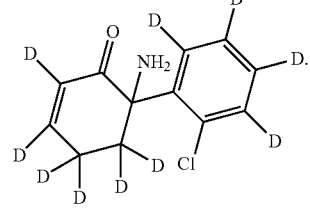

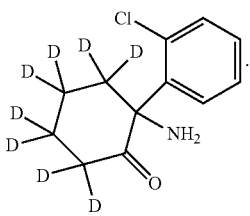 [SMILES: [2H]C1([2H])C(=O)C(N)(c2ccccc2Cl)C([2H])([2H])C([2H])([2H])C1([2H])[2H]]

or a pharmaceutically acceptable salt thereof.

15. An oral, modified-release pharmaceutical composition for oral administration to a subject for treating the subject diagnosed with, suffering from or susceptible to a disease, disorder or condition, such as those for which ketamine treatment may be indicated, considered or recommended, wherein the subject is in need of treatment with said oral, modified-release pharmaceutical composition, said oral, modified-release pharmaceutical composition comprising:

(a) a drug selected from a group consisting of ketamine, a deuterium-enriched neuro-attenuating ketamine (NAKET) compound, norketamine, and/or a deuterium-enriched neuro-attenuating norketamine (NANKET) compound or a pharmaceutically acceptable salt thereof in an effective amount for treating, preventing and/or managing the disease, disorder, or condition in the subject; and (b) a pharmaceutically acceptable excipient;

whereby, upon oral administration of the modified-release pharmaceutical composition to the subject, a steady release of said drug from the modified-release pharmaceutical composition is maintained so that no neurologically toxic spike in the subject's plasma occurs during the release period of said drug from said pharmaceutical composition.

16. The oral, modified-release pharmaceutical composition of claim 15, wherein the drug has the following structure:

13. A synthetic composition of matter comprising deuterium-enriched neuro-attenuating norketamine (NANKET) compound or a pharmaceutically acceptable salt thereof.

14. The synthetic composition of matter of claim 13, wherein the deuterium-enriched neuro-attenuating norketamine (NANKET) compound has the following structure:

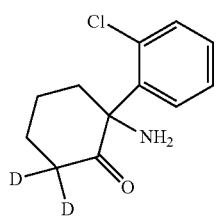 [SMILES: [2H]C1([2H])CCCC(N)(c2ccccc2Cl)C1=O]

or a pharmaceutically acceptable salt thereof, or

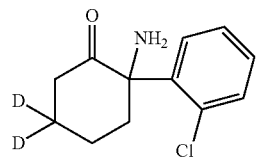 [SMILES: [2H]C1([2H])CCC(N)(c2ccccc2Cl)C(=O)C1]

or a pharmaceutically acceptable salt thereof, or

87

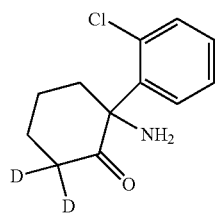

or a pharmaceutically acceptable salt thereof, or

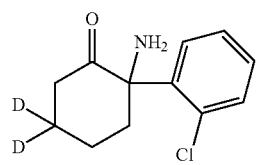

or a pharmaceutically acceptable salt thereof, or

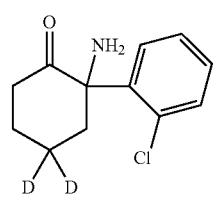 [SMILES: [2H]C1([2H])CCC(=O)C(N)(c2ccccc2Cl)C1]

or a pharmaceutically acceptable salt thereof, or

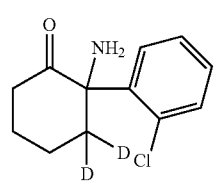 [SMILES: [2H]C1([2H])CCCC(=O)C1(N)c1ccccc1Cl]

or a pharmaceutically acceptable salt thereof, or

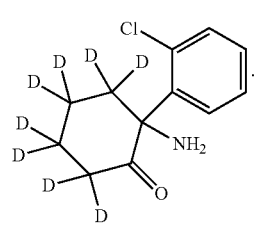

or a pharmaceutically acceptable salt thereof.

17. The oral, modified-release pharmaceutical composition of claim 15, wherein the drug is selected from a group of compounds consisting of the following structures 11 through 101 or any pharmaceutically acceptable salt thereof:

88

11
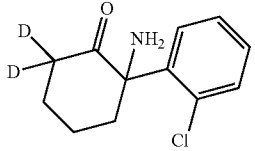

13
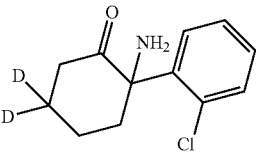

14
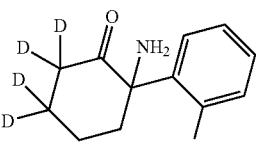

15
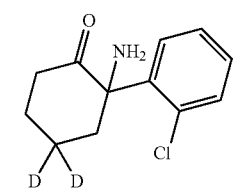

16
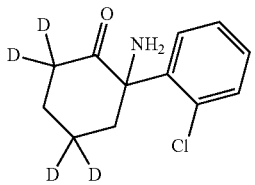

17
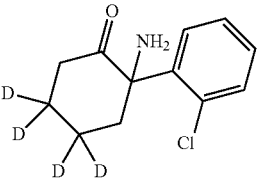

18
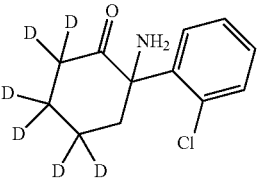

19
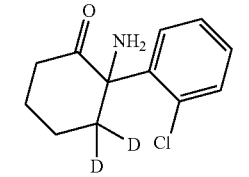

20
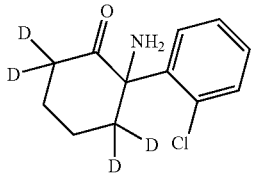

21
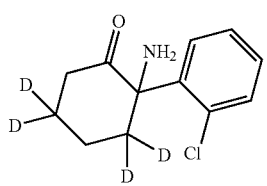
22
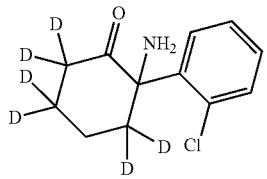
23
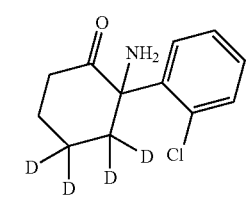
24
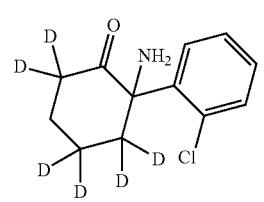
25
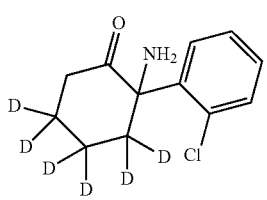
26
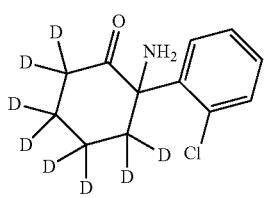
27
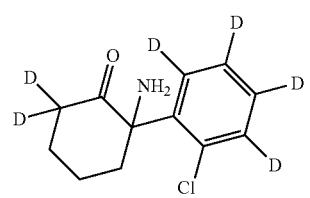
28
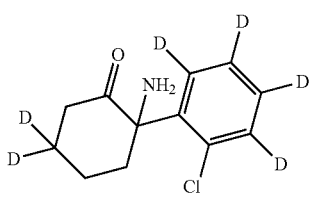
29
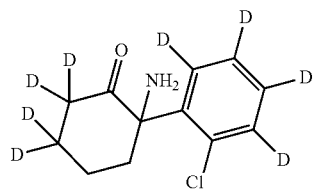
30
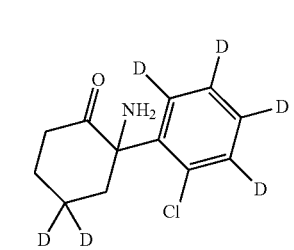
31
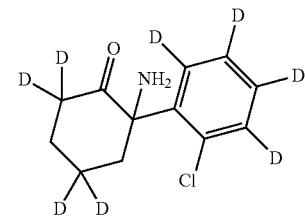
32
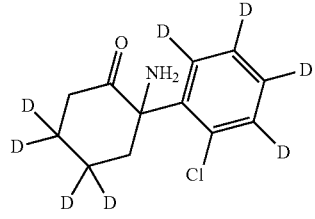
33
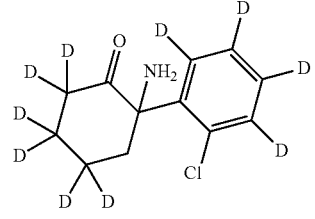
34
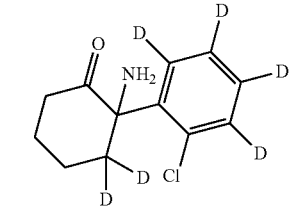
35
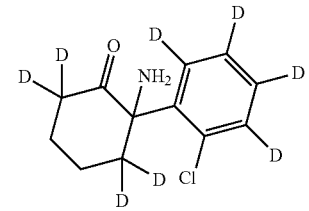

-continued
36
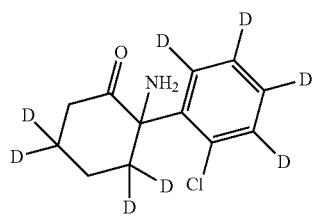
37
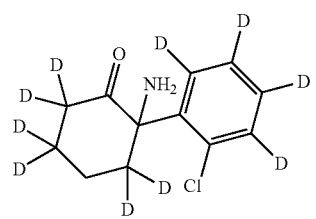
38
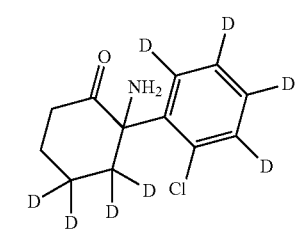
39
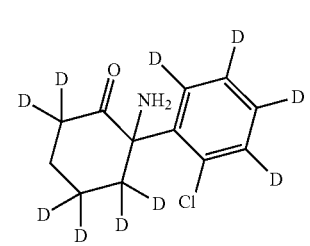
40
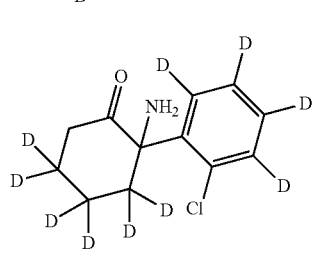
41
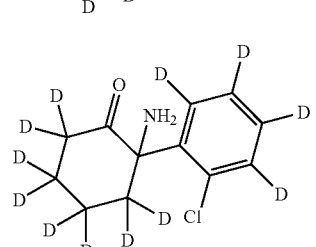
42
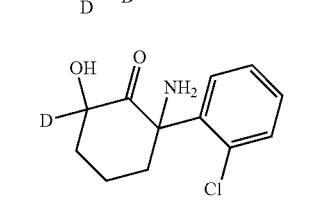
-continued
43
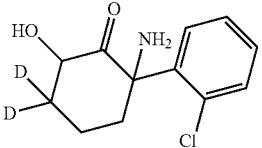
44
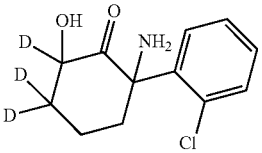
45
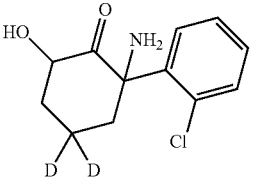
46
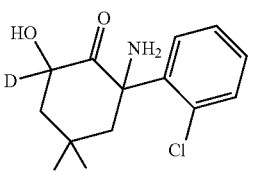
47
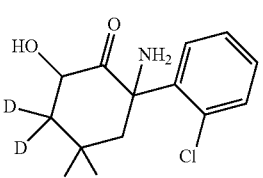
48
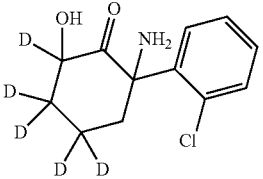
49
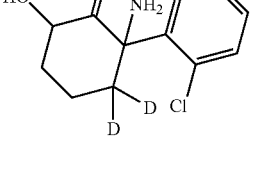
50
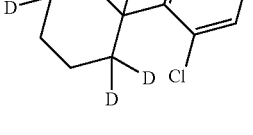

51
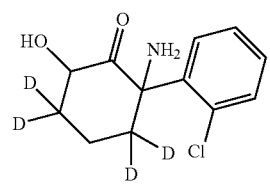
52
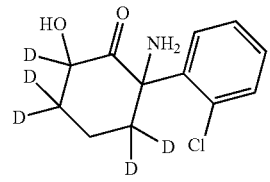
53
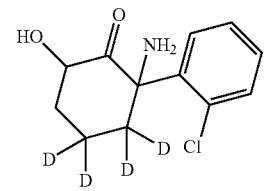
54
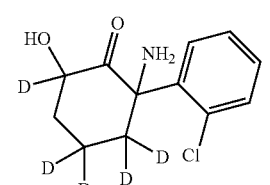
55
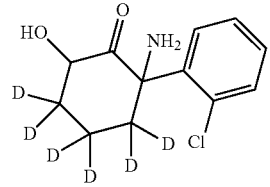
56
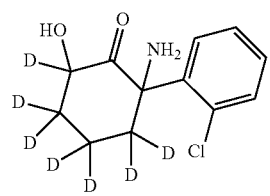
57
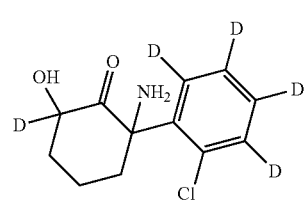
58
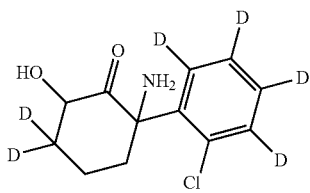
59
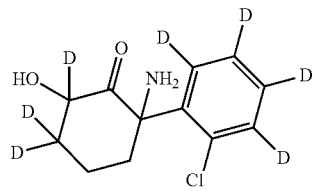
60
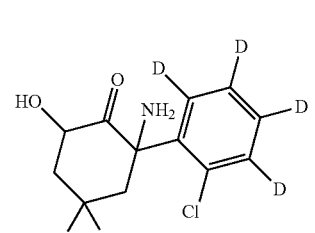
61
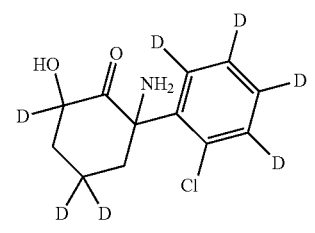
62
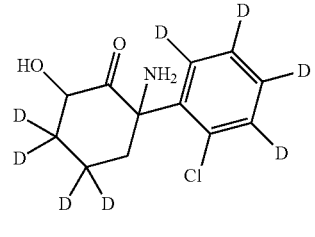
63
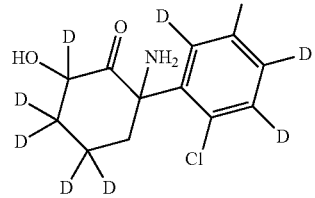
64
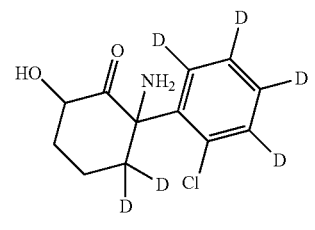
65
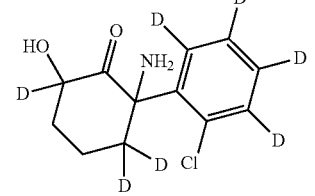

95
-continued
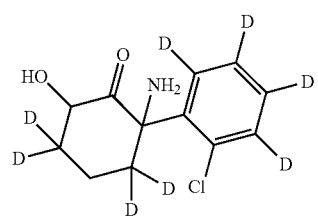
66
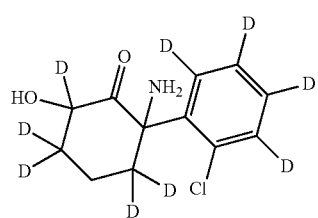
67
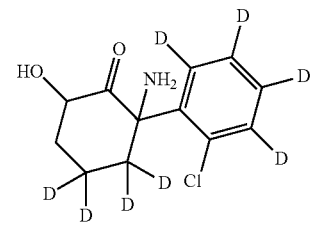
68
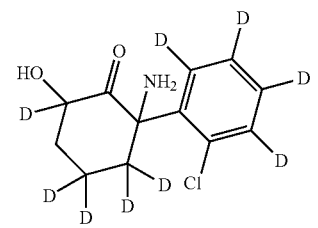
69
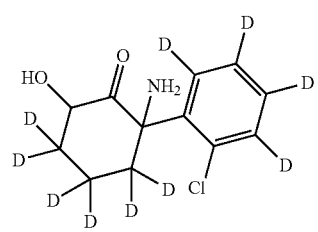
70
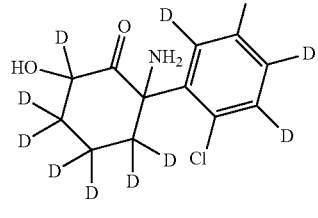
71
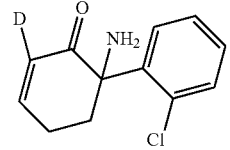
72
96
-continued
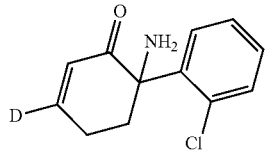
73
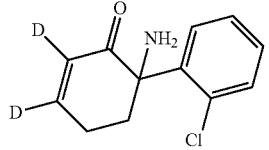
74
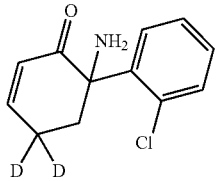
75
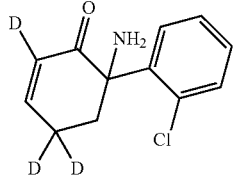
76
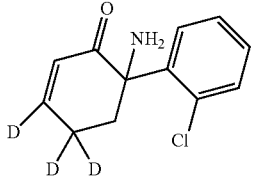
77
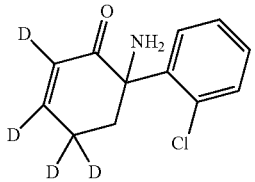
78
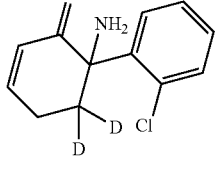
79
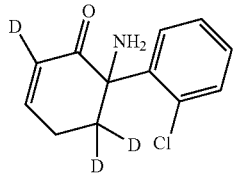
80

81
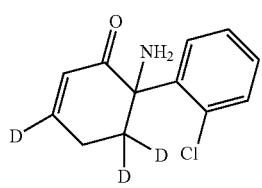
82
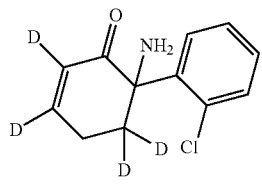
83
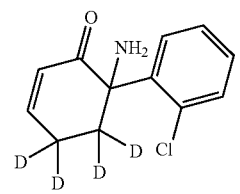
84
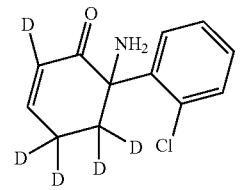
85
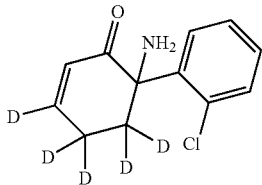
86
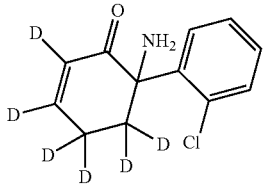
87
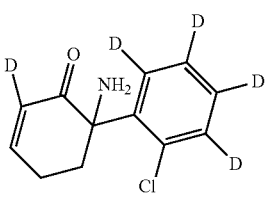
88
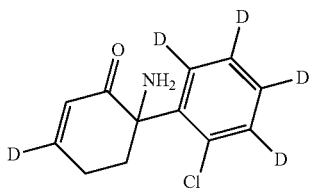
89
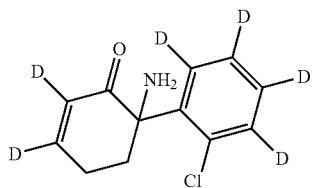
90
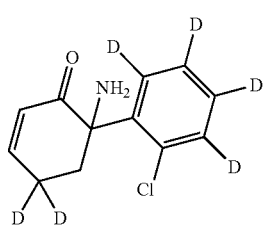
91
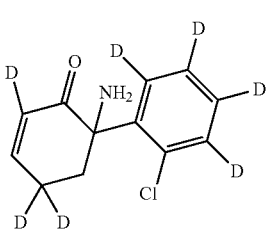
92
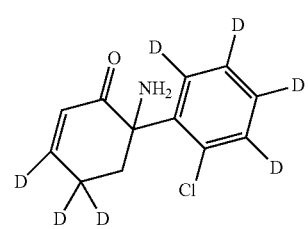
93
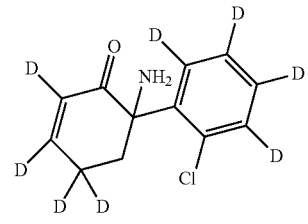
94
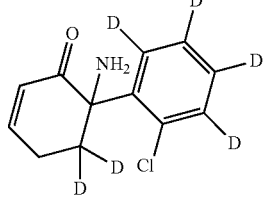
95
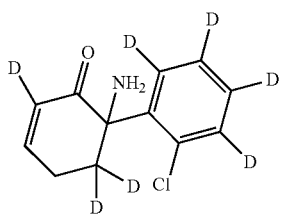

-continued

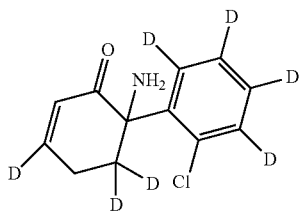
96

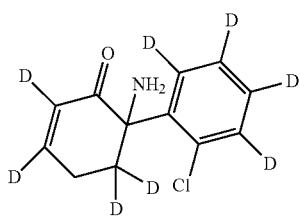
97

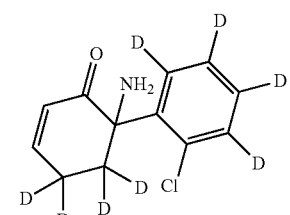
98

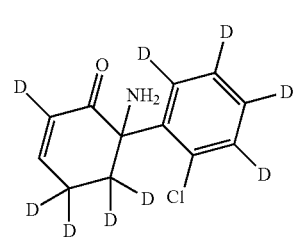
99

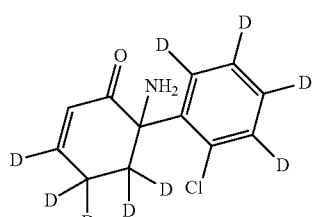
100

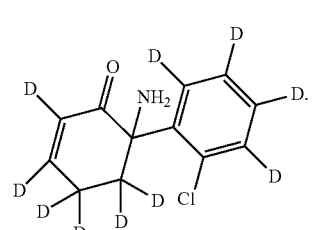
101

18. The oral, modified-release pharmaceutical composition of claim 15 wherein the drug is ketamine.

19. The oral, modified-release pharmaceutical composition of claim 15 wherein the drug is a deuterium-enriched neuro-attenuating ketamine (NAKET) compound.

20. The oral, modified-release pharmaceutical composition of claim 15 wherein the drug is norketamine.

21. The oral, modified-release pharmaceutical composition of claim 15 wherein the drug is

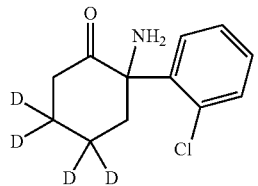

or a pharmaceutically acceptable salt thereof.

22. The oral, modified-release pharmaceutical composition of claim 15 wherein the drug is

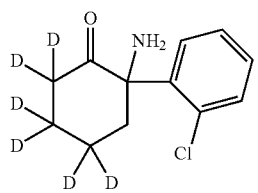

or a pharmaceutically acceptable salt thereof.

23. The compound of claim 1, wherein each of $X_1, X_2, X_3,$ and $X_4$ is hydrogen,
or a pharmaceutically acceptable salt thereof.

24. The compound of claim 1, wherein $X_5, X_6, X_7, X_8, X_9, X_{10}, X_{11},$ and $X_{12}$ are deuterium,
or a pharmaceutically acceptable salt thereof.

25. The compound of claim 1, wherein $X_{13}$ and $X_{14}$ are both deuterium, or $X_{13}$ and $X_{14}$ are both hydrogen,
or a pharmaceutically acceptable salt thereof.

26. The compound of claim 1, wherein $X_5$ and $X_6$ are both deuterium,
or a pharmaceutically acceptable salt thereof.

27. A compound of claim 1 that has the following structure:

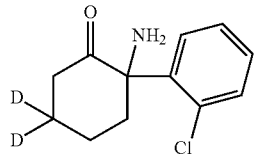

or a pharmaceutically acceptable salt thereof.

28. A compound of claim 1 that has the following structure:

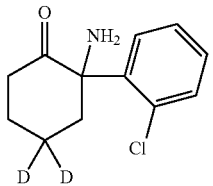 [SMILES: [2H]C1([2H])CCC(=O)C(N)(c2ccccc2Cl)C1]

or a pharmaceutically acceptable salt thereof.

29. A compound of claim 1 that has the following structure:

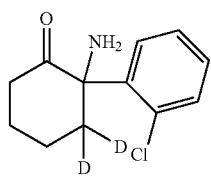 [SMILES: [2H]C1([2H])CCCC(=O)C1(N)c1ccccc1Cl]

or a pharmaceutically acceptable salt thereof.

30. A compound of claim 1 that has the following structure:

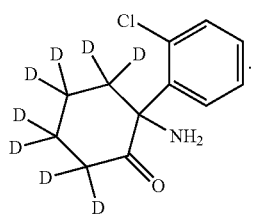

or a pharmaceutically acceptable salt thereof.

31. A compound of claim 1 that has the following structure

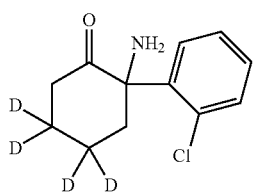 [SMILES: [2H]C1([2H])CC(=O)C(N)(c2ccccc2Cl)CC1([2H])[2H]]

or a pharmaceutically acceptable salt thereof.

32. A compound of claim 1 that has the following structure

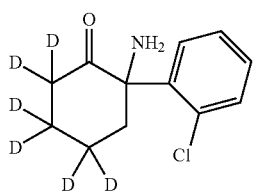

or a pharmaceutically acceptable salt thereof.

33. The method of 9 wherein the subject is suffering from or susceptible to pain.

34. The method of 9 wherein the subject is suffering from or susceptible to depression.

35. The method of claim 9 wherein the subject is suffering from or susceptible to treatment resistant depression.

36. The method of claim 9 wherein the subject is suffering from or susceptible to obsessive compulsive disorder.

37. The method of claim 9 wherein the subject is suffering from or susceptible to bipolar disorder.

38. The method of claim 9 wherein the subject is suffering from or susceptible to post traumatic stress disorder.

39. A method for treating a subject suffering from or susceptible to levodopa-induced dyskinesia; dementia, tinnitus, depression, pain, agitation resulting from or associated with Alzheimer's disease, pseudobulbar effect, autism, Bulbar function, anxiety, Alzheimer's disease, schizophrenia, diabetic neuropathy, suicidality, post-traumatic stress disorder, treatment resistant depression, major depressive disorder, generalized anxiety disorder, neuropathic pain, acute pain, chronic pain, schizophrenia, a mood disorder, substance induced psychosis, major depressive disorder, bipolar disorder, bipolar depression, anxiety, or obsessive compulsive disorder, comprising:

administering to the subject an effective of a compound selected from:

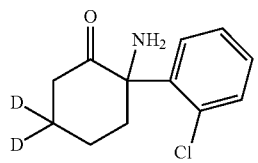

or a pharmaceutically acceptable salt thereof, or

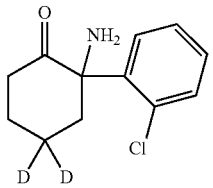 [SMILES: [2H]C1([2H])CCC(=O)C(N)(c2ccccc2Cl)C1]

or a pharmaceutically acceptable salt thereof, or

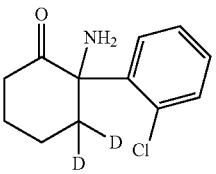 [SMILES: [2H]C1([2H])CCCC(=O)C1(N)c1ccccc1Cl]

or a pharmaceutically acceptable salt thereof, or

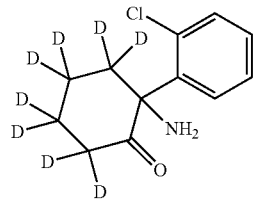

or a pharmaceutically acceptable salt thereof, or

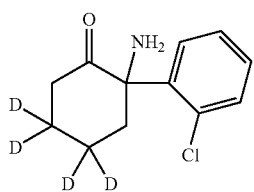 [SMILES: [2H]C1([2H])CC(=O)C(N)(c2ccccc2Cl)CC1([2H])[2H]]

or a pharmaceutically acceptable salt thereof, or

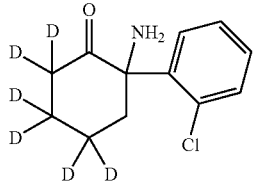

or a pharmaceutically acceptable salt thereof.

40. The method of 39 wherein the subject is suffering from or susceptible to pain.

41. The method of 39 wherein the subject is suffering from or susceptible to depression.

42. The method of claim 39 wherein the subject is suffering from or susceptible to treatment resistant depression.

43. The method of claim 39 wherein the subject is suffering from or susceptible to obsessive compulsive disorder.

44. The method of claim 39 wherein the subject is suffering from or susceptible to bipolar disorder.

45. The method of claim 39 wherein the subject is suffering from or susceptible to post traumatic stress disorder.

46. The method of claim 39 wherein the compound is

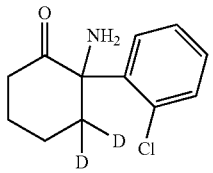 [SMILES: [2H]C1([2H])CCCC(=O)C1(N)c1ccccc1Cl]

or a pharmaceutically acceptable salt thereof.

47. The method of claim 39 wherein the compound is

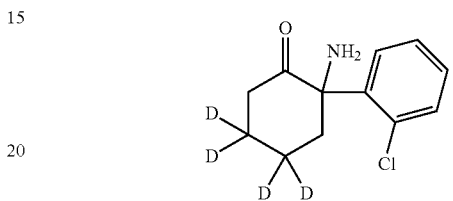

or a pharmaceutically acceptable salt thereof.

48. The method of claim 39 wherein the compound is

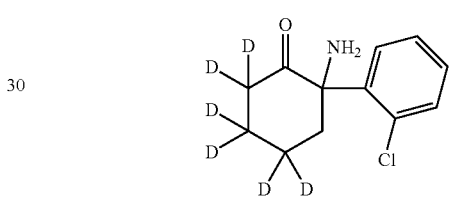

or a pharmaceutically acceptable salt thereof.

* * * * *